US010980483B2

(12) United States Patent
Kovacs et al.

(10) Patent No.: US 10,980,483 B2
(45) Date of Patent: Apr. 20, 2021

(54) REMOTE PHYSIOLOGIC PARAMETER DETERMINATION METHODS AND PLATFORM APPARATUSES

(71) Applicant: Physiowave, Inc., Santa Clara, CA (US)

(72) Inventors: Gregory T. Kovacs, Palo Alto, CA (US); Richard M. Wiard, Campbell, CA (US)

(73) Assignee: Physiowave, Inc., Menlo Park, CA (US)

( * ) Notice: Subject to any disclaimer, the term of this patent is extended or adjusted under 35 U.S.C. 154(b) by 396 days.

(21) Appl. No.: 15/354,782

(22) Filed: Nov. 17, 2016

(65) Prior Publication Data

US 2017/0143266 A1 May 25, 2017

Related U.S. Application Data

(63) Continuation of application No. PCT/US2016/062484, filed on Nov. 17, 2016, which
(Continued)

(51) Int. Cl.
*G01G 19/00* (2006.01)
*A61B 5/00* (2006.01)
(Continued)

(52) U.S. Cl.
CPC .......... *A61B 5/6887* (2013.01); *A61B 5/0015* (2013.01); *A61B 5/0205* (2013.01);
(Continued)

(58) Field of Classification Search
CPC .......... A61B 5/749; G01G 19/44; G06F 21/32
See application file for complete search history.

(56) References Cited

U.S. PATENT DOCUMENTS 3,702,113 A   11/1972   Blockley et al.
4,195,643 A    4/1980   Pratt, Jr.
(Continued)

FOREIGN PATENT DOCUMENTS

DE   202009012748      12/2009
EP      0329306 A1      2/1989
(Continued)

OTHER PUBLICATIONS

European Patent Office, Third Examination Report dated Nov. 26, 2014 for EPO Patent Application No. 07757854.0. which claims priority from PCT Application No. PCT/US2007/063244.
(Continued)

*Primary Examiner* — Puya Agahi
(74) *Attorney, Agent, or Firm* — Crawford Maunu PLLC

(57) ABSTRACT

Certain aspects of the disclosure are directed to an apparatus including a scale and external circuitry. The scale includes a platform for a user to stand on, and data-procurement circuitry for collecting signals indicative of the user's identity and cardio-physiological measurements while the user is standing on the platform. The scale includes processing circuitry to process data obtained by the data-procurement circuitry and therefrom generate cardio-related physiologic data, and an output circuit to send user data from the scale for reception at a remote location. The external circuitry receives and validates the user data as concerning a specific user associated with a user ID and determine at least one physiologic parameter of the user using the user data. Further, the external circuitry derives additional health information corresponding to the user data based on categories of interest and outputs the additional health information to the scale for display.

20 Claims, 35 Drawing Sheets

Related U.S. Application Data is a continuation of application No. PCT/US2016/062505, filed on Nov. 17, 2016.

(60) Provisional application No. 62/258,253, filed on Nov. 20, 2015, provisional application No. 62/260,174, filed on Nov. 25, 2015, provisional application No. 62/266,523, filed on Dec. 11, 2015.

(51) Int. Cl.
| | |
|---|---|
| *G01G 19/50* | (2006.01) |
| *A61B 5/11* | (2006.01) |
| *A61B 5/0402* | (2006.01) |
| *A61B 5/0205* | (2006.01) |
| *A61B 5/117* | (2016.01) |
| *G01G 19/44* | (2006.01) |
| *A61B 5/024* | (2006.01) |
| *A61B 5/021* | (2006.01) |
| *A61B 5/0535* | (2021.01) |
| *G01G 23/37* | (2006.01) |

(52) U.S. Cl.
CPC .......... *A61B 5/0402* (2013.01); *A61B 5/1102* (2013.01); *A61B 5/117* (2013.01); *A61B 5/7435* (2013.01); *G01G 19/00* (2013.01); *G01G 19/44* (2013.01); *G01G 19/50* (2013.01); *A61B 5/024* (2013.01); *A61B 5/02125* (2013.01); *A61B 5/0535* (2013.01); *A61B 5/7475* (2013.01); *G01G 23/3735* (2013.01)

(56) References Cited

U.S. PATENT DOCUMENTS

| | | |
|---|---|---|
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |
| 4,836,215 A | 6/1989 | Lee |
| 4,898,182 A | 2/1990 | Hawkins et al. |
| 4,947,857 A | 8/1990 | Albert et al. |
| 4,958,638 A | 9/1990 | Sharpe et al. |
| 5,012,411 A * | 4/1991 | Policastro .......... A61B 5/04325 600/485 |
| 5,314,389 A | 5/1994 | Dotan |
| 5,431,170 A | 7/1995 | Mathews |
| 5,620,003 A | 4/1997 | Sepponen |
| 5,678,562 A | 10/1997 | Sellers |
| 5,682,902 A | 11/1997 | Herleikson |
| 5,701,894 A | 12/1997 | Cherry et al. |
| 5,750,937 A | 5/1998 | Johnson et al. |
| 5,782,238 A | 7/1998 | Beitler |
| 5,833,623 A | 11/1998 | Mann et al. |
| 6,047,203 A | 4/2000 | Sackner et al. |
| 6,080,110 A | 6/2000 | Thorgersen |
| 6,168,563 B1 | 1/2001 | Brown |
| 6,198,394 B1 | 3/2001 | Jacobsen et al. |
| 6,205,547 B1 | 3/2001 | Davis |
| 6,228,033 B1 | 5/2001 | Koobi et al. |
| 6,292,690 B1 | 9/2001 | Petrucelli |
| 6,331,162 B1 | 12/2001 | Mitchell |
| 6,454,708 B1 | 9/2002 | Ferguson et al. |
| 6,454,719 B1 | 9/2002 | Greenhut |
| 6,516,221 B1 | 2/2003 | Hirouchi et al. |
| 6,551,252 B2 | 4/2003 | Sackner et al. |
| 6,594,759 B1 | 7/2003 | Wang |
| 6,640,134 B2 | 10/2003 | Raymond et al. |
| 6,685,634 B1 | 2/2004 | Fry |
| 6,702,754 B2 | 3/2004 | Ogura et al. |
| 6,705,990 B1 | 3/2004 | Gallant |
| 6,734,856 B2 | 5/2004 | Ishikawa et al. |
| 6,755,783 B2 | 6/2004 | Cosentino et al. |
| 6,783,498 B2 | 8/2004 | Sackner et al. |
| 6,790,178 B1 | 9/2004 | Mault et al. |
| 6,814,705 B2 | 11/2004 | Kawaguchi |
| 6,847,892 B2 | 1/2005 | Zhou et al. |
| 6,875,174 B2 | 4/2005 | Braun et al. |
| 6,898,299 B1 | 5/2005 | Brooks |
| 6,962,566 B2 | 11/2005 | Quistgaard et al. |
| 6,963,035 B2 | 11/2005 | Honda et al. |
| 7,137,955 B2 | 11/2006 | Bartels et al. |
| 7,257,438 B2 | 8/2007 | Kinast |
| 7,313,435 B2 | 12/2007 | Nakada et al. |
| 7,316,648 B2 | 1/2008 | Kelly et al. |
| 7,336,266 B2 | 2/2008 | Hayward et al. |
| 7,382,247 B2 | 6/2008 | Welch et al. |
| 7,384,410 B2 | 6/2008 | Eggers et al. |
| 7,417,536 B2 | 8/2008 | Lakshmanan et al. |
| 7,459,644 B2 | 12/2008 | Kenmochi |
| 7,502,643 B2 | 3/2009 | Farringdon et al. |
| 7,593,632 B2 | 9/2009 | Schnell |
| 7,668,588 B2 | 2/2010 | Kovacs |
| 7,787,946 B2 | 8/2010 | Stahmann et al. |
| 7,796,013 B2 | 9/2010 | Murakami et al. |
| 7,846,104 B2 | 12/2010 | MacQuarrie et al. |
| 7,899,522 B1 | 3/2011 | Koh et al. |
| 8,200,320 B2 | 6/2012 | Kovacs |
| 8,332,026 B2 | 12/2012 | Cha et al. |
| 8,369,936 B2 | 2/2013 | Farringdon et al. |
| 8,452,390 B2 | 5/2013 | Jensen |
| 8,473,041 B2 | 6/2013 | Bartnik et al. |
| 8,475,367 B1 | 7/2013 | Yuen et al. |
| 8,475,368 B2 | 7/2013 | Tran et al. |
| 8,529,409 B1 | 9/2013 | Lesea-Ames |
| 8,548,556 B2 | 10/2013 | Jensen |
| 8,639,226 B2 | 1/2014 | Hutchings et al. |
| 8,682,424 B2 | 3/2014 | Tsoglin et al. |
| 8,698,014 B1 | 4/2014 | Walstad |
| 8,858,449 B2 | 10/2014 | Inan et al. |
| 8,870,780 B2 | 10/2014 | Inan et al. |
| 9,011,346 B2 | 4/2015 | Wiard et al. |
| 9,055,871 B2 | 6/2015 | Inan et al. |
| 9,215,991 B2 | 12/2015 | Inan et al. |
| 9,241,637 B2 | 1/2016 | Wiard et al. |
| 2001/0030546 A1 | 10/2001 | Yamada et al. |
| 2001/0044588 A1 | 11/2001 | Mault |
| 2002/0002326 A1 | 1/2002 | Causey, III et al. |
| 2002/0062090 A1 | 5/2002 | Chai et al. |
| 2002/0188205 A1 | 12/2002 | Mills |
| 2003/0050537 A1 | 3/2003 | Wessel |
| 2003/0088196 A1 | 5/2003 | Steve |
| 2003/0126593 A1 | 7/2003 | Mault |
| 2003/0130567 A1 | 7/2003 | Mault et al. |
| 2003/0130595 A1 | 7/2003 | Mault |
| 2003/0149349 A1 | 8/2003 | Jensen |
| 2003/0197614 A1 | 10/2003 | Smith et al. |
| 2003/0233034 A1 | 12/2003 | Varri et al. |
| 2004/0068379 A1 | 4/2004 | Morgan et al. |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1 | 10/2004 | Kasinoff |
| 2004/0236701 A1* | 11/2004 | Beenau .................. G06F 21/32 705/64 |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0215868 A1 | 9/2005 | Kenjou et al. |
| 2005/0247494 A1 | 11/2005 | Montagnino |
| 2005/0283198 A1 | 12/2005 | Haubrich et al. |
| 2006/0049955 A1 | 3/2006 | Blum et al. |
| 2006/0079942 A1 | 4/2006 | Deno et al. |
| 2006/0106646 A1 | 5/2006 | Squilla et al. |
| 2006/0111641 A1 | 5/2006 | Manera et al. |

(56) References Cited

U.S. PATENT DOCUMENTS

| | | |
|---|---|---|
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0167286 A1 | 7/2007 | Roes |
| 2007/0197878 A1 | 8/2007 | Shklarski |
| 2007/0208232 A1 | 9/2007 | Kovacs |
| 2007/0208233 A1 | 9/2007 | Kovacs |
| 2007/0287928 A1 | 12/2007 | Kiviniemi et al. |
| 2007/0293770 A1 | 12/2007 | Bour et al. |
| 2008/0027679 A1 | 1/2008 | Shklarski |
| 2008/0073128 A1 | 3/2008 | Umemoto |
| 2008/0154645 A1 | 6/2008 | Takehara |
| 2008/0161700 A1 | 7/2008 | Sachanandani et al. |
| 2008/0183090 A1 | 7/2008 | Farringdon et al. |
| 2008/0194975 A1 | 8/2008 | MacQuarrie et al. |
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0016582 A1 | 1/2009 | Penn et al. |
| 2009/0024044 A1 | 1/2009 | Virtanen et al. |
| 2009/0102296 A1 | 4/2009 | Greene et al. |
| 2009/0182204 A1 | 7/2009 | Semler et al. |
| 2009/0203972 A1 | 8/2009 | Heneghan et al. |
| 2009/0234916 A1* | 9/2009 | Cosentino ............... G16H 10/60 709/203 |
| 2009/0240194 A1 | 9/2009 | Keimel et al. |
| 2009/0284496 A1 | 11/2009 | Oki |
| 2009/0287933 A1 | 11/2009 | Beckwith et al. |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |
| 2010/0174205 A1 | 7/2010 | Wegerif |
| 2010/0210921 A1 | 8/2010 | Park et al. |
| 2010/0262044 A1 | 10/2010 | Siegler |
| 2011/0015504 A1* | 1/2011 | Yoo ...................... A61B 5/0002 600/301 |
| 2011/0040352 A1 | 2/2011 | Gerber et al. |
| 2011/0054359 A1 | 3/2011 | Sazonov et al. |
| 2011/0080181 A1 | 4/2011 | Sato et al. |
| 2011/0152695 A1 | 6/2011 | Granqvist et al. |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skeri et al. |
| 2012/0266250 A1 | 10/2012 | Uhl |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0006669 A1 | 1/2013 | Nakamura |
| 2013/0056285 A1 | 3/2013 | Meagher |
| 2013/0113506 A1 | 5/2013 | Poupyrev et al. |
| 2013/0226601 A1 | 8/2013 | Razmi et al. |
| 2013/0289889 A1 | 10/2013 | Yuen et al. |
| 2013/0310700 A1 | 11/2013 | Wiard et al. |
| 2014/0032234 A1* | 1/2014 | Anderson ............... G06Q 50/22 705/2 |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman et al. |
| 2014/0182952 A1 | 7/2014 | Yuen et al. |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0193497 A1 | 7/2015 | Tallamy et al. |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1 | 4/2016 | Sharma |
| 2016/0317043 A1 | 11/2016 | Campo et al. |

FOREIGN PATENT DOCUMENTS

| | | |
|---|---|---|
| ES | 2296474 A1 | 4/2008 |
| ES | 2328205 B1 | 8/2010 |
| ES | 2385898 A1 | 8/2012 |
| ES | 2398439 A2 | 3/2013 |
| ES | 2398542 A2 | 3/2013 |
| GB | 2225459 | 5/1990 |
| GB | 2367896 A | 4/2002 |
| JP | 2001198096 | 7/2001 |
| JP | 2001309893 | 11/2001 |
| JP | 2002119488 | 4/2002 |
| JP | 2006212155 | 8/2006 |
| JP | 2007283071 A | 11/2007 |
| JP | 2009050508 A | 3/2009 |
| KR | 0137272 B1 | 4/1998 |
| KR | 100452533 | 10/2004 |
| KR | 20050079235 A | 8/2005 |
| WO | 2005074379 A2 | 8/2005 |
| WO | 2006088280 A1 | 8/2006 |
| WO | 2007103835 | 9/2007 |
| WO | 2008102298 A1 | 8/2008 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |
| WO | 2013017717 A2 | 2/2013 |
| WO | 2013066642 A1 | 5/2013 |
| WO | 2014151133 | 9/2014 |

OTHER PUBLICATIONS

China State Intellectual Property Office, Office Action dated Oct. 13, 2010 for CN Patent Application No. 200780015788.1.

Japan Patent Office, Notice of Reasons for Rejection dated Mar. 6, 2012 for JPO Patent Application No. P2008-558484. which claims priority from PCT Application No. PCT/US2007/063244; Reference 1 cited in the Notice of Reaons for Rejection corresponds to U.S. Appl. No. 08/555,546, now U.S. Pat. No. 5,701,894, Cherry et al., Reference 2, US 20030050537, Wessel.

European Patent Office, Extended European Search Report dated Feb. 12, 2010 for EPO Application No. 07757854.0.

International Search Report and Written Opinion of the International Searching Authority for PCT International App. No. PCT/US07/63244.

Discera, "Shrinking Wireless Architectures", available for download from www.discera.com prior to Mar. 3, 2006.

GeTeMed GmbH, "Baby Monitoring System Vitaguard VG3000", Teltow, Germany, 1997-1999, available at http://www.fuse-nelwork.com/fuse/demonstration/331/24571.pdf.

Atmel, "Microcontroller with 16 K Bytes In-System Programmable Flash", Atmel Atmega, document contains notation AVR 06/05.

Kaminska, Wireless Wearable Biomonitors for Lifetime Wellness Optimization, Proceedings of the 3rd Annual International IEEE EMBS Special Topic Conference on Microtechnologies in Medicine and Biology, Kahuku, Oahu, Hawaii, May 2005. Abstract Only.

NorthEast Monitoring Inc., "Hotter LX Pro Software—Operator's Manual", NorthEast Monitoring Inc. Two Clock Tower Suite 360 Maynard Massachusetts 01754, Apr. 2003.

(56) References Cited

OTHER PUBLICATIONS

Nguyen et al., "Transceiver Front-End Architectures Using Vibrating Micromechanical Signal Processors", Dig. of Papers, Topical Meeting on Silicon Monolithic Integrated Circuits in RF Systems: 23-32, Sep. 4, 2001.
ANSI/AAMI, EC11:1991/(R) 2001, Diagnostic Electrogardiographic Devices, 2000.
ANSI/MM I, EC38: 1998, Ambulatory Electrocardiographs, 1999.
Nguyen et al., "Frequency-Selective MEMS for Miniaturized Low-Power Communication Devices", IEEE Trans. Microwave Theory Tech 47(8):1486-1503, Aug. 1999.
Nguyen et al., "An Integrated CMOS Micromechanical Resonator High-Q Oscillator", IEEE Journal of Solid-State Circuits 34(4), Apr. 1999.
Nguyen et al., "Micromachined Devices for Wireless Communications," Proc. IEEE 86(8):1756-1768, Aug. 1998.
Kovacs, "Micromachined Transducers-Sourcebook", McGraw-Hill, New York, New York, 1998 944 page book.
Desel et al., "A CMOS Nine Channel ECG Measurement IC", ASIC 1996 2nd International Conference: 115-118, Oct. 1996 Abstract Only.
Fraunhofer, "Medical Technolology", http://www.iis.fraunhofer.de/en/ff/med.html Dec. 26, 2005.
Toumaz "Technology", Nov. 8, 2005.
Kaminiski, "Wearable Biomonitors With Wireless Network Communication" draft of paper published in Proceedings of the 3rd Annual International IEEE EMBS Special Topic Conference on Microtechnologies in Medicine and Biology, Kahuku, Oahu, Hawaii, May 2005.
Novosense AB, "Company", Apr. 4, 2005.
IMEC, "Sensor Electronics", available for download at http://www.imec be/wwwinter/ mediacenter/en/SR2004/scientificreport/competencies/c14/sr101_cont.html, Mar. 31, 2005.
Novosense, AB, "Technology", available for download at http://www.novosense.se/technology.html Aug. 5, 2015.
Miromico AG, "Sample Projects", available for download at http://www.miromico.ch/index.php?sec-ad.sa&lang=2, page includes notice of Copyright 2005 Miromico.
Mori, Narumi, et al. "Clinical assessment of a new method for pacing pulse detection using a hybrid circuit in digital Holter monitoring." Japanese circulation journal 64.8 (2000): 583-589.
Pyron, "Pyron Introduces ECG ASIC Monitoring Subsystem", Electronic News, Nov. 29, 1999, available for download at http://wvw.end.com/article/CA52794.html.
Nguyen, Clark T-C., and Roger T. Howe. "An integrated CMOS micromechanical resonator high-Q oscillator." Solid-State Circuits, IEEE Journal of 34.4 (1999): 440-455.
Grossbach, Wolfgang. "Measuring the ECG Signal with a Mixed Analog-Digital Application-Specific IC." Hewlett-Packard Journal 42.4 (1991): 21-24. Abstract Only.
I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 714-732 (1961).
D.C. Deuchar, S.A. Talbot, and W.R. Scarborough, "Some Observations on the Relation of the High- Frequency Bed Ballistocardiogram to that Obtained from an Aperiodic Bed," Circulation, vol. 11, pp. 228-239 (1955).
H. Mandelbaum and R.A. Mandelbaum, "Studies Utilizing the Portable Electromagnetic Ballistocardiograph: IV. The clinical Significance of Serial Ballistocardiograms Following Acute Myocardial Infarction," Circulation, vol. 7, pp. 310-9165 (1953).
R.S. Guber, M. Rodstein and H.E. Ungerleider, "Ballistocardiograph: An Appraisal of Technic, Physiological Principles, and Clinic Value," Circulation, vol. 7, DD. 268-286 (1953).
M.B. Rappaport, H.B. Sprague, and W.B. Thompson, "Ballistocardiography: I. Physical Considerations," Circulation, vol. 7, pp. 229-246 (1953).

O. Tannenbaum, J. Schack and H. Vesell, "Relationship between Ballistocardiographic Forces and Certain Events in the Cardiac Cycle," Circulation, vol. 6, DD. 586-592 (1952).
T.E. Satterthwaite, "Cardiovascular Diseases: Recent Advances in Their Anatomy, Physiology, Pathology, Diagnosis and Treatment," Lemcke and Beuschner, New York, NY (1913).
J.W. Gordon, "On Certain Molar Movements of the Human Body Produced by the Circulation of the Blood," J. of Anat. and Phys., vol. 11, DD. 533-536 (1877).
Gonzalez, et al. "Detection of las frecuencias 1-9 cardiaca and respitatoria mediante una bascu the electronica" In: IFMBE Proceedings. vol. 18, pp. 448-451, 2008. Springer-Verlag Berlin Heidelberg. Abstract Only.
Gomez-Clapers J. et al. "Pulse arrival time estimation from the impedance plethysmogram obtained with a handheld device", 33rd Annual International Conference of the IEEE EMBS, Boston, USA, Mar. 8-9, 2011, pp. 516-519. Abstract only.
HeartForce Medical Inc. "definitions and Terminologies: History of Seismocardiology." www.heartforcemedical.com 4 pages.
Shin et al., "Non-constrained monitoring of systolic blood pressure on a weighing scale", Physiological Measurement, vol. 30, No. 7, pp. 679-693, 2009 Abstract Only.
Pliquett et al., "Front end with offset-free symmetrical current source optimized for time domain impedance spectroscopy", Physiological Measurement, vol. 32, No. 7, 2011.I Abstract Only.
Earbud Ballistocardiogram: HeadSense Israel: http://head-sense-med.com/ http://www.medgadget.com/2013/07/headsense-intracranial-pressure-monitoring-earbuds.html.
Bifrostec & The Kaiteki Institute http://www.psfk.com/2013/11/earbud-heart-monitor.html#IzIKRT.
http://www.endgadget.com/2014/01/06/intel-smart-earbuds/.
Mitchell et al., "Arterial Stiffness and Cardiovascular Events The Framingham Heart Study" . Circulation 2010, 121: 505-11.
Blacher et al., "Impact of Aortic Stiffness on Survival in End-Stage Renal Disease" Circulation, 1999: 99.
Blacher et al., "Arterial Calcifications, Arterial Stiffness, and Cardiovascular Risk in End Stage Renal Disease" Hypertension. 38: 938-942 (2001).
Di Micco, et al., "Daily dialysis reduces pulse wave velocity in chronic hemodialysis patients". Hypertension Research. vol. 35, 2012.
Laurent S et al., "Expert consensus document on arterial stiffness: methodological issues and clinical applications", European Heart Journal (2006) 27, 2588-2605.
Boutouyrie P et al., "Assessment of arterial stiffness for clinical and epidemiological studies: methodological considerations for validation and entry into the European Renal and Cardiovascular Medicine registry", Nephrol Dial Transplant (2014) 29: 232-239.
Stewart A D. et al., "Acute Reduction of Blood Pressure by Nitroglycerin Does Not Normalize Large Artery Stiffness in Essential Hypertension", Hypertension 2006, 48: 404-410.
Stewart A D. et al., "Effects of Inhibition of Basal Nitric Oxide Synthesis on Carotid-Femoral Pulse Wave Velocity and Augmentation Index in Humans", Hypertension 2003, 42: 915-918.
Avolio A P., et al., "Effects of aging on changing arterial compliance and left ventricular load in a northern Chinese urban community", Circulation 68, No. 1, 50-58, 1983.
Wilkinson, I B. et al., "Artery Society guidelines for validation of non-invasive haemodynamic measurement devices: Part 1, arterial pulse wave velocity" Artery Research (2010) 4, 34-40.
Avolio A P., et al. "Improved Arterial Distensibility in Normotensive Subjuects on a Low Salt Diet", Arteriosclerosis 6: 166-169, 1986.
Balkestein E J., et al., "The effect of weight loss with or without exercise training on large artery compliance in healthy obese men", J. Hypertens 1999, 17: 1831-1835.
Laurent S, et al., "Mesure de la Rigidite Arterielle" Dec. 2013.
Wiard, Richard M., et al. "Preliminary results from standing ballistocardiography measurements in microgravity." 2013 35th Annual International Conference of the IEEE Engineering in Medicine and Biology Society (EMBC). IEEE, 2013. Abstract only.
Inan, Omer T., et al. "Noninvasive measurement of physiological signals on a modified home bathroom scale." IEEE Transactions on Biomedical Engineering 59.8 (2012): 2137-2143. Abstract only.

(56) References Cited

OTHER PUBLICATIONS

Giovangrandi, Laurent, et al. "Preliminary results from BCG and ECG measurements in the heart failure clinic." 2012 Annual International Conference of the IEEE Engineering in Medicine and Biology Society. IEEE, 2012. Abstract only.

Park, Dookun, Omer T. Inan, and Laurent Giovangrandi. "A combined heartbeat detector based on individual BCG and IPG heartbeat detectors." 2012 Annual International Conference of the IEEE Engineering in Medicine and Biology Society. IEEE, 2012. Abstract only.

Etemadi, Mozziyar, et al. "Rapid assessment of cardiac contractility on a home bathroom scale." IEEE transactions on information technology in biomedicine 15.6 (2011): 864-869. Abstract only.

Giovangrandi, L., et al. "Ballistocardiography—a method worth revisiting." Conference proceedings: . . . Annual International Conference of the IEEE Engineering in Medicine and Biology Society. IEEE Engineering in Medicine and Biology Society. Annual Conference. vol. 2011. NIH Public Access, 2010.

Inan, Omer T., et al. "Multi-signal electromechanical cardiovascular monitoring on a modified home bathroom scale." 2011 Annual International Conference of the IEEE Engineering in Medicine and Biology Society. IEEE, 2011. Abstract only.

Wiard, R. M., et al. "Estimation of central aortic forces in the ballistocardiogram under rest and exercise conditions." Conference proceedings: . . . Annual International Conference of the IEEE Engineering in Medicine and Biology Society. IEEE Engineering in Medicine and Biology Society. Annual Conference. vol. 2009. NIH Public Access, 2008.

Etemadi, Mozziyar, et al. "Non-invasive assessment of cardiac contractility on a weighing scale." 2009 Annual International Conference of the IEEE Engineering in Medicine and Biology Society. IEEE, 2009. Abstract only.

Inan, Omer T., et al. "Non-invasive measurement of valsalva-induced hemodynamic changes on a bathroom scale ballistocardiograph." 2008 30th Annual International Conference of the IEEE Engineering in Medicine and Biology Society. IEEE, 2008. Abstract only.

Inan, Omer T., et al. "Unobtrusive Monitoring of Cardiovascular Health at Home Using a Modified Weighing Scale." 6th European Conference of the International Federation for Medical and Biological Engineering. Springer International Publishing, 2015. Abstract only.

McCall, Corey, et al. "Standing ballistocardiography measurements in microgravity." 2014 36th Annual International Conference of the IEEE Engineering in Medicine and Biology Society. IEEE, 2014. Abstract only.

Inan, Omer Tolga. Novel technologies for cardiovascular monitoring using ballistocardiography and electrocardiography. Dissertation Abstracts International, vol. 70. No. 10. 2009. Abstract only.

Wiard, Richard Matthew. Validation of Non-invasive Standing Arterial Stiffness Measurements Using Ballistocardriography and Photoplethysmography. 2012. Abstract only.

J. Alametsäet al. "Ballistocardiogaphic studies with acceleration and electromechanical film sensors." Medical Engineering & Physics 31 (2009), p. 1154-1165.

J. Alametsäet al. "Arterial Elasticity Measurements with Ankle Pulse Width Velocity and Ballistocardiography." ECIFMBE 2008, IFMBE Proceedings 22, p. 1636-1641.

J. Allen. "Photoplethysmography and its application in clinical physiological measurement." Physiol. Meas. 28, 2007, p. R1-R39.

A. Avolio et al. "Role of Pulse Pressure Amplification I Arterial Hpertension: Experts' Opinion and Review of the Data." Hypertension, vol. 54, Aug. 1, 2009, p. 375-383.

J. Blacher et al. "Aortic Pulse Wave Velocity as a Marker of Cardiovascular Risk in Hypertensive Patients," Hypertension, vol. 33, 1999, p. 1111-1117.

Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.

G. Kim et al. "Vascular Variation of PTT and the Vascular Characteristic Index According to the Posture Change." In Proceedings of the 2007 International Conference on Convergence Information Technology (ICCIT '07). IEEE computer Society, Nov. 2007, p. 2426-2425. Abstract Only.

E. Pinheiro et al. "Non-Intrusive Device for Real-Time Circulatory System Assessment with Advanced Signal Processing Capabilities." Measurement Science Review, vol. 10, No. 5, 2010, p. 167-175.

E. Pinheiro et al. "Pulse arrival time and ballistocardiogram application to blood pressure variability estimation." Medical Measurements and Applications, 2009. IEEE Workshop, May 29-30, 2009. Abstract only.

M. Safar. "Arterial aging—hemodynamic changes and therapeutic options." Nat Rev Cardiol, vol. 7, 207, p. 442-449. Abstract / Introduction Only.

R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.

R. Wiard et al. "Automatic detection of motion artifacts in the ballistocardiogram measured on a modified bathroom scale." Med Biol Eng Comput (2011) 49:213-220. Published online Dec. 9, 2010.

B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.

O.T. Inan, M. Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).

Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.

Inan OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract / Introduction Only.

Inan OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.

DeLoach SS, Twonsend RR, "Vascular Stiffness: Its Measurement and Significance for Epidemiologic and Outcome Studies", Clin J Am Soc Nephrol, 3: 184-192,2008. Abstract / Introduction Only.

Webster's Ninth New Collegiate Dictionary, Meriam-Webster Inc., 1990, p. 1152.

Alan Fang et al., "Using a Geophone for Vibration Cancellation in a STM," abstract, Bulletin of the American Physical Society, 2008 APS March Meeting, vol. 53, No. 2, Mar. 10, 2008.

De Viries, S. O. et al., "Prediction of the Left Ventricular Mass from the Electrogram in Systemic Hypertension," American Journal of Cardiology, May 1, 1996;777(11):974-8. (Abstract Only).

A.Akhbardeh, M. Koivuluoma, T. Koivistoinen and A. Varri, "Ballistocardiogram Diagnosis Using Neural Networks and Shift-Invariant Daubechies Wavelet Transform," Researchers at Institute of Signal Processing, Tampere University ofTechnololgy, Tampere 33101, Finland.

O. Inan, et al., "Evaluating the Foot Electromyogram Signal as a Noise Reference for a Bathroom Scale Ballistocardiogram Recorder," Stanford University, Department of EE, Department of Bioengineering.

O. Inan and G. Kovacs, "An 11 µW, Two-Electrode Transimpedance Biosignal Amplifier with Active Current Feedback Stabilization," IEEE Transactions on Biomedical Circuits and Systems (2009).

O. Inan, M. Etemadi, B. Widrow and G. Kovacs, "Adaptive cancellation of floor vibrations in standing ballistocardiogram measurements using a seismic sensor as a noise reference," IEEE (2009).

(56) References Cited

OTHER PUBLICATIONS

R. F. Yazicioglu, P. Merken, R. Puers and C. Van Hoof, "A 60 µW 60 nV/..JHz Readout Front-End for Portable Biopotential Acquisition Systems," IEEE Journ. Of Solid-State Circuits, vol. 42, No. 5 (May 2007).

W. Rosamond et al., "Heart Disease and Stroke Statistics -2007 Update: A Report from the American Heart Association Statistics Committee and Stroke Statistics Subcommittee," Circ., vol. 115, pp. 69-171 (2007).

R. R. Harrison, "A Versatile Integrated Circuit for the Acquisition of Biopotentials," IEEE CICC, pp. 115-122 (2007).

T. Denison, K. Consoer, W. Santa, A.-T. Avestruz, J. Cooley, and A. Kelly, "A 2µW JOO nV/rtHz, Chopper-Stabilized Instrumentation Amplifier for Chronic Measurement of Neural Field Potentials," IEEE Jour. Solid-State Circuits, vol. 42, No. 12, DD. 2934-2945 (2007).

A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

C.N. Chien and F.S. Jaw, "Miniature ultra-low-power biopotential amplifier for potable [sic} applications," Biomedical Engineering-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. in Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Portable ECG Recorders," Proc. IEEE A.S.S.C.C., DD. 473-476 (2005).

J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

D.M. Linton and u. Giion, "Advances in noninvasive cardiac output monitoring," Annals of cardiac Anaesthesia, vol. 5, pp. 141-148 (2002).

M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).

K. Lu, J. W. Clark, Jr. F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: a review and analysis," Brain Research Reviews, vol. 29, DD. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, DD. 750-755 (1983).

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).

R.P. Lewis, S.E. Rittogers, W.F. Froester, and H. Boudoulas, "A critical review of the systolic time intervals," Circulation, vol. 56, DD. 146-158 (1977).

\* cited by examiner

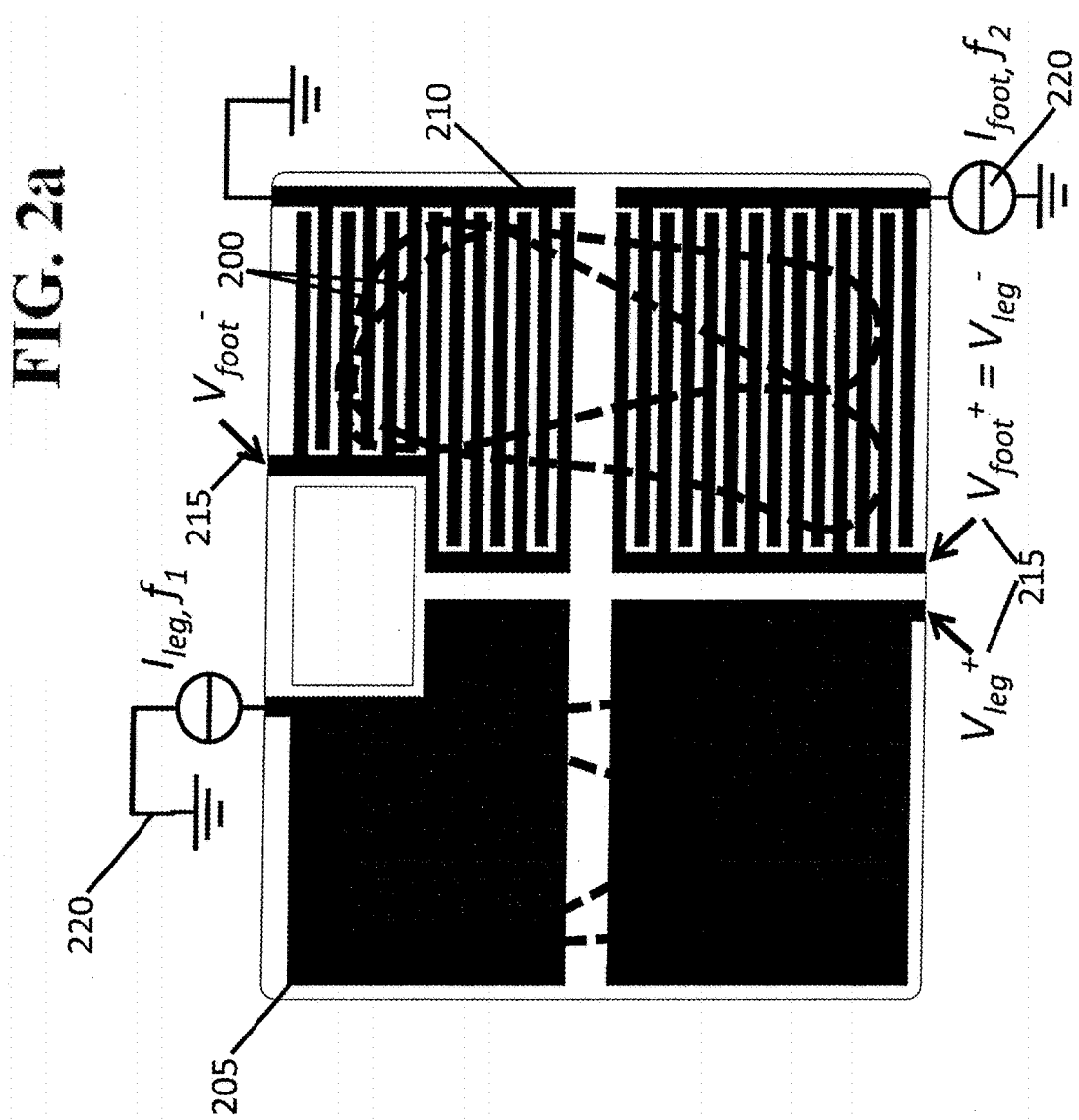

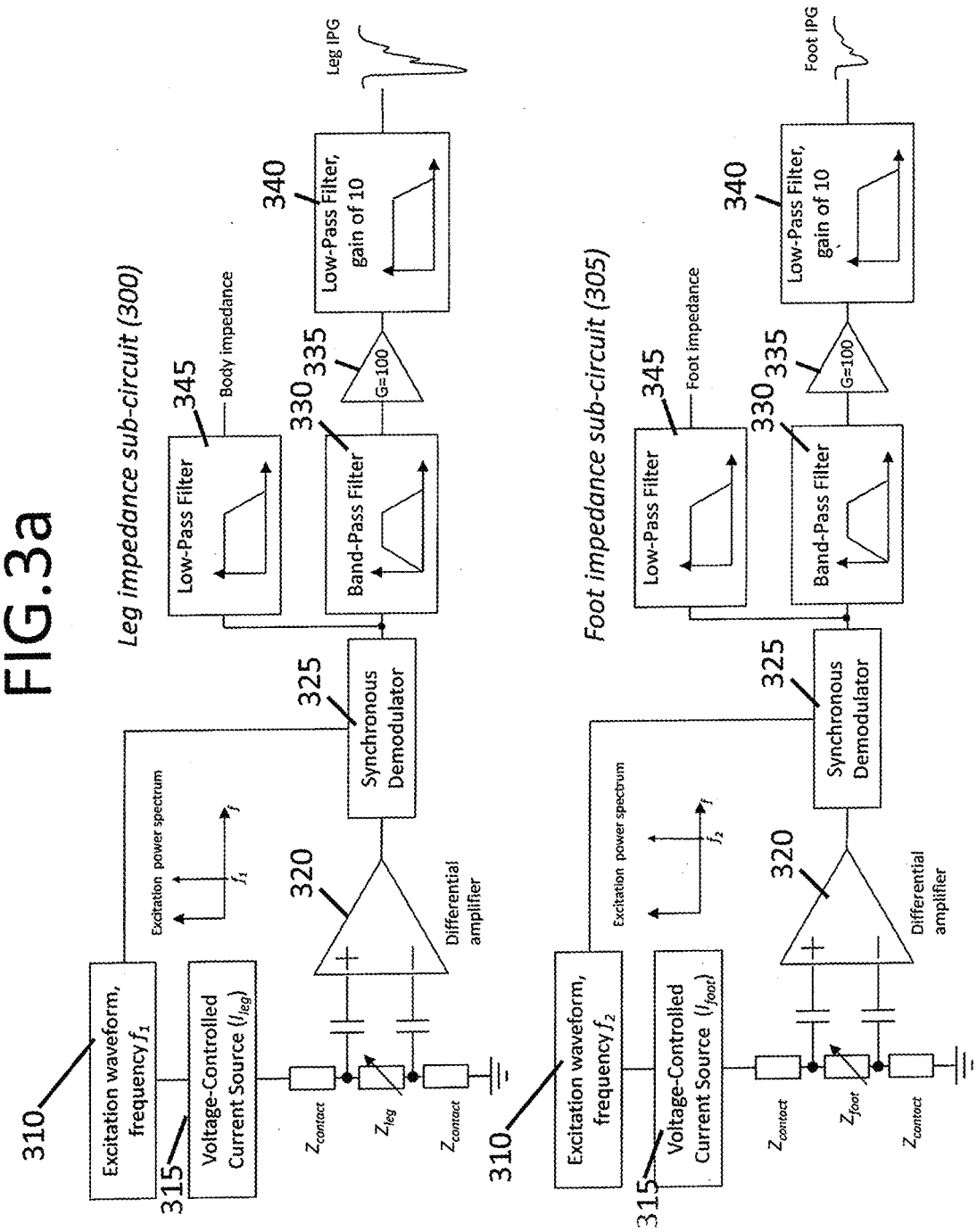

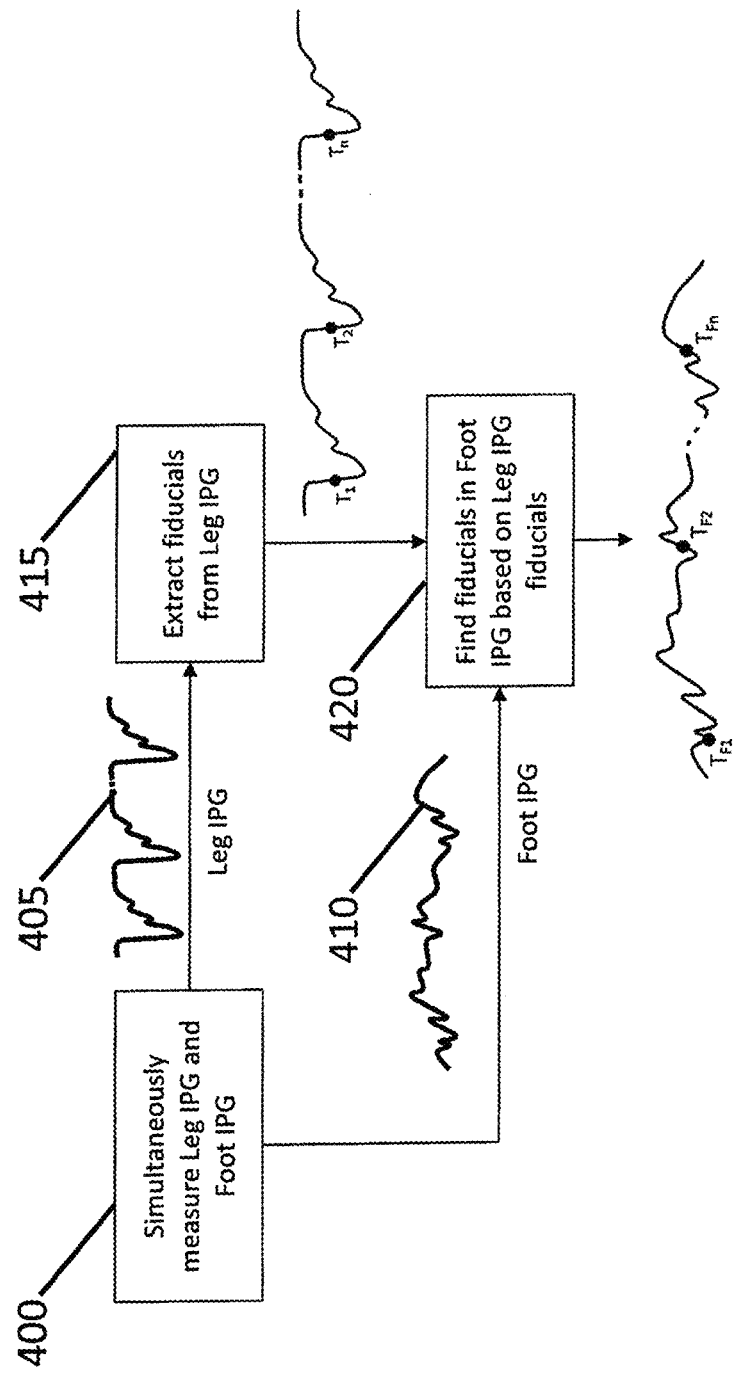

Example of high-quality Foot IPG signals (Vertical units are arbitrary)

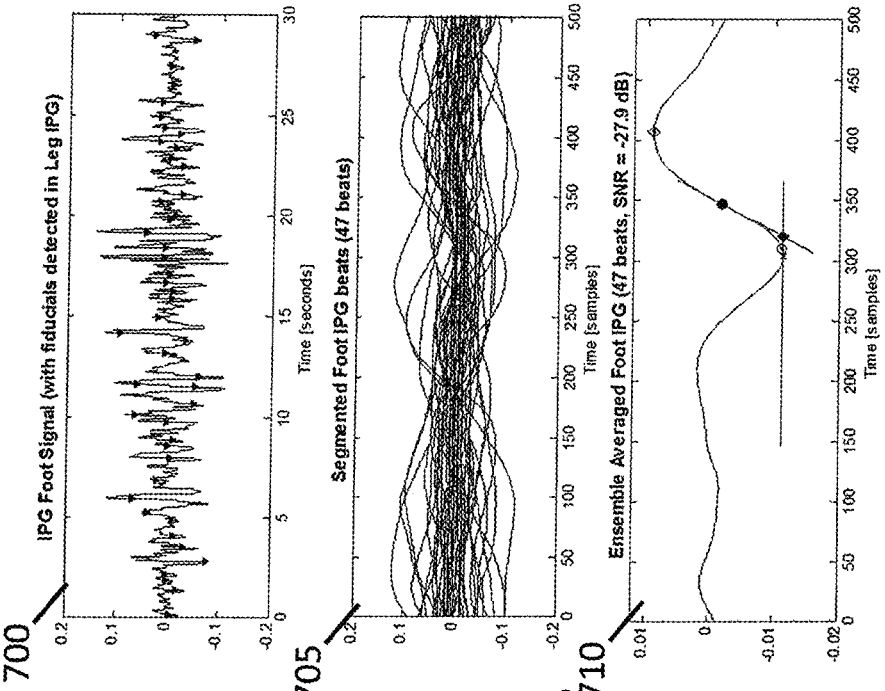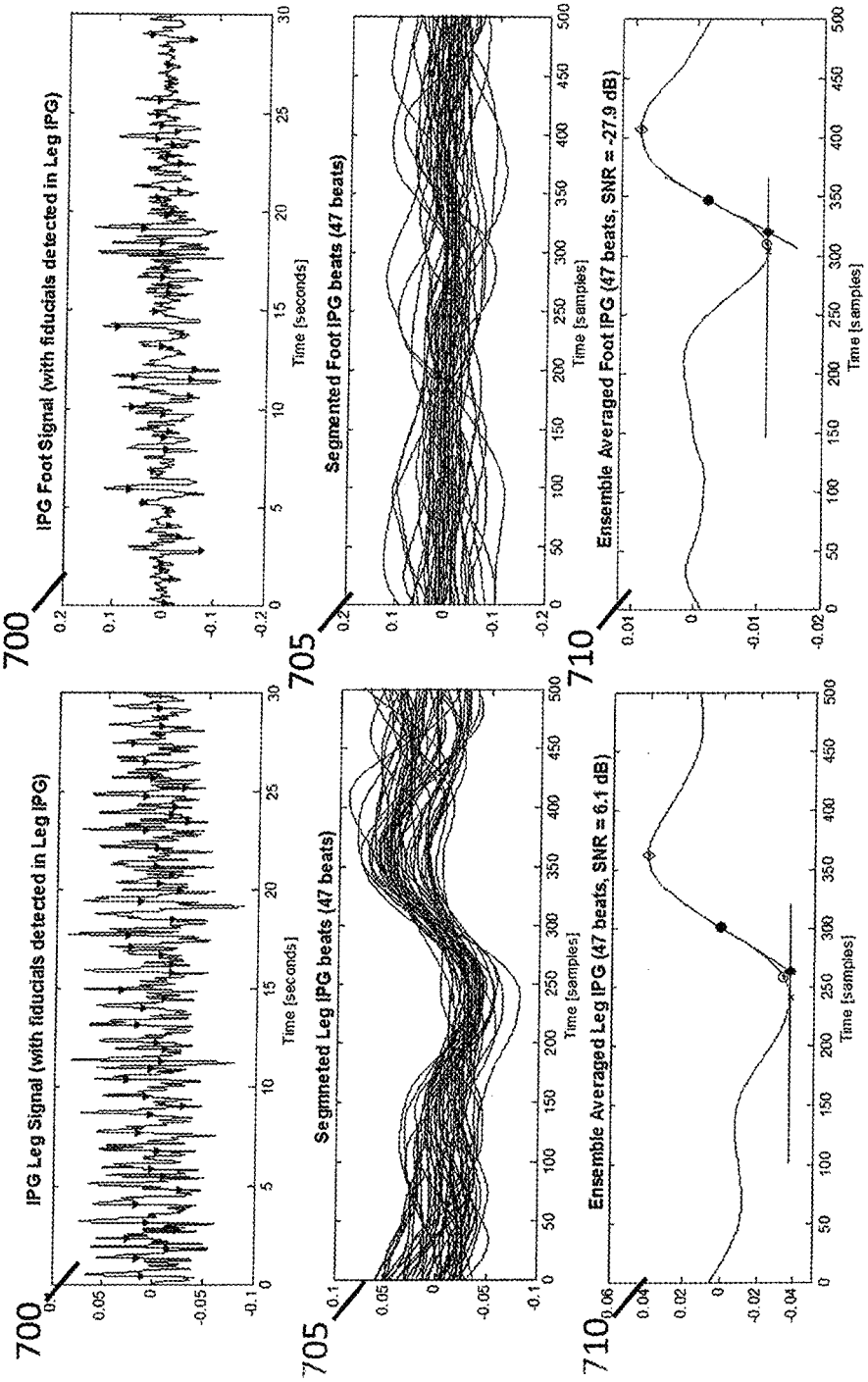

Metric of Leg IPG triggering robustness, based on various heart rates in 61 subjects for a standardized 30-second recording interval

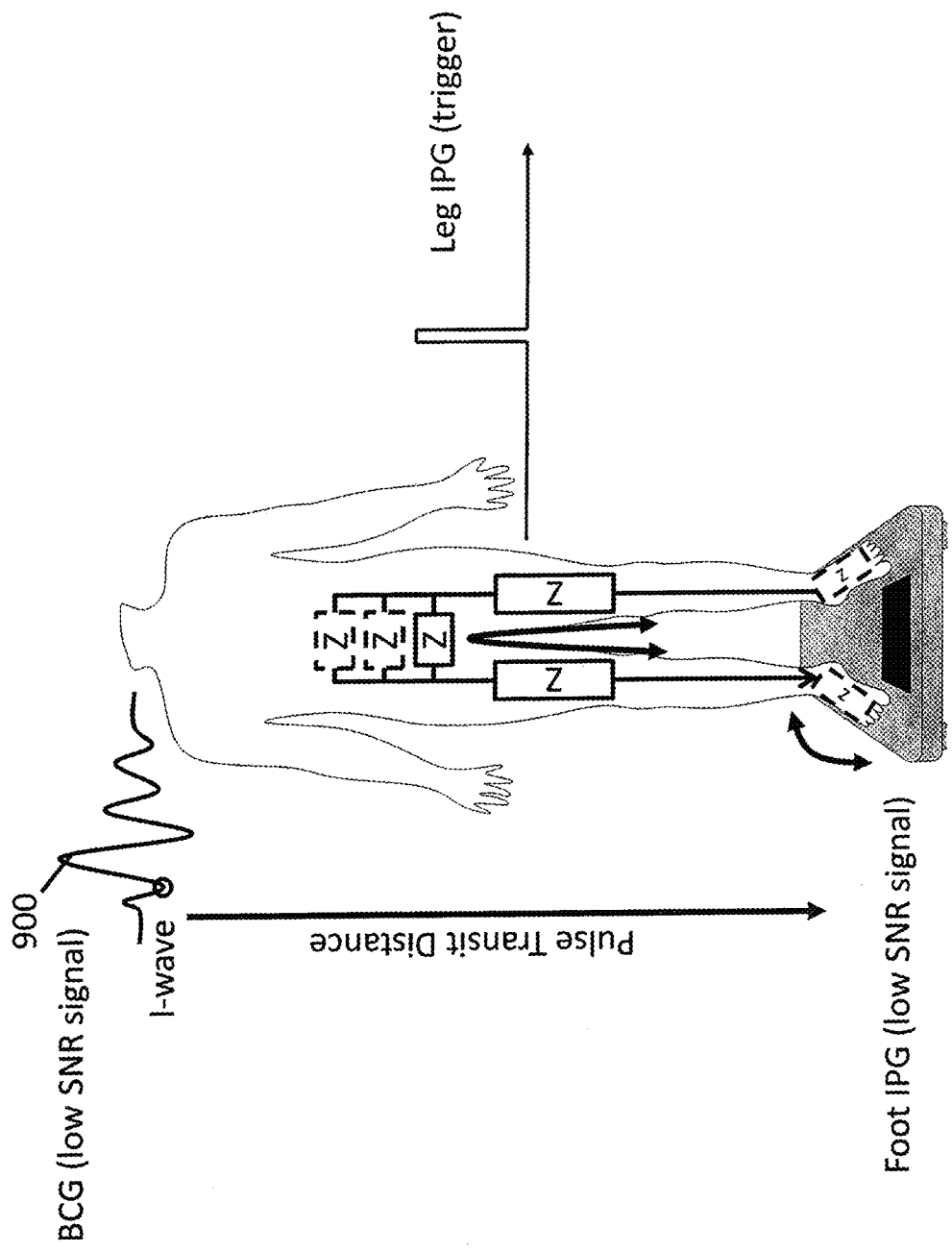

Switched, ground-referenced current source implementation

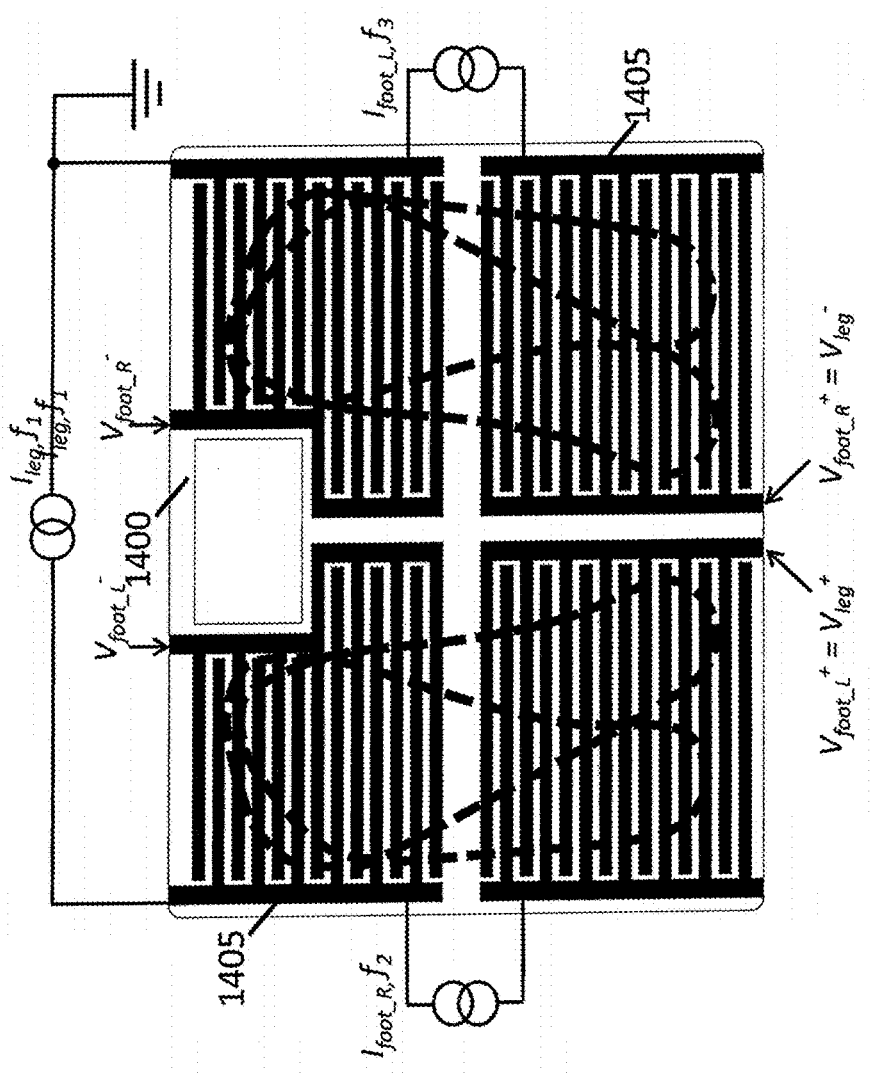
FIG.14b Floating current source implementation

Transformer-coupled, grounded-load current source implementation

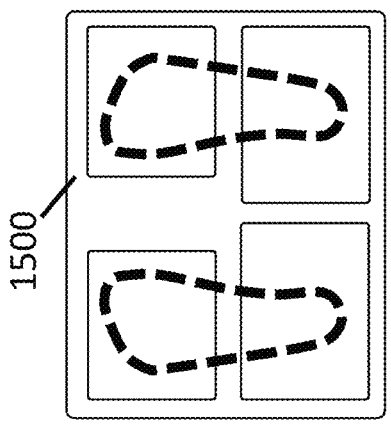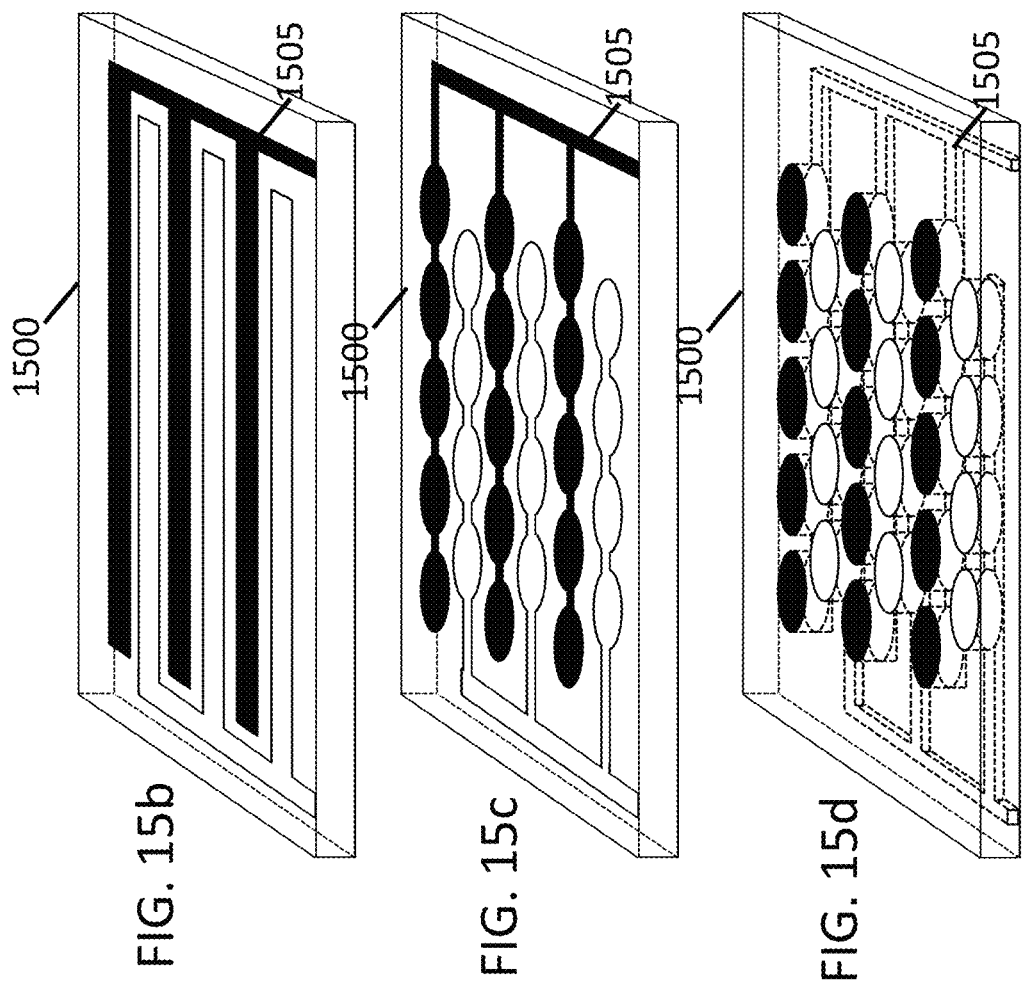

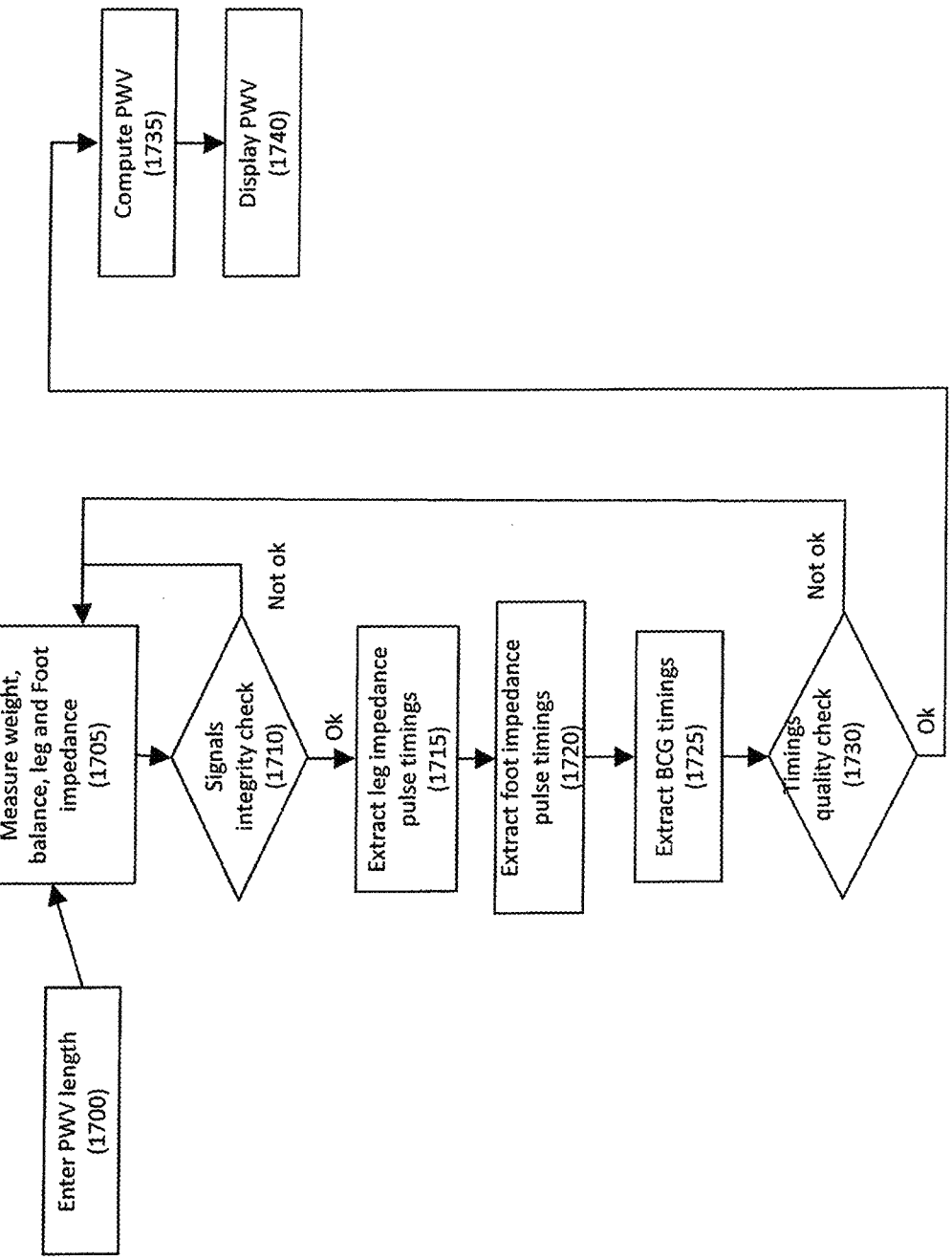

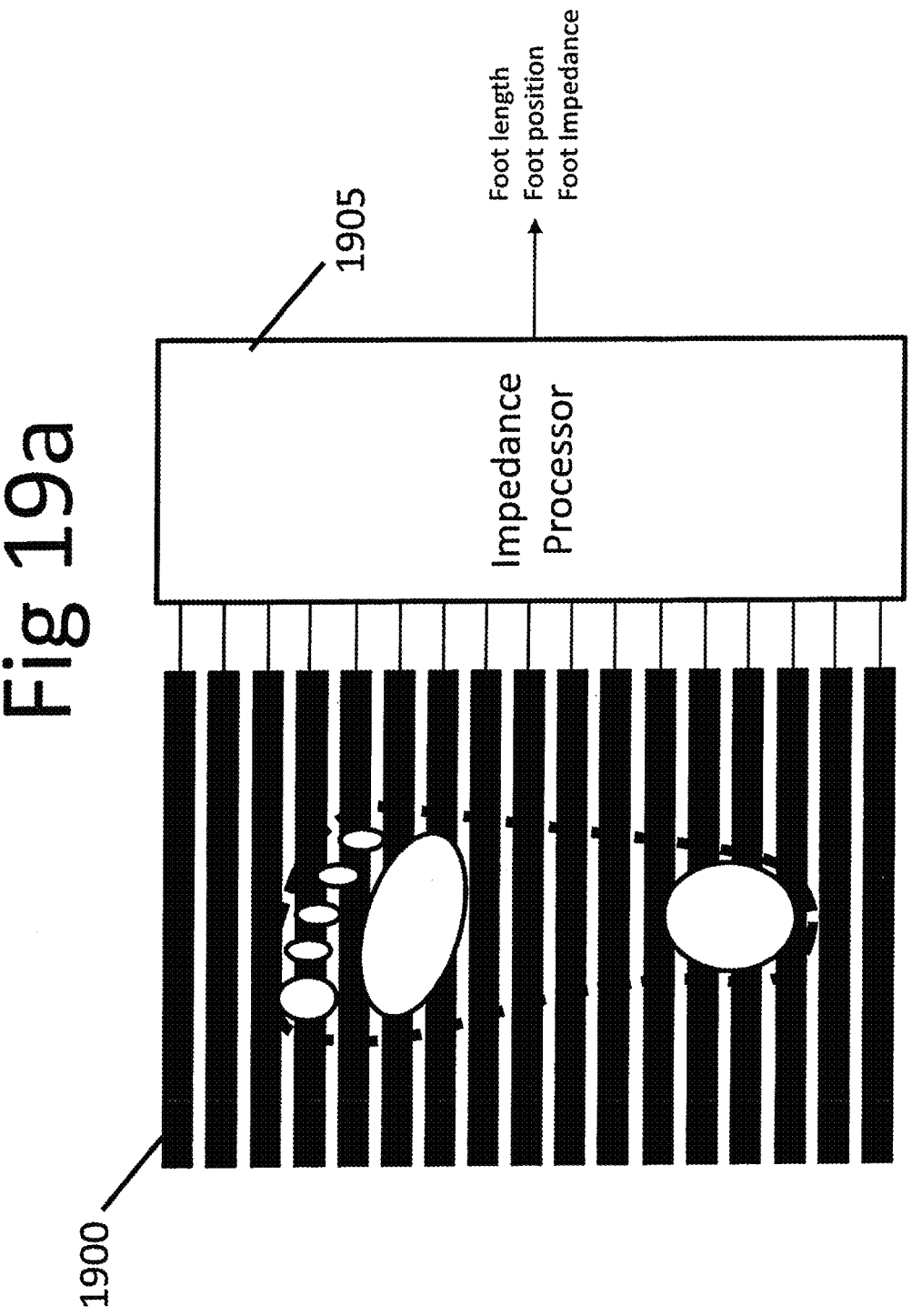

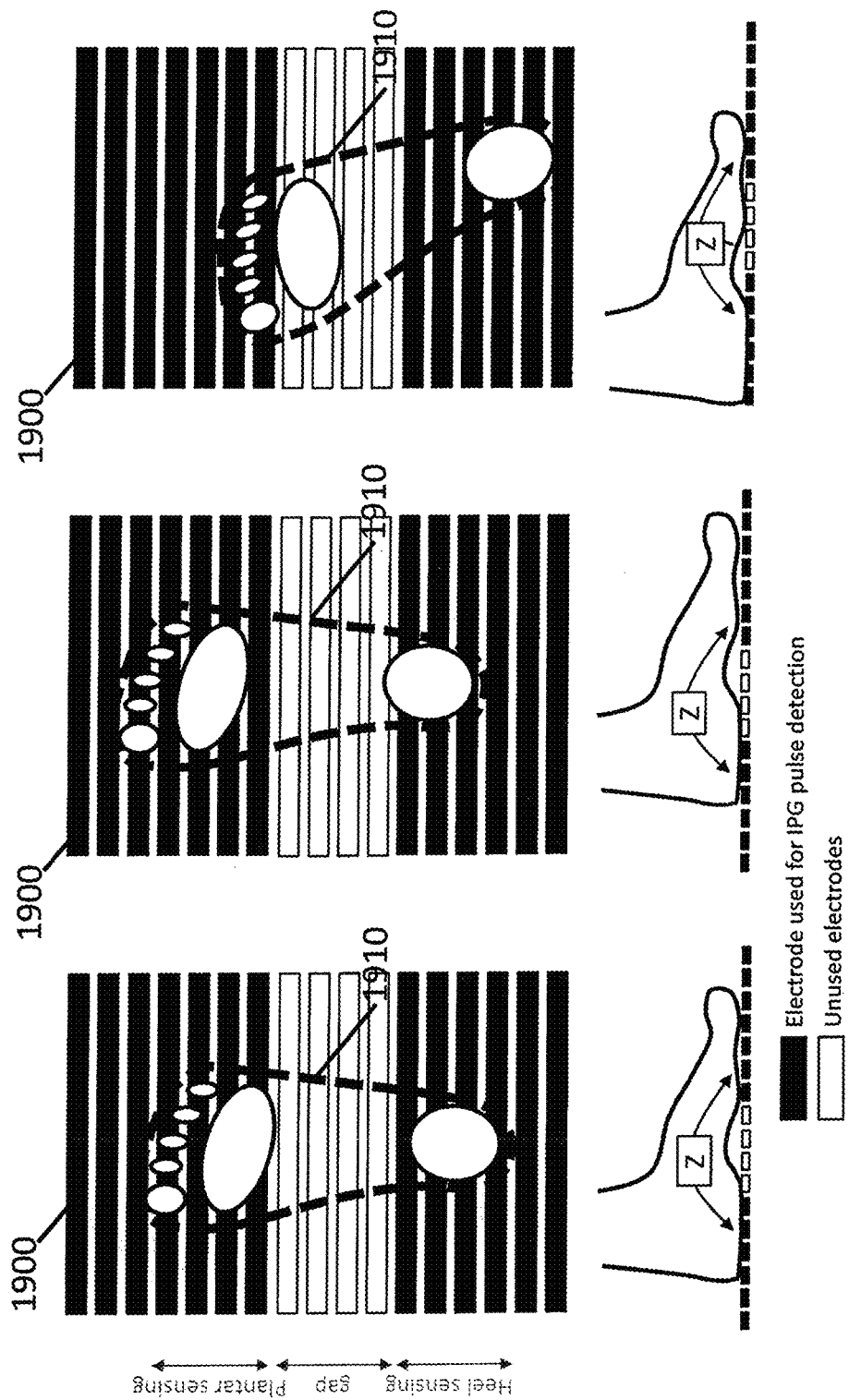

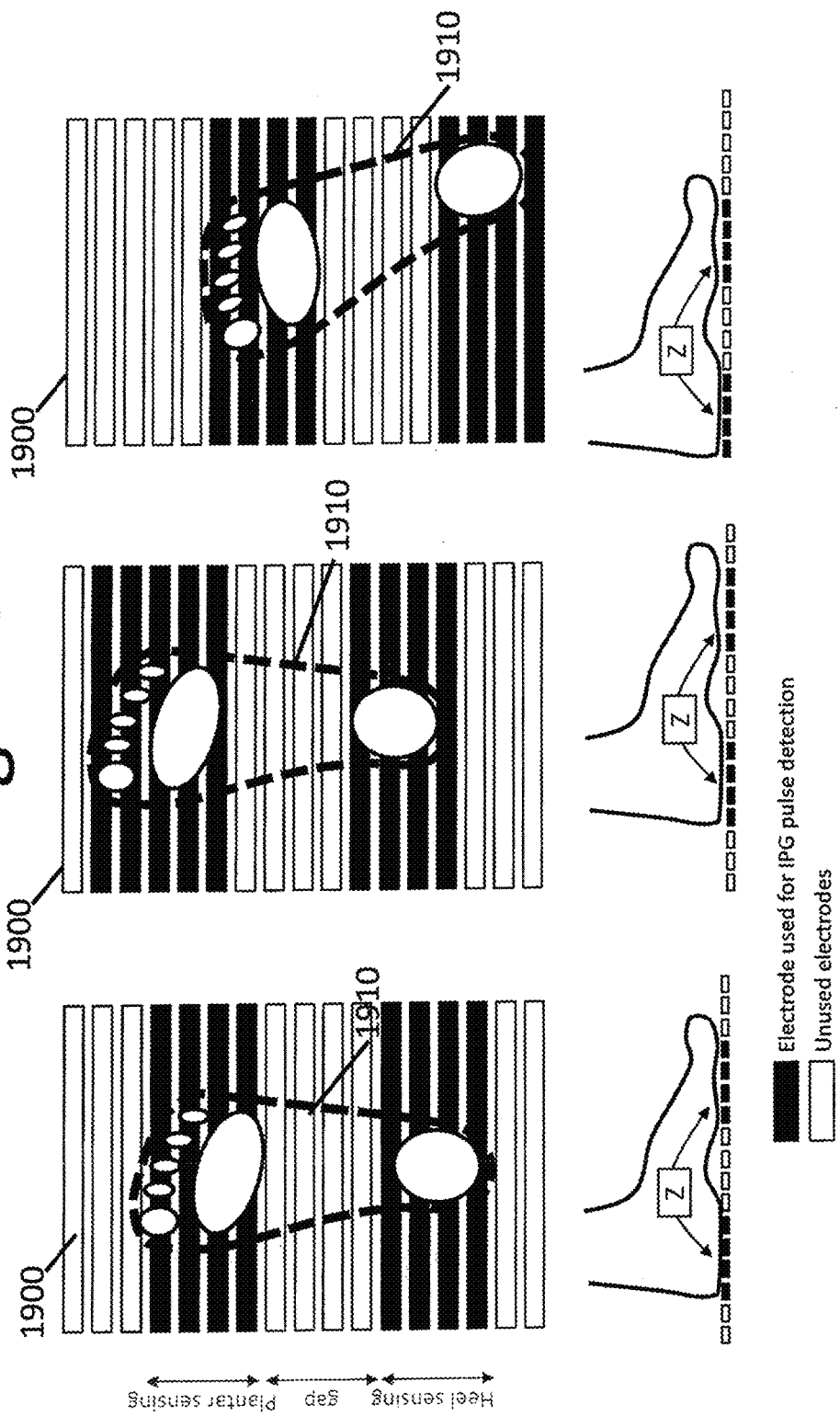

REMOTE PHYSIOLOGIC PARAMETER DETERMINATION METHODS AND PLATFORM APPARATUSES

RELATED APPLICATION DATA

This application is related to PCT Application (Ser. No. PCT/US2016/062484), entitled "Scale-Based Parameter Acquisition Methods and Apparatuses", filed on Nov. 17, 2016, PCT Application (Ser. No PCT/US2016/062505), entitled "Remote Physiologic Parameter Assessment Methods and Platform Apparatuses", filed on Nov. 17, 2016, U.S. Provisional Application (Ser. No. 62/258,253), entitled "Initialization Method and Devices and User Physiological Platforms", filed Nov. 20, 2015, U.S. Provisional Application (Ser. No 62/260,174), entitled "Remote Physiological Parameter Determination Methods and Platform Apparatuses", filed Nov. 25, 2015, and U.S. Provisional Application (Ser. No. 62/266,523) entitled "Social Grouping Using a User-Specific Scale-Based Enterprise System", filed Dec. 11, 2015", which are fully incorporated herein by reference.

Overview

Various aspects of the present disclosure are directed toward methods, systems and apparatuses that are useful in remotely determining a physiologic parameter of a user using user data obtained by a scale.

Various aspects of the present disclosure are direct toward monitoring a variety of different physiological characteristics for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient.

Obtaining physiological signals (e.g., data) can often require specialty equipment and intervention with medical professionals. For many applications, such requirements may be costly or burdensome. These and other matters have presented challenges to monitoring physiological characteristics.

Various aspects of the present disclosure are directed toward multisensory biometric devices, systems and methods. Aspects of the present disclosure include user-interactive platforms, such as scales, large and/or full platform-area or dominating-area displays and related weighing devices, systems, and methods. Additionally, the present disclosure relates to electronic body scales that use impedance-based biometric measurements. Various other aspects of the present disclosure are directed to biometrics measurements such as body composition and cardiovascular information. Impedance measurements can be made through the feet to measure fat percentage, muscle mass percentage and body water percentage. Additionally, foot impedance-based cardiovascular measurements can be made for an ECG and sensing the properties of blood pulsations in the arteries, also known as impedance plethysmography (IPG), where both techniques can be used to quantify heart rate and/or pulse arrival timings (PAT). Cardiovascular IPG measures the change in impedance through the corresponding arteries between the sensing electrode pair segments synchronous to each heartbeat.

In certain embodiments, the present disclosure is directed to apparatuses and methods including a scale and external circuitry. The scale includes a platform for a user to stand on, data-procurement circuitry, processing circuitry, and an output circuit. The data-procurement circuitry includes force sensor circuitry and a plurality of electrodes integrated with the platform and configured for engaging the user with electrical signals and collecting signals indicative of the user's identity and cardio-physiological measurements while the user is standing on the platform, processing circuitry, and an output circuit. The processing circuitry includes a CPU and a memory circuit with user-corresponding data stored in the memory circuit. The processing circuitry is arranged with (e.g., electrically integrated with or otherwise in communication) the force sensor circuitry and the plurality of electrodes and configured and arranged to process data obtained by the data-procurement circuitry while the user is standing on the platform and therefrom generate cardio-related physiologic data corresponding to the collected signals. The output circuit receives the user data and, in response, sends the user data, including the data indicative of the user's identity and the generated cardio-related physiologic data, from the scale for reception at a remote location. The output circuit further displays the user's weight and data indicative of the user's identity and/or the generated cardio-related physiologic data corresponding to the collected signals using a user interface, which is internal or external to the scale. The external circuitry is configured and arranged to receive and validate the user data as concerning a specific user associated with a user ID and determine physiologic parameters of the user using the user data.

A number of embodiments include methods for remotely determining physiologic parameters. For example, the method includes engaging a user, via a scale, with electrical signals and, therefrom, collecting signals indicative of the user's identity while the user is standing on a platform of the scale. The scale includes a user display to display data to a user while the user is standing on the scale and the platform for a user to stand on. Further, the scale includes data-procurement circuitry, processing circuitry, and output circuitry. The data-procurement circuitry includes force sensor circuitry and a plurality of electrodes integrated with the platform. The processing circuitry includes a CPU and a memory circuit with user-corresponding data stored in the memory circuit. The processing circuitry is configured and arranged within the scale and under the platform upon which the user stands, and is electrically integrated with the force sensor circuitry and the plurality of electrodes. The method further includes processing, using the processing circuitry, data obtained by the data-procurement circuitry while the user is standing on the platform and therefrom generating cardio-related physiologic data corresponding to the collected signals and displaying the user's weight on the user display. User data is output, using the output circuit, from the scale for reception by external circuitry at a remote location. The user data includes the data indicative of the user's identity and the generated cardio-related physiologic data. The method further includes validating the user data as concerning a specific user associated with a user ID, and determining, using the external circuitry, at least one physiologic parameter of the user using the user data.

In another specific embodiment, a method includes receiving, at external circuitry, user data corresponding to a plurality of users from a plurality of scales, the user data including cardio-physiological measurements. Each scale includes a user display to display data to a user while the user is standing on the scale, a platform for a user to stand on, data-procurement circuitry, processing circuitry, and an output circuit. The data-procurement circuitry includes force-sensor circuitry and a plurality of electrodes integrated with the platform configured and arranged for engaging the user with electrical signals and collecting signals indicative of the user's identity and cardio-physiological measurements while the user is standing on the platform. The processing circuitry is arranged with the plurality of electrodes to receive the collected signals obtained by the data-procurement circuitry and, in response, derive and output the user data to the external circuitry for assessment at a remote location that is not integrated within the scale. The method includes receiving and validating the user data as concerning a respectively plurality of users associated with user IDs. The method includes identifying the respective plurality of users based on the user data received from the plurality of scales, correlating the user data with respective user profiles based on the identification of the respective plurality of users, determining, using the external circuitry, at least one physiologic parameter of each respective plurality of users using the respective user data. The physiologic parameter includes parameters selected from the group consisting of: pulse wave velocity, cardiac output, pre-ejection period, stroke volume, and a combination thereof.

In another embodiments, an apparatus comprises a plurality of scales and external circuitry. Each scale includes a user display to display data to a user while the user is standing on the scale, a platform for a user to stand on, data-procurement circuitry, and processing circuitry. The data-procurement circuitry includes force-sensor circuitry and a plurality of electrodes integrated with the platform configured and arranged for engaging the user with electrical signals and collecting signals indicative of the user's identity and cardio-physiological measurements while the user is standing on the platform. The processing circuitry is arranged with the plurality of electrodes to receive the collected signals obtained by the data-procurement circuitry and, in response, derive and output the user data to the external circuitry for assessment at a remote location that is not integrated within the scale. The external circuitry receives the user data corresponding to a plurality of users from the plurality of scales, the user data including cardio-physiological measurements and data indicative of the user's identity. Further, the external circuitry validates the user-data as concerning the respective plurality of users based on the user data received from the plurality of scales and determines, using the external circuitry, at least one physiologic parameter of each respective user using the respective user data.

In certain embodiments, aspects of the present disclosure are implemented in accordance with and/or in combination with aspects of the underlying PCT Application (Ser. No. PCT/US2016/062484), entitled "Scale-Based Parameter Acquisition Methods and Apparatuses", filed on Nov. 17, 2016, PCT Application (Ser. No. PCT/US2016/062505), entitled "Remote Physiologic Parameter Assessment Methods and Platform Apparatuses", filed on Nov. 17, 2016, U.S. Provisional Application (Ser. No. 62/258,253), entitled "Initialization Method and Devices and User Physiological Platforms", filed Nov. 20, 2015, U.S. Provisional Application (Ser. No 62/260,174), entitled "Remote Physiological Parameter Determination Methods and Platform Apparatuses", filed Nov. 25, 2015, and U.S. Provisional Application (Ser. No. 62/266,523) entitled "Social Grouping Using a User-Specific Scale-Based Enterprise System", filed Dec. 11, 2015", which are fully incorporated herein by reference.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which:

FIG. 2a shows an example of the insensitivity to foot placement on scale electrodes with multiple excitation and sensing current paths, consistent with various aspects of the present disclosure;

FIGS. 3a-3b show example block diagrams depicting circuitry for sensing and measuring the cardiovascular time-varying IPG raw signals and steps to obtain a filtered IPG waveform, consistent with various aspects of the present disclosure;

FIG. 4 shows an example block diagram depicting signal processing steps to obtain fiducial references from the individual Leg IPG "beats," which are subsequently used to obtain fiducials in the Foot IPG, consistent with various aspects of the present disclosure;

FIG. 7a shows examples of the Leg IPG signal with fiducials; the segmented Leg IPG into beats; and the ensemble averaged Leg IPG beat with fiducials and calculated SNR, for an exemplary low-quality recording, consistent with various aspects of the present disclosure;

FIG. 7b shows examples of the Foot IPG signal with fiducials derived from the Leg IPG fiducials; the segmented Foot IPG into beats; and the ensemble-averaged Foot IPG beat with fiducials and calculated SNR, for an exemplary low-quality recording, consistent with various aspects of the present disclosure;

FIGS. 9a-b show an example configuration to obtain the pulse transit time (PTT), using the first IPG as the triggering pulse for the Foot IPG and ballistocardiogram (BCG), consistent with various aspects of the present disclosure;

FIG. 14b shows another example of a scale with interleaved foot electrodes to inject and sense current from one foot to another foot, and measure Foot IPG signals in both feet, consistent with various aspects of the present disclosure;

FIGS. 15a-d show an example breakdown of a scale with interleaved foot electrodes to inject and sense current from one foot to another foot, and within one foot, consistent with various aspects of the present disclosure;

FIG. 17 shows an example flow diagram, consistent with various aspects of the present disclosure;

FIGS. 19a-c show example impedance as measured through different parts of the foot based on the foot position, consistent with various aspects of the present disclosure.

Figure 1A:
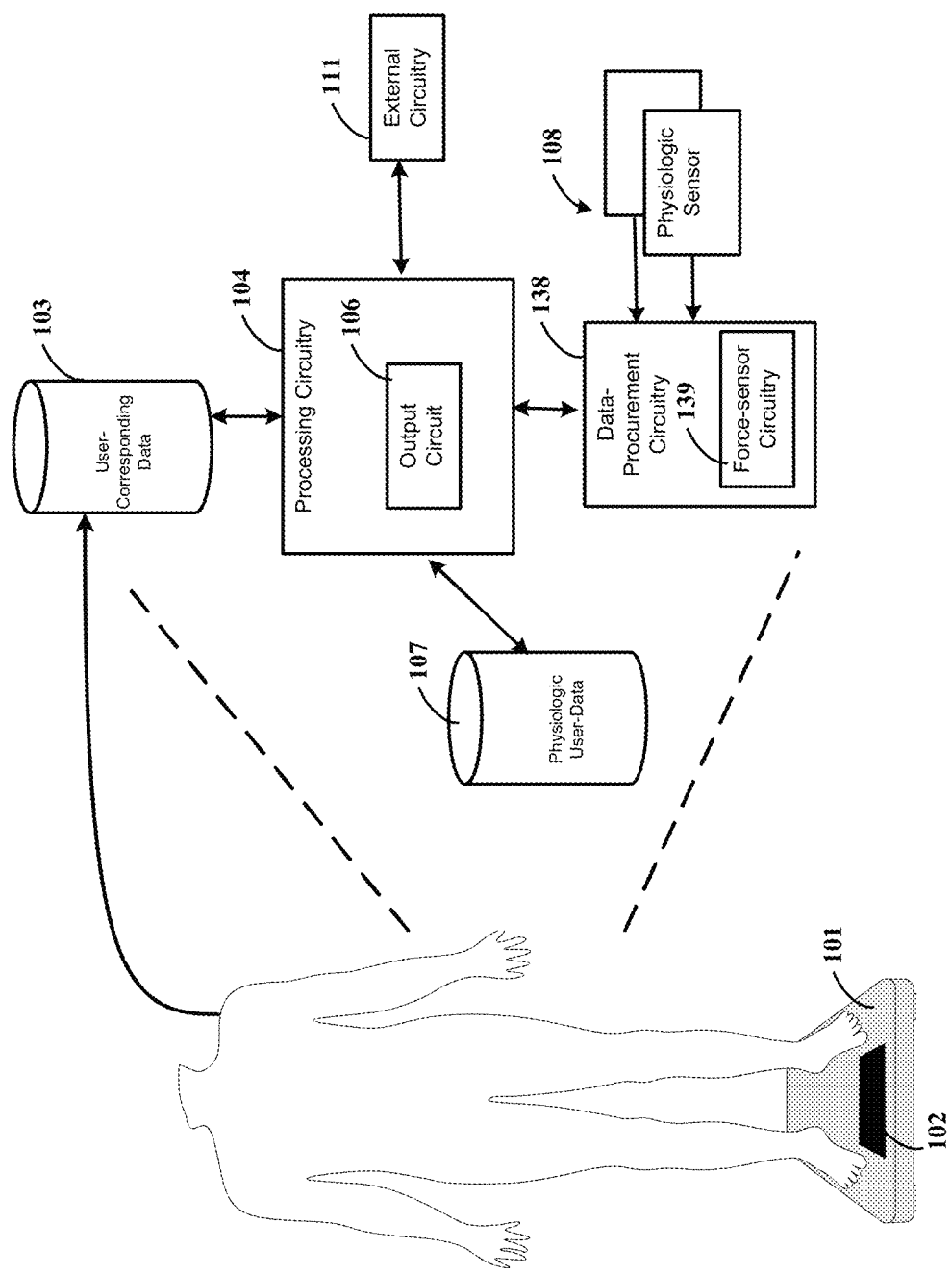
FIG. 1a shows an apparatus consistent with aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems, and methods involving remotely determining physiologic parameters of a user using user data obtained by a scale. In certain implementations, aspects of the present disclosure have been shown to be beneficial when used in the context of a weighing scale with electrodes configured for engaging with the user and generating cardio-related physiologic data, such as data indicative of a BCG or ECG of a user. In some embodiments, the external circuitry determines the physiologic parameters, which can include clinical indicators that may not be displayed to the user. The external circuitry controls access to information by not allowing access to the clinical indicators to the user, without a prescription from a physician, while still allowing access to other data such as bodyweight, body mass index, heart rate, body fat percentage, and cardiovascular age. These and other aspects can be implemented to address challenged, including those discussed in the background above. While not necessarily so limited, various aspects may be appreciated through a discussion of examples using such exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

In accordance with a number of embodiments, physiologic parameter data is collected using an apparatus, such as a weighing scale or other platform that the user stands on. The user (e.g., co-workers, friends, roommates, colleagues), may use the apparatus in the home, office, doctors office, or other such venue on a regular and frequent basis, the present disclosure is directed to a substantially-enclosed apparatus, as would be a weighing scale, wherein the apparatus includes a platform which is part of a housing or enclosure and a user display to output user-specific information for the user while the user is standing on the platform. The platform includes a surface area with electrodes that are integrated and configured and arranged for engaging a user as he or she steps onto the platform. Within the housing is processing circuitry that includes a CPU (e.g., one or more computer processor circuits) and a memory circuit with user-corresponding data stored in the memory circuit. The platform, over which the electrodes are integrated, is integrated and communicatively connected with the processing circuitry. The processing circuitry is programmed with modules as a set of integrated circuitry which is configured and arranged for automatically obtaining a plurality of measurement signals (e.g., signals indicative of cardio-physiological measurements) from the plurality of electrodes. The processing circuitry generates, from the signals, cardio-related physiologic data manifested as user data.

The user data, in various embodiments, is processed to determine physiologic parameters of the user and other data, such as cardio-physiological data and wellness data. The physiologic parameters, in various embodiments, includes information that is regulated by a government agency, such as the Food and Drug Administration (FDA), and/or otherwise requires a prescription from a physician for the user to obtain. The other data, such as the cardio-physiological data and wellness data, by contrast, includes derived measurements that are "non-regulated" by agencies, such as the FDA. To obtain such information, a user may purchase a scale and use the scale over the counter and without a physician's prescription. The scale, if the user data is further processed, can provide the additional prescription (Rx) health information to the user, via the physiologic parameters, that may be beneficial for the user or the user's physician to access. However, the user may be unable to access the information without a prescription from a physician and/or could not purchase the scale in the first place without a prescription if the scale was enabled to provide the Rx health information. Embodiments in accordance with the present disclosure include processing the user data on external circuitry to determine physiologic parameters, which can include Rx health information. In various embodiments, the external circuitry controls access to the Rx health information by allowing a physician to access to the information but not a user. The user is provided access to non-regulated data, such as other additional health information, and granted access to the Rx health information in response to a prescription from the physician. Furthermore, the Rx health information is used to update a user profile, such as a user health profile at the physician's office.

In accordance with various embodiments, the external circuitry receives user data from a plurality of scales. Each scale provides data for one or more different users and/or can be located at different locations. The external circuitry identifies the users corresponding to the received user data, validates the user data as concerning the identified users, and correlates the user data with profiles based on identification of the respective plurality of users. The external circuitry provides physiologic parameters, such as diagnosis, conditions, and/or treatments, PWV, cardiac output, pre-ejection period and stroke volume by processing the data from the scales. In some specific aspects, the external circuitry controls access to the profiles by allowing access to physiologic parameters and other data to a physician and not allowing access to the physiologic parameters to the users. In various embodiments, the external circuitry allows access to other data to the user, without a prescription. For example, the external circuitry allows access by granting access to the respective profile or portions of the data in the profile and/or by sending the respective data to the scale (or another user device) for display. Example data that is non-regulated by an agency and can be provided to the user without a prescription includes bodyweight, body mass index, heart rate, body-fat percentage, and cardiovascular age. By controlling access to the physiologic parameters, that includes Rx health information, the scale provides the advanced functions of determining the clinical indications while being sold over-the-counter and the user can access this data through their physician. The physiologic parameters can be used by the physician for further analysis and/or to provide health advice and/or diagnosis, such as medications.

In accordance with various embodiments, the user data is based on sensing, detection, and quantification of at least two simultaneously acquired impedance-based signals. The simultaneously acquired impedance-based signals are associated with quasi-periodic electro-mechanical cardiovascular functions, and simultaneous cardiovascular signals measured by the impedance sensors, due to the beating of an individual's heart, where the measured signals are used to determine at least one cardiovascular related characteristic of the user for determining the heart activity, health, or abnormality associated with the user's cardiovascular system. The sensors can be embedded in a user platform, such as a weighing scale-based platform, where the user stands stationary on the platform, with the user's feet in contact with the platform, where the impedance measurements are obtained where the user is standing with bare feet.

In certain embodiments, the plurality of impedance-measurement signals includes at least two impedance-measurement signals between the one foot and the other location. Further, in certain embodiments, a signal is obtained, based on the timing reference, which is indicative of synchronous information and that corresponds to information in a BCG. Additionally, the methods can include conveying modulated current between selected ones of the electrodes. The plurality of impedance-measurement signals may, for example, be carried out in response to current conveyed between selected ones of the electrodes. Additionally, the methods, consistent with various aspects of the present disclosure, include a step of providing an IPG measurement within the one foot. Additionally, in certain embodiments, the two electrodes contacting one foot of the user are configured in an inter-digitated pattern of positions over a base unit that contains circuitry communicatively coupled to the inter-digitated pattern. The circuitry uses the inter-digitated pattern of positions for the step of determining a plurality of pulse characteristic signals based on the plurality of impedance-measurement signals, and for providing an IPG measurement within the one foot. As discussed further herein, and further described in U.S. patent application Ser. No. 14/338,266 filed on Oct. 7, 2015, which is herein fully incorporated by reference for its specific teaching of inter-digitated pattern and general teaching of sensor circuitry, the circuitry can obtain the physiological data in a number of manners.

In medical (and security) applications, for example, the impedance measurements obtained from the plurality of integrated electrodes can then be used to provide various cardio-related information that is user-specific including, as non-limiting examples, synchronous information obtained from the user and that corresponds to information in a ballistocardiogram (BCG) and an impedance plethysmography (IPG) measurements. By ensuring that the user, for whom such data was obtained, matches other bio-metric data as obtained concurrently for the same user, medical (and security) personnel can then assess, diagnose and/or identify with high degrees of confidence and accuracy.

In various related aspects, the scale and external circuitry provide various additional health information to the user in response various user inputs and/or the user data. The additional health information, in various embodiments, includes tables, information, and/or correlates to the cardio-related information that is determined using the external circuitry (e.g., physiologic parameters) and is non-RX health information. In various embodiments, the cardio-related information may indicate the user has and/or is at risk for a disorder, disease, and/or has a particular symptom. The additional health information is provided to the user that includes generic information for the disorder, disease, and/or particular symptom without specific information about the user and/or an indication that the user has and/or is at risk for the disorder, disease, and/or symptom. In a number of embodiments, the generic information is based on and/or correlated to specific user inputs, such as a category of interest (e.g., demographic of interest, disorder/disease of interest), among other inputs. For example, while, after and/or before taking the various impedance measurements, the user is asked a number of questions. The scale can display the questions, ask the questions using a natural language interface (e.g., a speaker component of the device asks the user questions using computer generated sounds). In some embodiments, the scale instructs another user circuitry, such as a user device (e.g., cell phone, tablet, computing device, smart watch) to ask the questions, and in response to the user's input, the user device provides the responses to the scale and/or the external circuitry. Based on the inputs, categories of interest for the user are determined and used to generate the additional health information.

As used herein, a user device includes processing circuitry and output circuitry to collect various data (e.g., signals) and communicate the data to the scale and/or other circuitry. Example user devices include cellphones, tablets, standalone server, among other devices. The user device can be a wearable device that is worn by a user, such as on a user's wrist, head, or chest. Example wearable devices include smartwatches and fitness bands, smart glasses, chest heart monitors, etc. In other aspects, the user device further includes sensor circuitry or other circuit to collect physiologic data from the user, and, can optionally be in secured communication with the scale or other circuitry. For example, the user device includes smartwatches or fitness bands that collect heart rate and/or ECG and/or body temperature, medical devices, implanted medical devices, smart beds, among other devices. Example physiologic data collected by user devices includes glucose measurements, blood pressure, ECG or other cardio-related data, body temperature, among other data. The terms "user device" and "wearable device", can be interchangeably used.

In a number of a specific embodiments, the user stands on the scale. The scale collects signals using the data-procurement circuitry, and sends at least a portions of the signals to the external circuitry. The external circuitry processes the collected signals, sent as user data, and determines cardio-related information, which may include Rx information. During the processing by the external circuitry, the scale (and/or a user device) asks the user if the user is interested in receiving various health information and/or would like a table provided that is based on various demographics, disorders, and/or other categories of interest. In response to the user providing an input indicating they are interested, the scale asks the user to input categories of interest (demographics, disorders, symptoms, etc.). In some embodiments, the scale provides the inputs to the external circuitry and the external circuitry derives additional health information using the inputs and the user data. For example, the external circuitry can determine health information that is based on the demographics the user provides (e.g., particular sex, age, ethnicity) and various values and/or symptoms of a disorder/disease/symptom correlated to the cardio-related information of the user. As a particular specific example, the user can provide that they are interested in a table for males, 45-55, and African-American. The user data may indicate that the user has and/or is at risk for atrial fibrillation. In various embodiments, the external circuitry generates a table which includes general risk factors and/or symptoms for various heart-related conditions, which includes atrial fibrillation, for African-American males ages 45-55. The information provided does not include particular values for the user and/or any indication that the user has atrial fibrillation. In this manner, the scale does not provide Rx health information without a prescription from a physician and can be provided over-the-counter.

Turning now to the figures, FIG. 1a shows an apparatus consistent with aspects of the present disclosure. The apparatus includes a platform 101 and a user display 102. The user, as illustrated by FIG. 1a is standing on the platform 101 of the apparatus. The user display 102 is arranged with the platform 101. As illustrated by the dotted lines of FIG. 1a, the apparatus further includes processing circuitry 104, data-procurement circuitry 138, and physiologic sensors 108. That is, the dotted lines illustrate a closer view of components of the apparatus.

The physiologic sensors 108, in various embodiments, include a plurality of electrodes integrated with the platform 101. The electrodes and corresponding force-sensor circuitry 139 are configured to engage the user with electrical signals and to collect signals indicative of the user's identity and cardio-physiological measurements while the user is standing on the platform 101. For example, the signals are indicative of physiologic parameters of the user and/or are indicative of or include physiologic data, such as data indicative of a BCG or ECG and/or actual body weight or heart rate data, among other data. Although the embodiment of FIG. 1a illustrates the force sensor circuitry 139 as separate from the physiological sensors 108, one of skill in the art may appreciate that the force sensor circuitry 139 are physiological sensors. The user display 102 is arranged with the platform 101 and the electrodes to output user-specific information for the user while the user is standing on the platform 101. The processing circuitry 104 includes CPU and a memory circuit with user-corresponding data 103 stored in the memory circuit. The processing circuitry 104 is arranged under the platform 101 upon which the user stands, and is electrically integrated with the force-sensor circuitry 139 and the plurality of electrodes (e.g., the physiologic sensors 108). The data indicative of the identity of the user includes, in various embodiments, user-corresponding data, biometric data obtained using the electrodes and/or force sensor circuitry, voice recognition data, images of the user, input from a user's device, and/or a combination thereof and as discussed in further detail herein. For example, the scale can capture voice sounds from the user speaking, and the user data indicative of the identity includes the voice sounds captured.

The user-corresponding data includes information about the user that may or may not be obtained using the physiologic sensors 108, such as demographic information or historical information. Example user-corresponding data includes height, gender, age, ethnicity, exercise habits, eating habits, cholesterol levels, previous health conditions or treatments, family medical history, and/or a historical record of variations in one or more of the listed data. The user-corresponding data can be obtained directly from the user (e.g., the user inputs to the scale) and/or from another circuit (e.g., a smart device, such a cellular telephone, smart watch and/or fitness device, cloud system, etc.).

In various embodiments, the processing circuitry 104 is electrically integrated with the force-sensor circuitry 139 and the plurality of electrodes and configured to process data obtained by the data-procurement circuitry 138 while the user is standing on the platform 101. The processing circuitry 104, for example, generates cardio-related physiologic data corresponding to the collected signals and that is manifested as user data. Further, the processing circuitry 104 generates data indicative of the identity of the user, such as a user ID and/or other user identification metadata. The user ID can be, for example, in response to confirming identification of the user using the collected signals indicative of the user's identity.

The user data, in some embodiments, includes the raw signals, bodyweight, body mass index, heart rate, body-fat percentage, cardiovascular age, among other data. In various embodiments, the processing circuitry 104, with the user display 102, displays at least a portion of the user data to the user. For example, user data that is not-regulated is displayed to the user, such as user weight. Alternatively and/or in addition, the user data is stored. For example, the user data is stored on the memory circuit of the processing circuitry (e.g., such as the physiologic data stored on the physiological user data database 107 illustrated by FIG. 1a). The processing circuitry 104, in various embodiments, correlates the collected user data (e.g., physiologic user-data) with user-corresponding data, such as storing identification metadata that identifies the user with the respective data. An algorithm to determine the physiologic data from raw signals can be located on the scale, on another device (e.g., external circuitry, cellphone), and on a Cloud system. For example, the Cloud system can learn to optimize the determination and program the scale to subsequently perform the determination locally. The Cloud system can perform the optimization and programming for each user of the scale.

In some embodiments, the scale collects physiologic data from other devices, such as medical devices, user devices, wearable devices, and/or remote-physiological devices. The data can include glucose measurements, blood pressure, ECG or other cardio-related data, body temperature, among other physiologic data. Further, the scale can act as a hub to collect data from a variety of sources. The sources includes the above-noted user devices. The scale can incorporate a web server (URL) that allows secure, remote access to the collected data. For example, the secure access can be used to provide further analysis and/or services to the user.

In a number of embodiments, the processing circuitry 104 and/or the scale include an output circuit 106. The output circuit 106 receives the user data and, in response, sends the user data, including the data indicative of the user's identity and the generated cardio-related physiologic data, from the scale for reception at a remote location (e.g., to external circuitry 111 for assessment). In various embodiments, the output circuit 106. In various embodiments, the output circuit 106 provides data to user via a user interface. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101.

A user interface includes or refers to interactive components of a device (e.g., the scale) and circuitry configured to allow interaction of a user with the scale (e.g., hardware input/output components, such as a screen, speaker components, keyboard, touchscreen, etc., and circuitry to process the inputs). A user display includes an output surface (e.g., screen) that shows text and/or graphical images as an output from a device to a user (e.g., cathode ray tube, liquid crystal display, light-emitting diode, organic light-emitting diode, gas plasma, touch screens, etc.) For example, output circuit can provide data for display on the user display 102 the user's weight and the data indicative of the user's identity and/or the generated cardio-related physiologic data corresponding the collected signals. The external circuitry 111 is at a remote location from the scale and is not integrated with the scale. The communication, in various embodiments, includes a wireless communication and/or utilizes a cloud system.

The user interface is or includes a graphical user interface (GUI), a foot-controlled user interface (FUI), and/or voice input/output circuitry. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101. Example user interfaces include input/output devices, such as display screens, touch screens, microphones, etc.

A FUI is a user interface that allows for the user to interact with the scale via inputs using their foot and/or via graphic icons or visual indicators near the user's foot while standing on the platform. In specific aspects, the FUI receives inputs from the user's foot (e.g., via the platform) to allow the user to interact with the scale. The user interaction includes the user moving their foot relative to the FUI, the user contacting a specific portion of the user display, etc.

A GUI is a user interface that allows the user to interact with the scale through graphical icons and visual indicators. As an example, the external circuitry includes a GUI, processing circuitry, and output circuitry to communicate with the processing circuitry of the scale. The communication can include a wireless or wired communication. Example external circuitry can include a wired or wireless tablet, a cellphone (e.g., with an application), a smartwatch or fitness band, smartglasses, a laptop computer, among other devices. In other examples, the scale includes a GUI and voice input/output circuitry (as further described below) integrated in the platform 101. The user interact with the scale via graphical icons and visual indicators provided via the GUI and voice commands from the user to the scale.

Voice input/output circuitry (also sometimes referred to as speech input/output) can include a speaker, a microphone, processing circuitry, and other optional circuitry. The speaker outputs computer-generated speech (e.g., synthetic speech, instructions, messages) and/or other sounds (e.g., alerts, noise, recordings, etc.) The computer-generated speech can be predetermined, such as recorded messages, and/or can be based on a text-to-speech synthesis that generates speech from computer data. The microphone captures audio, such a voice commands from the user and produces a computer-readable signal from the audio. For example, the voice input/output circuitry can include an analog-to-digital converter (ADC) that translates the analog waves captured by the microphone (from voice sounds) to digital data. The digital data can be filtered using filter circuitry to remove unwanted noise and/or normalize the captured audio. The processing circuitry (which can include or be a component of the processing circuitry 104) translates the digital data to computer commands using various speech recognition techniques (e.g., pattern matching, pattern and feature matching, language modeling and statistical analysis, and artificial neural networks, among other techniques).

The external circuitry 111 receives the user-data, validates the user data as concerning a specific user associated with a user ID, and determines at least one physiologic parameter of the user using the user data. As discussed in further detail herein, the validation can be based on the data indicative of the user's identity. For example, the data indicative of the user's identity can be the user ID and/or can be associated with the user ID (e.g., is mapped to and/or otherwise correlated to). The external circuitry 111, in some embodiments, communicates the determined physiologic parameter back to the scale and/or another user device for display to the user. Alternatively and/or in addition, the external circuitry controls access to the physiologic parameter, as discussed further herein.

The physiologic parameter, in various embodiments, includes PWV, BCG, cardiac output, pre-ejection period, stroke volume, arterial stiffness, respiration, and/or other Rx health information. The user data, in some embodiments, includes the raw force signals, bodyweight, heartrate, balance, tremors, body mass index and/or percentage, among other non-regulated physiologic data.

Although the present examples embodiments provided above are in reference to external circuitry performing the determination, embodiments in accordance with the present disclosure are not so limited. For example, the processing circuitry 104 can determine the physiologic parameter while the user is standing on the platform 101.

In accordance with various embodiments, although not illustrated by FIG. 1*a*, the apparatus includes an additional sensor circuitry that is external to the scale. The additional sensor circuitry can include a communication circuit and is configured and arranged to engage the user with electrical signals and collect therefrom signals indicative of an ECG of the user. The sensor circuitry, which may include and/or be correlated with processing circuitry configured to derive an ECG from the collected signals. The sensor circuitry communicates the ECG to the external circuitry 111 and the scale can communicate a BCG to the external circuitry 111.

Figure 1B:
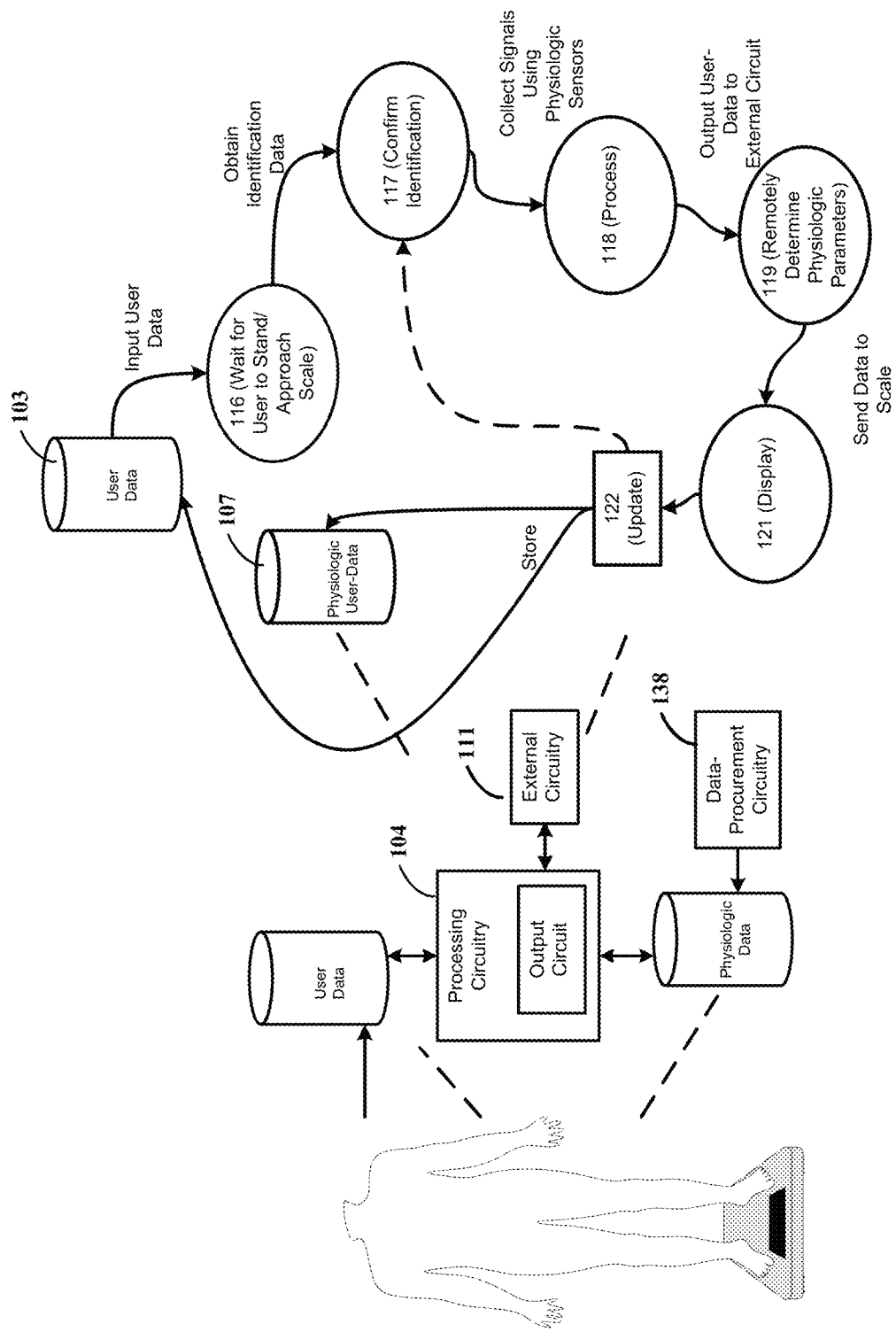
FIG. 1b shows an example of remotely determining physiologic parameters using an apparatus consistent with aspects of the present disclosure.

FIG. 1*b* shows an example of remotely determining physiologic parameters using an apparatus consistent with aspects of the present disclosure. The apparatus illustrated by FIG. 1*b* can include the apparatus, including the platform 101 and user display 102, as previously illustrated and discussed with regard to FIG. 1*a*. As illustrated, the apparatus includes a platform, a user display configured and arranged with the platform and the plurality of electrodes to output user-specific information for the user while the user is standing on the platform, data-procurement circuitry 138, and processing circuitry 104. The data-procurement circuitry 138 includes force-sensor circuitry and a plurality of electrodes (e.g., the physiologic sensors 108) which are integrated with the data-procurement circuitry 138. The processing circuitry 104 includes a CPU and a memory circuit with user-corresponding data stored in the memory circuit. As previously discussed, the scale includes an output circuit to send the user data to external circuitry 111. The external circuitry 111 can receive the user-data and determine the physiologic parameters of the user using the user data.

For example, as illustrated by FIG. 1*b*, the scale at block 116 waits for a user to stand on the platform. User-corresponding data 103 is input and/or received prior to the user standing on the scale and/or in response to. In various embodiments, in response to the user standing on and/or approaching the scale, the apparatus obtains identification data to identify the user. Example identification data, as discuss further herein with regard to FIG. 2*a*, includes the time of day, length of foot, spoken words from the user, weight, height, facial features, etc. At block 117, the apparatus, using the processing circuitry 104, confirms identification of the user when the user is standing on the platform and/or as the user approaches the platform. The identification, in various embodiments, is based on the identification data and/or user data. For example, the processing circuitry 104 compares the identification data to stored user-corresponding data 103 to confirm identification of the user. Further, in some embodiments, additional user-corresponding data is obtained in response to the user standing on and/or approaching the platform.

In response to the user standing on the scale, the scale collects signals indicative of cardio-physiological measurements (e.g., force signals). The processing circuitry 104, at block 118, processes the signals to generate cardio-related physiologic data manifested as user data and outputs the user data to the external circuitry 111. In various embodiments, the processing includes adding (and later storing) data with a time stamp indicating a time at about when the physiologic parameter data is obtained.

The external circuitry 111, at block 119, receives the user data, validates the user data as corresponding to the user using the user ID, and determines at least one physiologic parameter using the user-data. Example physiologic parameters includes PWV, BCG, respiration, arterial stiffness, cardiac output, pre-ejection period, stroke volume, and a combination thereof. The external circuitry 111 then outputs the physiologic parameter. The output can be to the scale for display, such as illustrated at block 121 and/or to a memory circuit corresponding to the external circuitry 111 (e.g., as illustrated with regard to FIG. 1*c*-1*e*). The scale, in various embodiments, updates the stored user-corresponding data 103 and/physiologic user data 107 of the user as stored on the memory circuit of the processing circuitry 104 of the scale.

In accordance with a number of embodiments, the scale including the processing circuitry provides a number of questions to the user. The questions can be provided via a speaker component of the scale outputting computer generated natural voice (via a natural language interface), displaying the questions on the user display 102, and/or outputting the questions to another user-device. In various embodiments, the questions include asking the user if the user is interested in additional health information and if the user has particular categories of interest. In various embodiments, the categories of interest include a set of demographics, disorders, diseases, and/or symptom that the user is interested, and/or other topics. The scale provides the input to the external circuitry 111 and the external circuitry 111 derives the additional health information for the user. The additional health information can include a table that corresponds to the categories of interest and/or corresponds to the physiologic parameter and/or clinical indications determined without providing any specific values and/or indication related to the physiologic parameter. The user is provided the additional health information by the external circuitry 111 outputting the information to the scale and/or another user-device, and the scale and/or other user-device displays the information. In various embodiments, the information can be printed by the user to bring to a physician. In various related-aspects, the scale using the processing circuitry 104 generates the additional health information instead of the external circuitry 111. As previously described, the scale can (alternatively and/or in addition to a FUI or GUI) have a voice input/output circuitry that can obtain be used obtain the categories of interest from the user via voice comments and inputs user information in response (e.g., a speaker component to capture voice sounds from the user and processing circuitry to recognize the voice commands and/or speech).

The additional health information is generated, in various embodiments, by comparing and/or correlating the categories of interest to raw data obtained by the data-procurement circuitry 138. In various embodiments, the correlation/comparison include comparing statistical data of a sample census pertinent to the categories of interest and the at least one physiologic parameter. The statistical data of a sample census includes data of other users that are correlated to the categories of interest. In such instances, the additional health information can include a comparison of data measured while the user is standing on the platform to sample census data (e.g., may contain Rx information). In other related embodiments, the correlation/comparison includes comparing statistical data of a sample census pertinent to the categories of interest and values of the least one physiologic parameter of the sample census. In such instances, the additional health information includes average physiologic parameter values of the sample census that is set by the user, via the categories of interest, and may not include actual values corresponding to the user (e.g., does not contain Rx information).

For example, if the categories of interest are demographic categories, the additional health information can include various physiologic parameter values of average users in the demographic categories and/or values of average users with a clinical indication that correlates to a physiologic parameter of the user. Alternatively and/or in addition, the additional health information can include general medical insights related to the categories of interest. For example, "Did you know if you are over the age of 55 and have gained 15 pounds, you are at risk for a particular disease/disorder?" The scale can ask the user if the user would like to include this factor or disease in their categories of interest to dynamically update the categories of interest of the user.

Various categories of interest, in accordance with the present disclosure, include demographics of the user, disorders, diseases, symptoms, prescription or non-prescription drugs, treatments, past medical history, family medical history, genetics, life style (e.g., exercise habits, eating habits, work environment), among other categories and combinations thereof. In a number of embodiments, various physiological factors can be an indicator for a disease and/or disorder. For example, an increase in weight, along with other factors, can indicate an increased risk of atrial fibrillation. Further, atrial fibrillation is more common in men. However, symptoms of various disorders or disease can be different depending on categories of interest (e.g., atrial fibrillation symptoms can be different between men and women). For example, in women, systolic blood pressure is associated with atrial fibrillation. In other instances, sleep apnea may be assessed via an ECG and can be correlated to weight of the user. Furthermore, various cardiac conditions can be assessed using an ECG. For example, atrial fibrillation (AFIB) can be characterized and/or identified in response to a user having indistinguishable or fibrillating p-waves, and indistinguishable baseline/inconsistent beat fluctuations. Atrial flutter, by contrast, can be characterized by having indistinguishable p-wave, variable heart rate, having QRS complexes, and a generally regular rhythm. Ventricular tachycardia (VT) can be characterized by a rate of greater than 120 beats per minute, and short or broad QRS complexes (depending on the type of VT). Atrio-Ventricular (AV) block can be characterized by PR intervals that are greater than normal (e.g., a normal range for an adult is generally 0.12 to 0.20 seconds), normal-waves, QRS complexes can be normal or prolong shaped, and the pulse can be regular (but slow at 20-40 beats per minute). For more specific and general information regarding atrial fibrillation and sleep apnea, reference is made herein to https://www.clevelandclinicmeded.com/medicalpubs/diseasemanagement/cardiology/atrial-fibrillation/and http://circ.ahajournals.org/content/118/10/1080.full, which are fully incorporated herein for their specific and general teachings. Further, other data and demographics that are known and/or are developed can be added and used to derive additional health information.

For example, the categories of interest for a particular user can include a change in weight, age 45-55, and female. The scale obtains raw data using the data-procurement circuitry 138 and the categories of interest from the user. The scale outputs the raw data and categories of interest to the external circuitry 111 and the external circuitry 111 correlates the categories of interest to the raw data and derives additional health information therefrom. Further, the external circuitry 111, over time, historically collects and correlates the categories of interest of the user and data from the data-procurement circuitry. The external circuitry 111, in various embodiments, sends the data to a physician and/or additional health information to the user (to print and/or otherwise view).

In various embodiments, the external circuitry controls access to the least one physiologic parameter. For example, the external circuitry 111 can allow access to the at least one physiologic parameter to a physician corresponding with the user and/or not allow access to the at least one physiologic parameter to the user. The user can be granted access, for instance, in response to a prescription provided by the physician. For example, the user data can be collected and determined but the user is not allowed access to the features, such as access to the user data or service related to the user data until government clearance is obtained. For example, the scale collects and stores the user data but does not display or otherwise allow the user access to the user data until clearance is obtained for each feature, which retrospectively enables the feature and/or service. Alternatively and/or in addition, the feature and/or service is not provided until a weighted value is received (e.g., payment).

In a number of embodiments, the external circuitry 111 determines additional physiologic parameters and/or data, such as further clinical indications, of the user using the determined physiologic parameter. For example, the determined physiologic parameter can include an ECG and the external circuitry 111 can determine a BCG using the ECG. Alternatively and/or in addition, the external circuitry 111 can determine a health status of the user using the determined physiologic parameter, such as a condition or treatment.

The scale can be used by multiple different users. A subset or each of the different users can have data output to external circuitry and can receive additional health data, related to different categories of interest. For example, each of a plurality of users have previously or current entered different categories of interest. The scale can store an indication of the categories of interest and as associated with each respect user. The scale and/or external circuitry can selectively track particular data based on the different categories of interest and provide the additional health data, which can be updated over time, responsive to recognizing a particular user.

The scale can be used in different settings and/or modes, such as a consumer mode, a professional mode, and a combination mode. A consumer mode includes a scale as used and/or operated in a consumer setting, such as a dwelling. As a specific example, a scale is located in a dwelling with five different people. Each of the five different people use the scale, and three of the five people have previously provided inputs to the scale that indicate different categories of interest. Prior to providing additional health information to a user, the identity of the respective user is verified via the scale using a scale-based biometric. Responsive to identifying the user, the scale identifies the particular categories of interest corresponding to the user, outputs all or portions of the data to the external circuitry. The external circuitry generates the additional health information based on the categories of interest and the user data, and outputs the same to the scale to provide to the user. As users in a consumer mode may be familiar with one another (e.g., live together), the identification of the user by the scale can be based on weight, body-mass-index, and/or other data. Although embodiments are not so limited and the identification can be based on other biometrics and/or passcodes.

In other instances, the scale is used in a professional setting, such as a medical office, and/or in a professional mode. A professional mode includes an operation of the scale as used and/or operated in a professional setting, such as a doctor's office, exercise facility, nursing home, etc. In a professional mode, the scale is used by different users that may not be familiar with one another. The different users may have services with the professional to track and/or aggregate data from a peripheral device and/or to provide health information. A peripheral device includes or refers to circuitry that is not integrated within the scale and can communicate with the scale via a wired or wireless connection. In some instances, a user can be provided additional health information as service while waiting for the professional, such as while waiting to see a doctor. The scale receives the additional health information from the external circuitry and either displays the additional health information using a user interface of the scale and/or via direct communication (e.g., WiFi, Bluetooth, NFC) with a user device (e.g., cellphone, tablet) that is within a threshold distance of the scale. Similar to the consumer mode, the scale can selectively provide the services by verifying the identity of the user using a scale-based biometric. The identification can include a higher-level biometric and/or identification than the consumer mode. As a specific professional mode example, a scale is located at a doctor's office and is used to obtain data from multiple patients (e.g., 10 in a day, 500 in a year). When a patient checks-in, they stand on the scale and the scale-obtained data is output to external circuitry for document retention and/or other purposes. A subset (or all) of the patients have activated a service with doctor that corresponds with and/or includes providing additional health information while the user is waiting and/or based on categories of interest. For example, a user indicates an interest in learning more about AFIB, which the scale outputs to external circuitry along with user data obtained by the scale. The external circuitry generates additional health information correlated with AFIB and the user data. For example, the additional health information includes various risks factors for AFIB and identifies lifestyle changes that can reduce the risk factors. The external circuitry communicates the additional health information to the scale via an Internet (or direct communication) connection and the scale outputs the additional health information to a cellphone of the user via an NFC or Bluetooth communication. The scale, in the professional mode, may be used to obtain data from more users than a scale used in a consumer setting.

The scale can also be in a combination consumer/professional mode. A combination consumer/professional mode includes a scale as used and/or operated in a consumer setting for purposes and/or uses by a professional, and/or in a professional setting for purposes and/or uses by the consumer (e.g., use by the consumer outside of the professional setting and/or in addition to). As a specific example, a scale is located at a user's dwelling and used by multiple family members. A first user of the family is diagnosed with a heart-related condition and the doctor may offer a service to review data from the scale (and optionally another user device) of the first user. When the other family members stand on the scale, the scale operates in the consumer mode. The other family members may or may not have the service activated for the doctor to review data and the scale operates via the consumer mode. When the first user that is diagnosed with heart-related condition stands on the scale, the scale recognizes the user and operates in a professional mode or a combination mode. For example, the scale outputs aggregated data from the scale to external circuitry that is accessible by the doctor of the first user.

Data provided to the user and/or the professional can default to be displayed on the user interface of the scale, the GUI of the user device, and/or a GUI of other external circuitry depending on the use of the scale. In a consumer mode and/or combination consumer/professional mode, data can default to display on the user interface of the scale. The defaulted display of data can be revised by the user providing inputs to display the data on the GUI of a user device or a GUI of another external circuitry (e.g., a standalone CPU) and/or automatically by the scale based on past scale-based actions of the user. As a specific example, a first user provided a user input to the scale to display data on the GUI of the user device multiple times (e.g., more than a threshold number of times, such as five times). In response, the scale adjusts the defaulted display and output data to the GUI of the user device. The display on the user interface of the scale and/or GUI of the user device (or other external circuitry) can include an indication of available additional health information, requests for categories of interest, and/or the additional health information, among other displays. In a professional mode, the scale is not owned by the user. The user may be uninterested in synchronizing their user device with the professional's scale. The display may default to the GUI of the user device to display an option to synchronize, and/or to override the synchrony. Alternatively, the display may default to the user interface of the scale to display an option to synchronize and, responsive to user verification or authority to synchronize, defaults to display on the GUI of the user device. During the combination consumer/professional mode, portions of scale-obtained data for a particular user may default to display on external circuitry, such as a standalone or server CPU that is accessible by the professional.

Figure 1C:
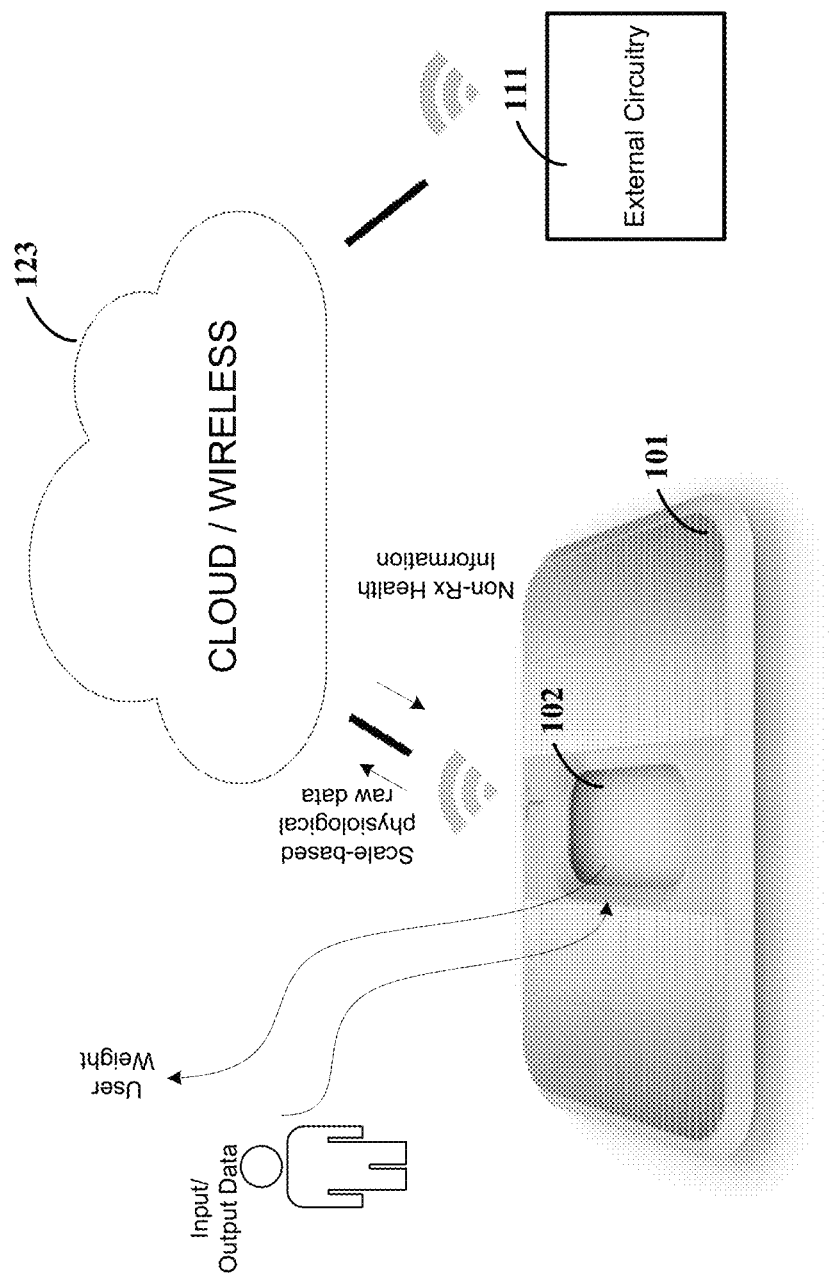
FIG. 1c shows an example of a scale wireless communicating with external circuitry consistent with aspects of the present disclosure.

FIG. 1c shows an example of a scale wireless communicating with external circuitry consistent with aspects of the present disclosure. The scale is configured to monitor signals and/or data indicative of physiologic parameters of the user while the user is standing on the platform 101 and communicate the signals and/or data to the external circuitry 111.

As discussed above, a scale in various embodiments includes a platform 101, a user display 102, processing circuitry 104 include a plurality of electrodes, and output circuitry. The output circuitry is configured and arranged to send user data to the external circuitry 111 for assessment at a remote location. The external circuitry 111 is not integrated within the scale. The scale communicates user data wirelessly (and/or via the cloud 123) to and from the external circuitry 111. For example, the external circuitry 111 can determine at least one physiologic parameter. In some embodiments, the external circuitry 111 optionally controls access to the physiologic parameter by storing the parameter in a database corresponding with and/or integrated with the external circuitry 111. Alternatively and/or in addition (such as, in response to determining the user can access the parameter) the external circuitry 111 outputs the physiologic parameter to the scale for display and/or storage.

In various embodiments, the scale outputs user input data that provides an indication that the user is interested in additional health information and various categories of interest. As previously discussed, the categories of interest can include demographics of interest, symptoms of interest, disorders of interest, diseases of interest, drugs of interest, treatments of interest, etc. The additional health information can be derived by the external circuitry 111 and provided to the scale that correlates to the category of interest and a physiologic parameter of the user.

For example, as illustrated by FIG. 1*c*, the user provides user input/outputs to the scale. The inputs/outputs include the categories of interest. The scale obtains signals using the data-procurement circuitry and outputs user-weight to the user. Further, the scale outputs scale-based physiological raw data (e.g., the collected signals manifested as user data indicative of the user's identity and cardio-physiological measurements). As illustrated, the output can include a wireless communication to the external circuitry 111 using a cloud system 123. The external circuitry 111 validates the raw data as concerning a specific user and determines at least one physiologic parameter. In various embodiments, the external circuitry 111 determines clinical indications of the user. Further, the external circuitry 111 generates additional health information by correlating the raw data with the categories of interest and outputs the additional health information. For example, the external circuitry 111 outputs the addition health information to the scale and/or another user circuitry using the cloud system 123 and/or another wireless communication.

The external circuitry 111, in various embodiments, validates the received user data as corresponding to a particular user and correlates the received user data with a profile of the user based on identification metadata within the received user data and/or based on identification of the user using the user data. For example, in some embodiments, the processing circuitry of the scale correlates the user-corresponding data with the user data such that the user data includes identification metadata. The external circuitry 111 then identifies the user, validates the user data as corresponding to the user, and identifies the profile corresponding to the user using the identification metadata within the user data. The profile, in various embodiments, is a user health profile, such as a medical history file.

In a number of embodiments, the external circuitry 111 provides (e.g., determines) one or more physiologic parameters by processing the user data, such as determining a physiologic parameter as discussed in further detail herein. The physiologic parameters can include PWV, BCG, respiration, arterial stiffness, cardiac output, pre-ejection period, stroke volume, diagnosis, conditions, and risk factors, among other health information. The external circuitry 111 provides the physiologic parameter, in some embodiments, by updating the profile of the user with the received user data and/or the physiologic parameter.

In various related embodiments, the external circuitry 111 determines additional health information and provides the additional health information to the scale for display to the user. The additional health information can be indicative of the physiologic parameter and can correlate to categories of interest provided by the user. The categories of interest can be provided at a different time, the same time and/or from the scale. In various embodiments, the additional health information is based on historical user data. For example, the additional health information (e.g., a table) provided can include a correlation to the category of interest and the user data over time.

In some embodiments, the external circuitry controls access to the user profile and/or the data. In some embodiments, the control of access includes allowing access to the physiologic parameter and the user data to a physician corresponding to the user for information. Further, the control includes not allowing access to the physiologic parameters to the user. In various embodiments, the user is allowed to access the user data in the profile and the scale can display portions of the user data and/or other non-regulated data. Additionally, the external circuitry 111 may not allow access to the profile and/or any data corresponding to the profile to non-qualified personal, such as other users. In various embodiments, the user is allowed access the physiologic parameter in response to interpretation by the physician and a prescription from the physician to access the physiologic parameter. Further, in some embodiments, a demographic model and/or other report is provided to the user in response to the physiologic parameter. For example, the user may not be allowed to view the physiologic parameter but is provided generic information corresponding to other users with similar physiologic parameter value.

The access is controlled, in various embodiments, using a verification process. For example, in response to verifying identification of the physician and/or the user, access to particular data can be provided. The verification can be based on a user sign in and password, a password, biometric data, etc., and/or identification of the user using the scale (in which, the relevant data is sent to the scale or another user device in response to the identification).

In various embodiments, the physiologic parameter is provided as an additional service. For example, the user can obtain the information and/or have their physician interpret the information for a service fee. The service fee can include a one-time fee for a single interpretation, a monthly or yearly service fee, and/or can be a portion of a health care insurance fee (e.g., the user can purchase a health care plan that includes the service). In such embodiments, the physician corresponding to the user can access the physiologic parameter and/or other user data in response to verification that the user has enabled the service and verification of the identity of the physician.

The remote processing and/or controlled access, for example, allows a physician corresponding with the data to access the physiologic parameter for interpretation. For example, the physician can give a prescription to the user to access all information in the user profile. In response to the prescription, the external circuitry 111 allows the user to access the physiologic parameter. Further, the physician can prescribe medicine to the user based on the profile and the external circuitry 111 can provide an indication to the user that a prescription for medicine is ready. The physician may provide instructions or further explanation for the user, which can be sent and displayed using the scale and/or another user-device. Such information can include life-style suggestions, explanation for how to use the prescribed medicine and/or why it is prescribed, and/or other advice, such as symptoms that the user should watch for. For instance, the physiologic parameter may suggest that the user has a heart condition and/or disorder. The physician may prescribe medicine to the user and/or provide potential symptoms that the user should watch for and/or should go to the physician's office or an emergency room if the symptoms arise. In this manner, the scale and controlled access to Rx health information is used to remotely monitor health of the user and/or provide physician services.

Figure 1D:
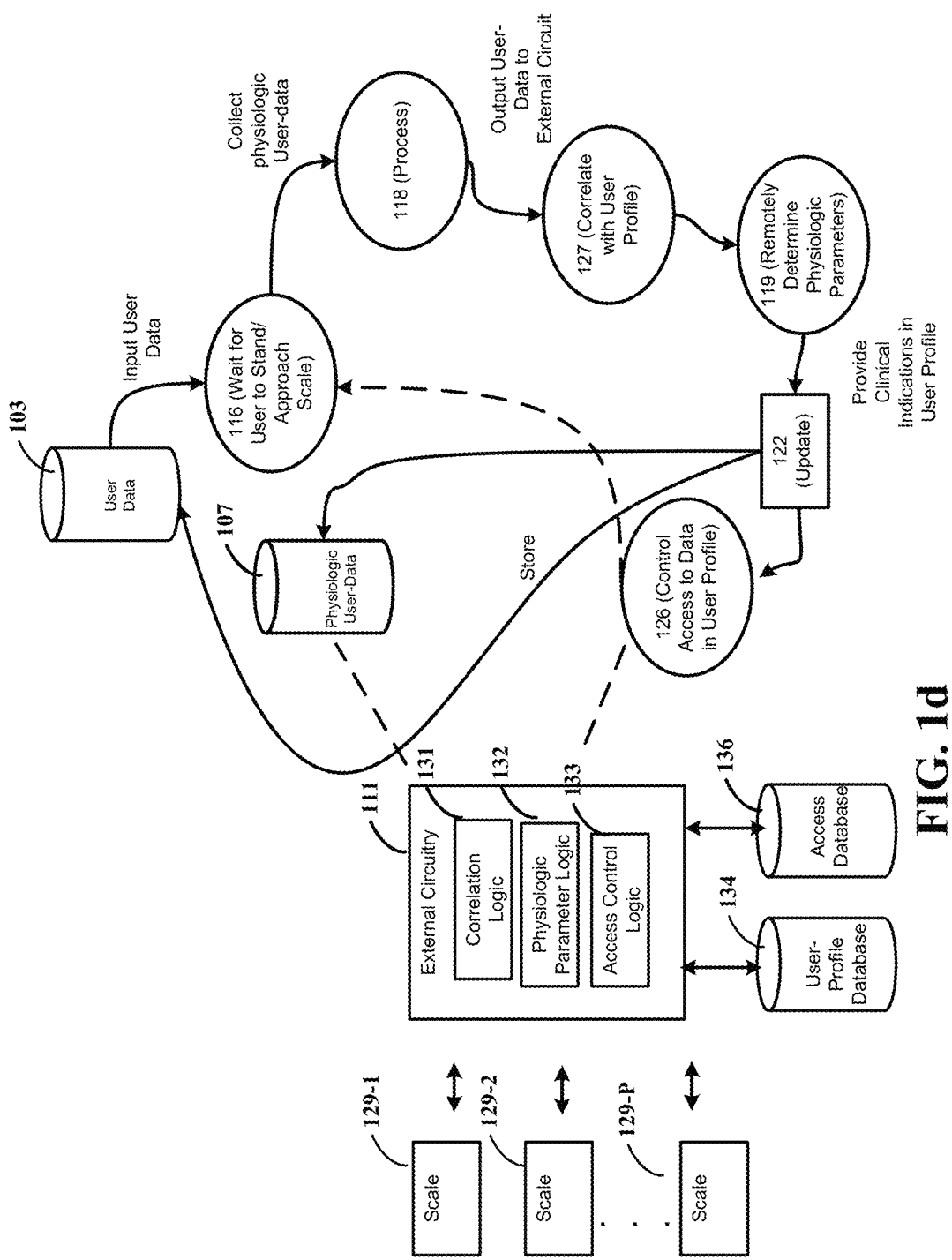
FIG. 1d shows an example of apparatus comprised of a plurality of scale and external circuitry consistent with aspects of the present disclosure.

In accordance with various embodiments, although not illustrated by FIG. 1d, the apparatus includes an additional sensor circuitry that is external to the scale. The additional sensor circuitry can include a communication circuit and is configured and arranged to engage the user with electrical signals and collect therefrom signals indicative of an ECG of the user. The sensor circuitry, which may include and/or be correlated with processing circuitry configured to derive an ECG from the collected signals. The sensor circuitry communicates the ECG to the external circuitry 111 and the scale can communicate a BCG to the external circuitry 111.

In various embodiments, as illustrated by FIG. 1d, the apparatus includes additional scales. For example, the external circuitry 111 can receive user data from a plurality of scales. In some embodiments, one or more of the scales are located at a physician's office, such as the physician corresponding with the user. The external circuitry 111 can receive user data from the scale located at the physician's office and can calibrate the user data from the scale at the physician's office with the user data from the scale corresponding the user. In this way, data obtained from both scales are relevant to one another.

FIG. 1d shows an example of apparatus including a plurality of scales and external circuitry consistent with aspects of the present disclosure. As illustrated, the apparatus includes a plurality of scales 129-1, 129-2 . . . 129-P (herein generally referred to as "the scales 129") and external circuitry 111. Each scale can include the scale, including the platform 101 and user display 102, as previously illustrated and discussed with regard to FIG. 1a. Thereby, each scale includes a platform, data-procurement circuitry 138 including force-sensor circuitry and plurality of electrodes which are integrated with the data-procurement circuitry 138, processing circuitry 104 to receive collected signals from the data-procurement circuitry 138 and, in response, derive and output user-data to the external circuitry 111. The processing circuitry 104 includes a CPU and a memory circuit with user-corresponding data stored in the memory circuit. The user-data, in various embodiments, is automatically sent from the scales 129 to the external circuitry 111.

In various embodiments, the apparatus is used to remotely determine physiologic parameters (e.g., Rx health information) of a plurality of users. The scales 129, for example, correspond to the plurality of users. For example, each scale at block 116 waits for a user to stand on the platform. User-corresponding data 103 is input and/or received prior to the user standing on the respective scale and/or in response to. In response to the user standing on the respective scale, the respective scale collects signals indicative of an identity of the user and cardio-physiological measurements (e.g., force signals). The processing circuitry, at block 118, processes the signals and, in response, derives and outputs user data to the external circuitry 111. For example, the processing circuitry of the scale, using the signals, derives and outputs user-data corresponding to a particular user to the external circuitry 111 for assessment at a remote location that is not integrated within the scale.

As illustrated, the external circuitry 111 is configured to correlate the user data with a specific user/user profile, determine physiologic parameters, and optionally control access to the physiologic parameters. In various embodiments, the external circuitry includes computer-readable instructions executed to perform the various functions. For example, as illustrated by FIG. 1d, the external circuitry includes correlation logic 131 to correlate the user data, physiologic parameter logic 132 to determine parameters, and access control logic 133 to control access, as described further herein.

The external circuitry 111 receives the user data that corresponds to the plurality users from the plurality of scales 129. The respective user data can be received at over-lapping times and/or separate times. In response to receiving the user data, the external circuitry 111, in various embodiments, identifies the respective plurality of users based on the user data and validates the user data as corresponding to the users and, at block 127, correlates the received user data with profiles of the respective plurality of users based on the identification of the users. In various embodiments, the users can be identified using identification metadata within the user data (e.g., user IDs). In a number of embodiments, at block 119, the external circuitry 111 provides (e.g., determines) the physiologic parameters by processing the user data. The external circuitry 111 provides the physiologic parameters, in some embodiments, by updating the profile of the user with the user data and/or the physiologic parameter (s) at block 122. Alternatively, in some embodiments, the physiologic parameter(s) are output to the respective scale.

In accordance with various embodiments, at block 126, the external circuitry optionally controls access to the user profile. The control of access can include allowing access to the physiologic parameter (e.g., a clinical indication) and the user-data to at least one physician corresponding to at least one of the plurality of users and for interpretation. Further, the control includes not allowing access to the physiologic parameter(s) to the plurality of users (e.g., without a prescription). In various embodiments, the users are allowed access to the user data in the profile and the scale can display portions of the user data and/or other non-regulated data. In various embodiments, a specific user among the plurality of users is allowed access to the physiologic parameter corresponding to the specific user in response to interpretation by a physician corresponding to the specific user and a prescription from the physician to access the physiologic parameter. Further, in some embodiments, a demographic model and/or other report is provided to one or more users in response to the physiologic parameter and/or categories of interest input by the user.

In various embodiments, the controlled access allows a physician corresponding with one or more of the users to access the physiologic parameter for interpretation. For example, the physician can give a prescription to the user to access all information in the user profile. In response to the prescription, the external circuitry 111 allows the user to access the physiologic parameter and/or outputs the physiologic parameter to the respective scale (and/or other user device) corresponding to the user for display. Further, the physician can prescribe medicine to the user based on the profile and the external circuitry 111 can provide an indication to the user that a prescription for medicine is ready. The physician may prescribe medicine to the user and/or provide potential symptoms that the user should watch for.

As such, and in accordance with various embodiments, the one or more scales 129 have the capability to send raw force signals using wireless communications and/or over the Internet. The raw force signals are sent to the external circuitry 111, which may be an online database, where advanced processing is performed using processing resources that may be more powerful than the scale. The external circuitry 111 processes the force signals to determine the physiologic parameters. The user may access the one or more the physiologic parameters corresponding to the user via a prescription from a physician and/or a prescription service. The service provider can, for example, allow the user's physician to access the physiologic parameter and other data for interpretation in response to the user paying a service fee. In response to the service fee, the physician can interpret the data and may prescribe access to the data, among other things. The external circuitry 111 and/or online database/site can track user data for a plurality of users and from a plurality of scales and can correlate the user data with a profile of the respective user (e.g., using the access database 136 containing correlations or permissions to user profiles and the user-profile data base 134 containing the user profiles and corresponding user data). The profile of the user can be updated over time. Access to each respective profile is controlled and only allowed to the user's physician. The user's physician can be identified upon establishing the profile with the service provider and/or upon initializing the scale. For example, the user can purchase a scale over the counter and not pay for the service. The scale and the service provider can track the relevant data over time and allow access in response to a fee. Alternatively, the service provider may discard the information (and not determine clinical indications) until the service is established by the user.

In various embodiments, the external circuitry 111 provides a table to the user that corresponds to the physiologic parameter and/or categories of interest. Such a table can include non-Rx health information. Alternatively, the table can include Rx health information provided to the user in response to a prescription from a corresponding physician.

The remaining figures illustrate various ways to collect the physiologic data from the user, electrode configurations, and alternative modes of the processing circuitry 104. For general and specific information regarding the collection of physiologic data, electrode configurations, and alternative modes, reference is made to U.S. patent application Ser. No. 14/338,266 filed on Oct. 7, 2015, which is hereby fully incorporated by references for its teachings.

Figure 1E:
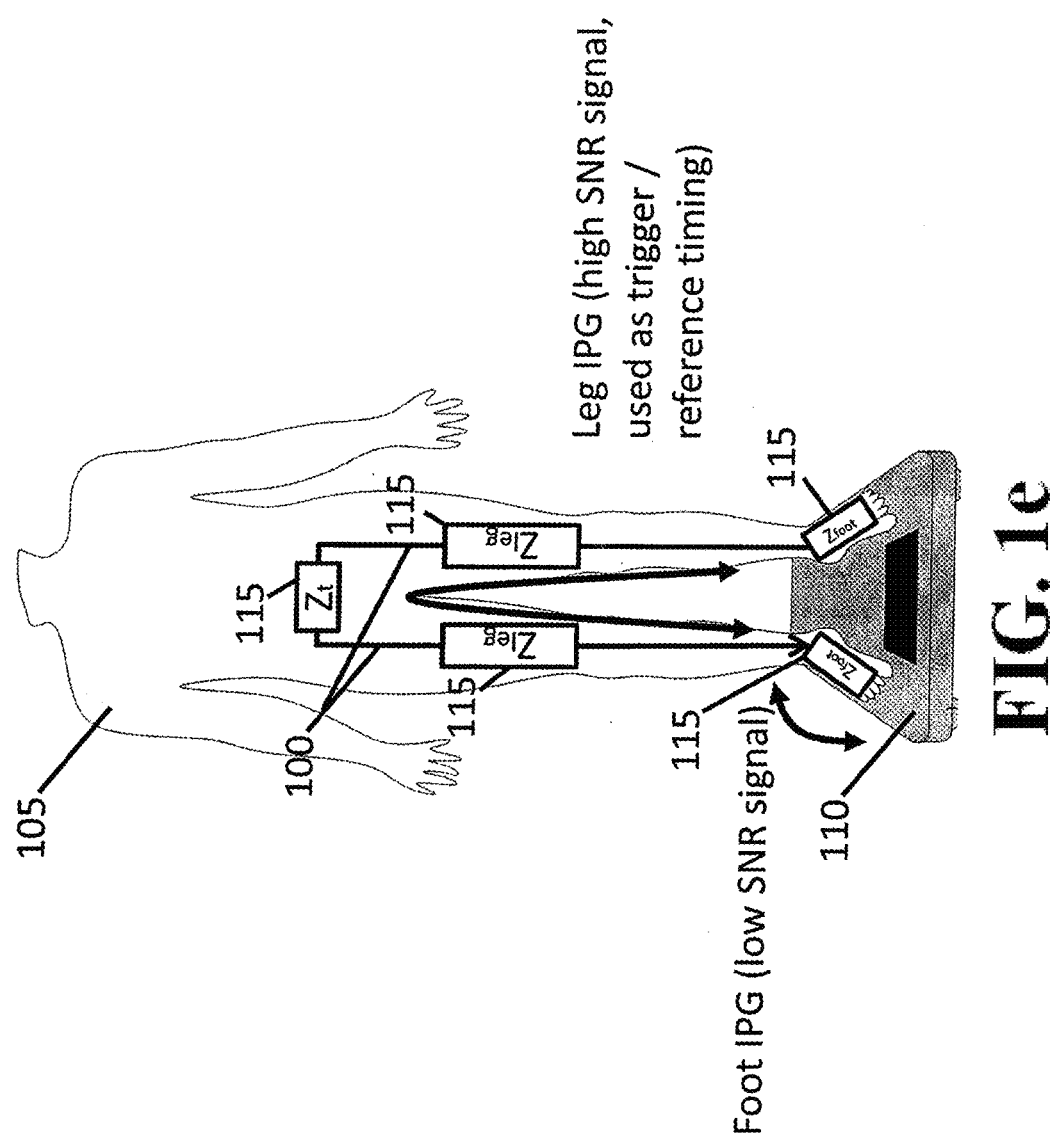
FIG. 1e shows current paths through the body for the IPG trigger pulse and Foot IPG, consistent with various aspects of the present disclosure.

FIG. 1e shows current paths 100 through the body of a user 105 standing on a scale 110 for the IPG trigger pulse and Foot IPG, consistent with various aspects of the present disclosure. Impedance measurements 115 are measured when the user 105 is standing and wearing coverings over the feet (e.g., socks or shoes), within the practical limitations of capacitive-based impedance sensing, with energy limits considered safe for human use. The measurements 115 can be made with non-clothing material placed between the user's bare feet and contact electrodes, such as thin films or sheets of plastic, glass, paper or wax paper, whereby the electrodes operate within energy limits considered safe for human use. The IPG measurements can be sensed in the presence of callouses on the user's feet that normally diminish the quality of the signal.

As shown in FIG. 1e, the user 105 is standing on a scale 110, where the tissues of the user's body will be modeled as a series of impedance elements, and where the time-varying impedance elements change in response to cardiovascular and non-cardiovascular movements of the user. ECG and IPG measurements sensed through the feet can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noise from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scales is also influenced by measurement time. The number of beats obtained from heartbeats for signal averaging is a function of measurement time and heart rate. Typically, a resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S. The following is an example SE for uncorrelated noise:

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for SNR improvements for the signal being averaged. Longer measurement times increase the number of beats lost to truncation, false missed triggering, and excessive motion. Longer measurement times also reduce variability from cardiorespiratory effects. If shorter measurement times (e.g., less than 30 seconds) are desired for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure oxygen availability and is often the limiting factor for cell survival. The heart normally pumps five to six liters of blood every minute during rest and maximum cardiac output during exercise increases up to seven-fold, by modulating heart rate and stroke volume. The factors that affect heart rate include autonomic innervation, fitness level, age and hormones. Factors affecting stroke volume include heart size, fitness level, contractility or pre-ejection period, ejection duration, preload or end-diastolic volume, afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracting the atria, the ventricles are filled with more blood and the depolarization then reaches the atrioventricular node and enters the ventricular side beginning the systole phase. The ventricles contract and the blood is pumped from the ventricles to arteries.

The ECG is the measurement of the heart's electrical activity and is described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as a timing reference for the cardiovascular cycle. Atrial repolarization is masked by the QRS complex. The ST interval represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases during the systole phase due to the high compliance (low stiffness) of the aortic wall. Blood traveling in the descending aorta bifurcates in the iliac branch which transitions into a stiffer arterial region due to the muscular artery composition of the leg arteries. The blood pulsation continues down the leg and foot. Along the way, the arteries branch into arteries of smaller diameter until reaching the capillary beds where the pulsatile blood flow turns into steady blood flow, delivering oxygen to the tissues. The blood returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot, result in a design that is insensitive to foot placement within the boundaries of the overall electrode area. As such, the user is not constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 1F:
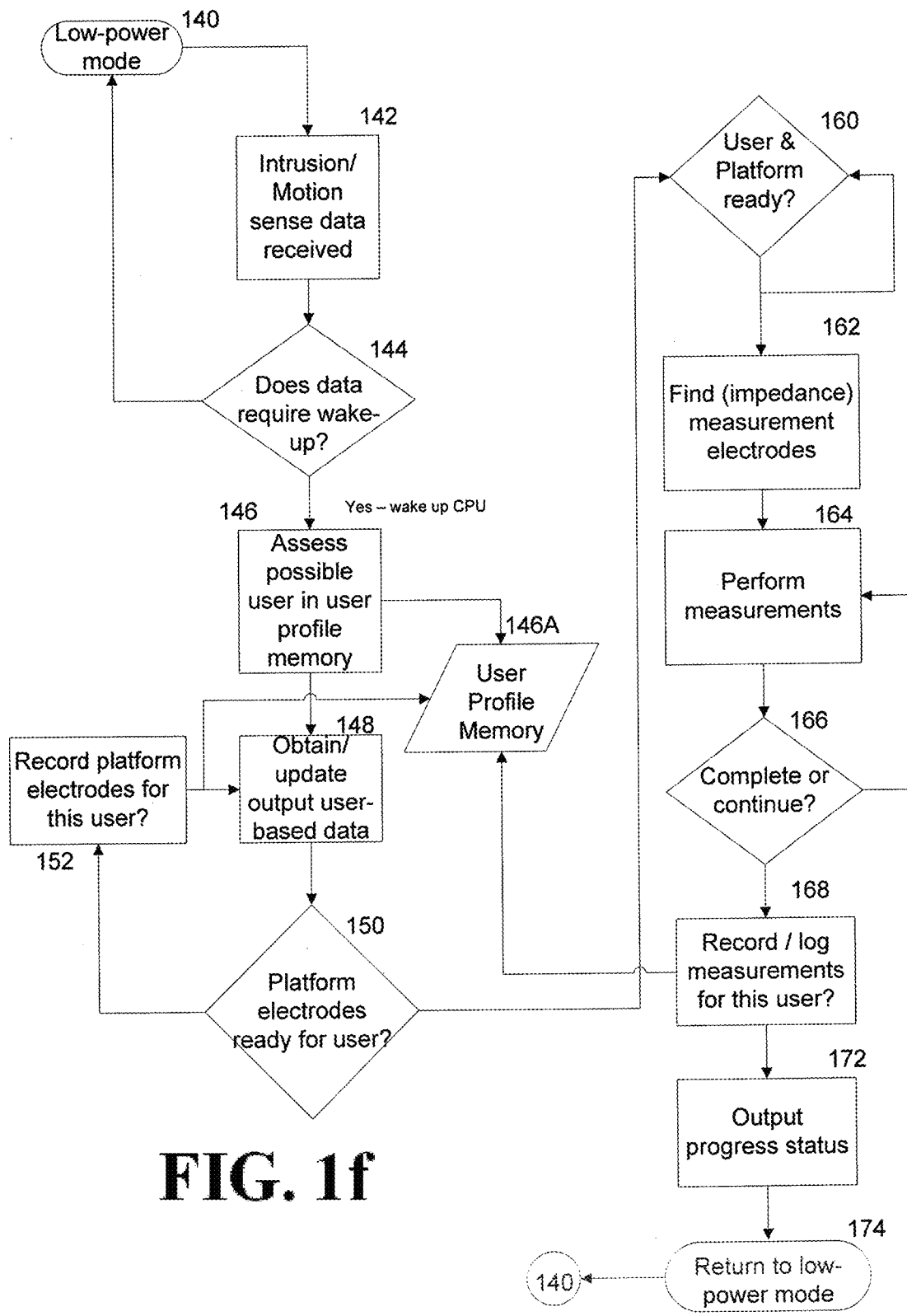
FIG. 1f is a flow chart illustrating an example manner in which a user-specific physiologic meter/scale may be programmed to provide features consistent with aspects of the present disclosure.

FIG. 1f is a flow chart depicting an example manner in which a user-specific physiologic meter or scale may be programmed in accordance with the present disclosure. This flow chart uses a computer processor circuit (or CPU) along with a memory circuit shown herein as user profile memory 146a. The CPU operates in a low-power consumption mode, which may be in off mode or a low-power sleep mode, and at least one other higher power consumption mode of operation. The CPU can be integrated with presence and/or motion sense circuits, such as a passive infrared (PIR) circuit and/or pyroelectric PIR circuit. In a typical application, the PIR circuit provides a constant flow of data indicative of amounts of radiation sensed in a field of view directed by the PIR circuit. For instance, the PIR circuit can be installed behind an upper surface which is transparent to infrared light (and/or other visible light) of the platform and installed at an angle so that the motion of the user approaching the platform apparatus is sensed. Radiation from the user, upon reaching a certain detectable level, wakes up the CPU which then transitions from the low-power mode, as depicted in block 140, to a regular mode of operation. Alternatively, the low-power mode of operation is transitioned from a response to another remote/wireless input used as a presence to awaken the CPU. In other embodiments, user motion can be detected by an accelerometer integrated in the scale or the motion is sensed with a single integrated microphone or microphone array, to detect the sounds of a user approaching.

Accordingly, from block 140, flow proceeds to block 142 where the user or other intrusion is sensed as data received at the platform apparatus. At block 144, the circuitry assesses whether the received data qualifies as requiring a wake up. If not, flow turns to block 140. If however, wake up is required, flow proceeds from block 144 to block 146 where the CPU assesses whether a possible previous user has approached the platform apparatus. This assessment is performed by the CPU accessing the user profile memory 146A and comparing data stored therein for one or more such previous users with criteria corresponding to the received data that caused the wake up. Such criteria includes, for example, the time of the day, the pace at which the user approached the platform apparatus as sensed by the motion detection circuitry, the height of the user as indicated by the motion sensing circuitry and/or a camera installed and integrated with the CPU, and/or more sophisticated biometric data provided by the user and/or automatically by the circuitry in the platform apparatus.

As discussed herein, such sophisticated circuitry can include one or more of the following user-specific attributes: foot length, type of foot arch, weight of user, and/or manner and speed at which the user steps onto the platform apparatus or by user speech (e.g., voice). In some embodiments, facial or body-feature recognition may also be used in connection with the camera and comparisons of images therefrom to images in the user profile memory.

From block 146, flow proceeds to block 148 where the CPU obtains and/or updates user corresponding data in the user profile memory. As a learning program is developed in the user profile memory, each access and use of the platform apparatus is used to expand on the data and profile for each such user. From block 148, flow proceeds to block 150 where a decision is made regarding whether the set of electrodes at the upper surface of the platform are ready for the user, such as may be based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user has stepped over the user display. If the electrodes are not ready for the user, flow proceeds from block 150 to block 152 to accommodate this delay.

Once the CPU determines that the electrodes are ready for use while the user is standing on the platform surface, flow proceeds to block 160. Stabilization of the user on the platform surface may be ascertained by injecting current through the electrodes via the interleaved arrangement thereof. Where such current is returned via other electrodes for a particular foot and/or foot size, and is consistent for a relatively brief period of time, for example, a few seconds, the CPU can assume that the user is standing still and ready to use the electrodes and related circuitry. At block 160, a decision is made that both the user and the platform apparatus are ready for measuring impedance and certain segments of the user's body, including at least one foot.

The remaining flow of FIG. 1f includes the application and sensing of current through the electrodes for finding the optimal electrodes (162) and for performing impedance measurements (block 164). These measurements are continued until completed at block 166 and all such useful measurements are recorded and are logged in the user profile memory for this specific user, at block 168. At block 172, the CPU generates output data to provide feedback as to the completion of the measurements and, as can be indicated as a request via the user profile for this user, as an overall report on the progress for the user and relative to previous measurements made for this user has stored in the user profile memory. Such feedback may be shown on the user display, through a speaker with co-located apertures in the platform for audible reception by the user, and/or by vibration circuitry which, upon vibration under control of the CPU, the user can sense through one or both feet while standing on the scale. From this output at block 172, flow returns to the low power mode as indicated at block 174 with the return to the beginning of the flow at the block 140.

FIG. 2a shows an example of the insensitivity to foot placement 200 on scale electrode pairs 205/210 with multiple excitation paths 220 and sensing current paths 215, consistent with various aspects of the present disclosure. An aspect of the platform is that it has a thickness and strength to support a human adult of at least 200 pounds without fracturing, and another aspect of the device platform is comprised of at least six electrodes, where the first electrode pair 205 is solid and the second electrode pair 210 are interleaved. Another aspect is the first and second interleaved electrode pairs 205/210 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. The resistivity can be below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which can be rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales.

In the present disclosure, the leg and foot impedance measurements can be simultaneously carried out using a multi-frequency approach, in which the leg and foot impedances are excited by currents modulated at two or more different frequencies, and the resulting voltages are selectively measured using a synchronous demodulator as shown in FIG. 3a. This homodyning approach can be used to separate signals (in this case, the voltage drop due to the imposed current) with very high accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example. Other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespectively of the foot position, as already explained.

Figure 2B:
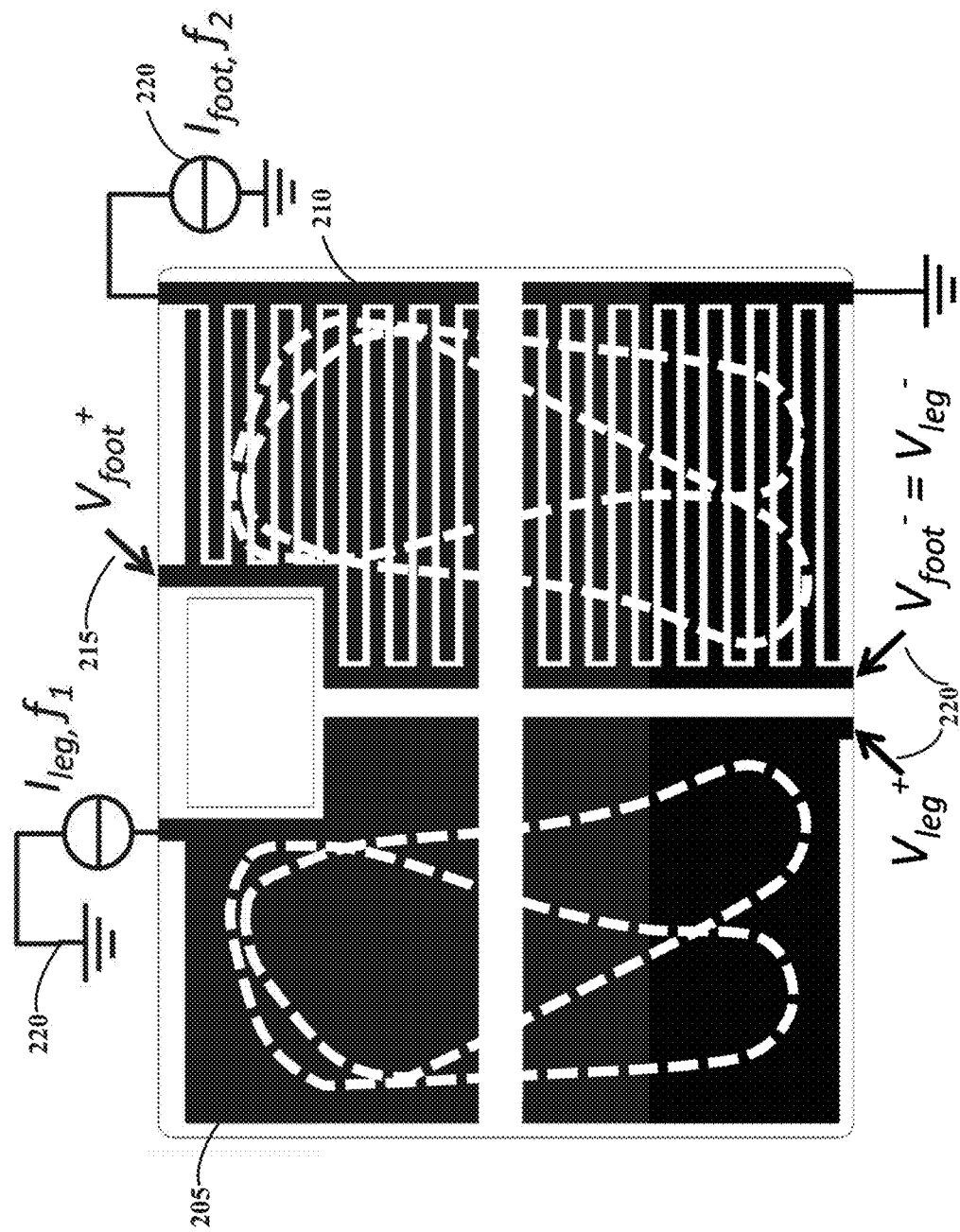
FIGS. 2b-2c show examples of electrode configurations, consistent with various aspects of the disclosure.

FIG. 2b shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the respective one foot (e.g., toes of the right foot). The leg current injection is coupled to the toes of the other foot (e.g., toes of the left foot).

Figure 2C:
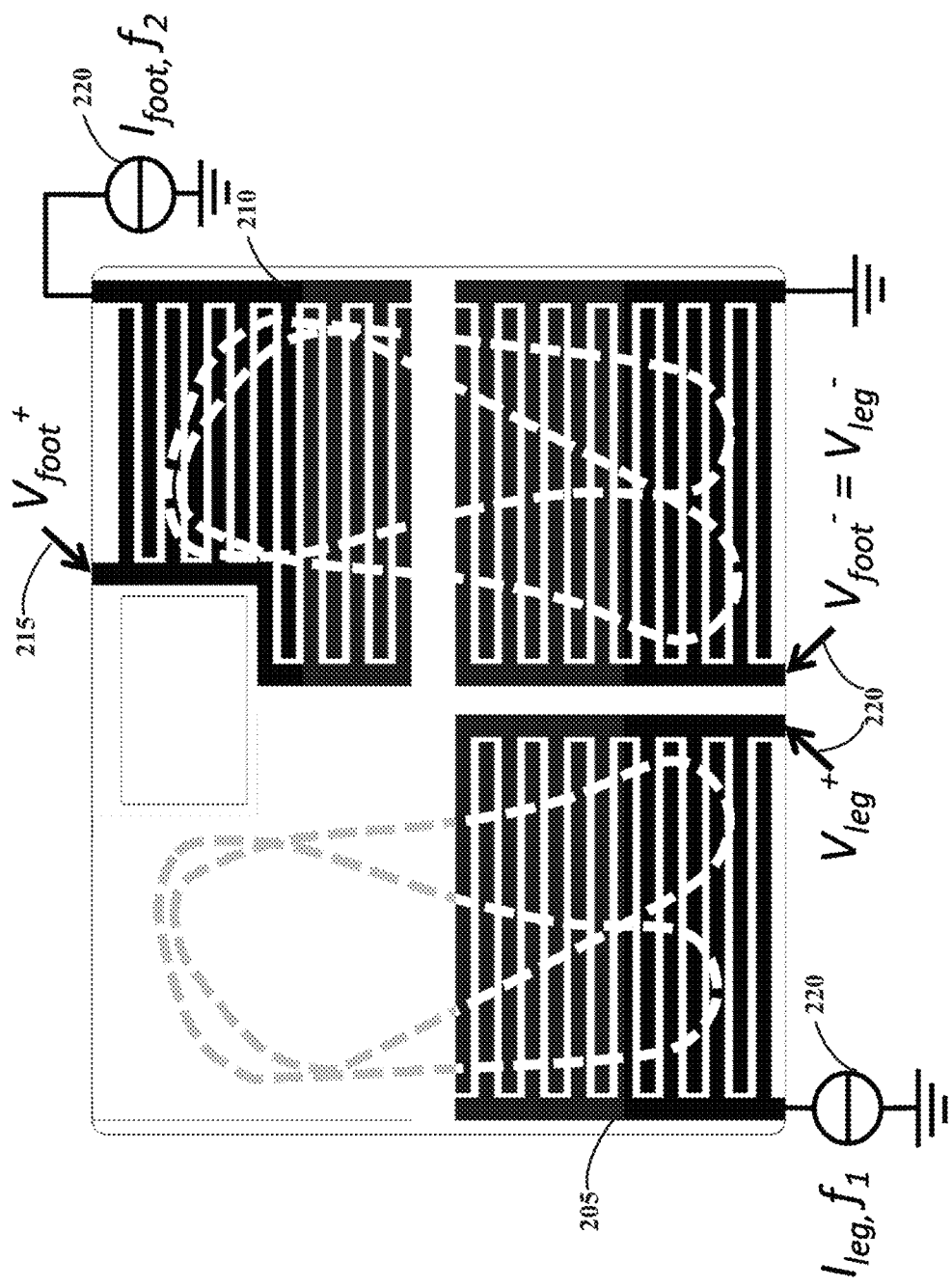

FIG. 2c shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the one foot (e.g., toes of the right foot). The leg current injection is coupled to the heels of the other foot of the user (e.g., heels of the left foot).

Figure 3B:
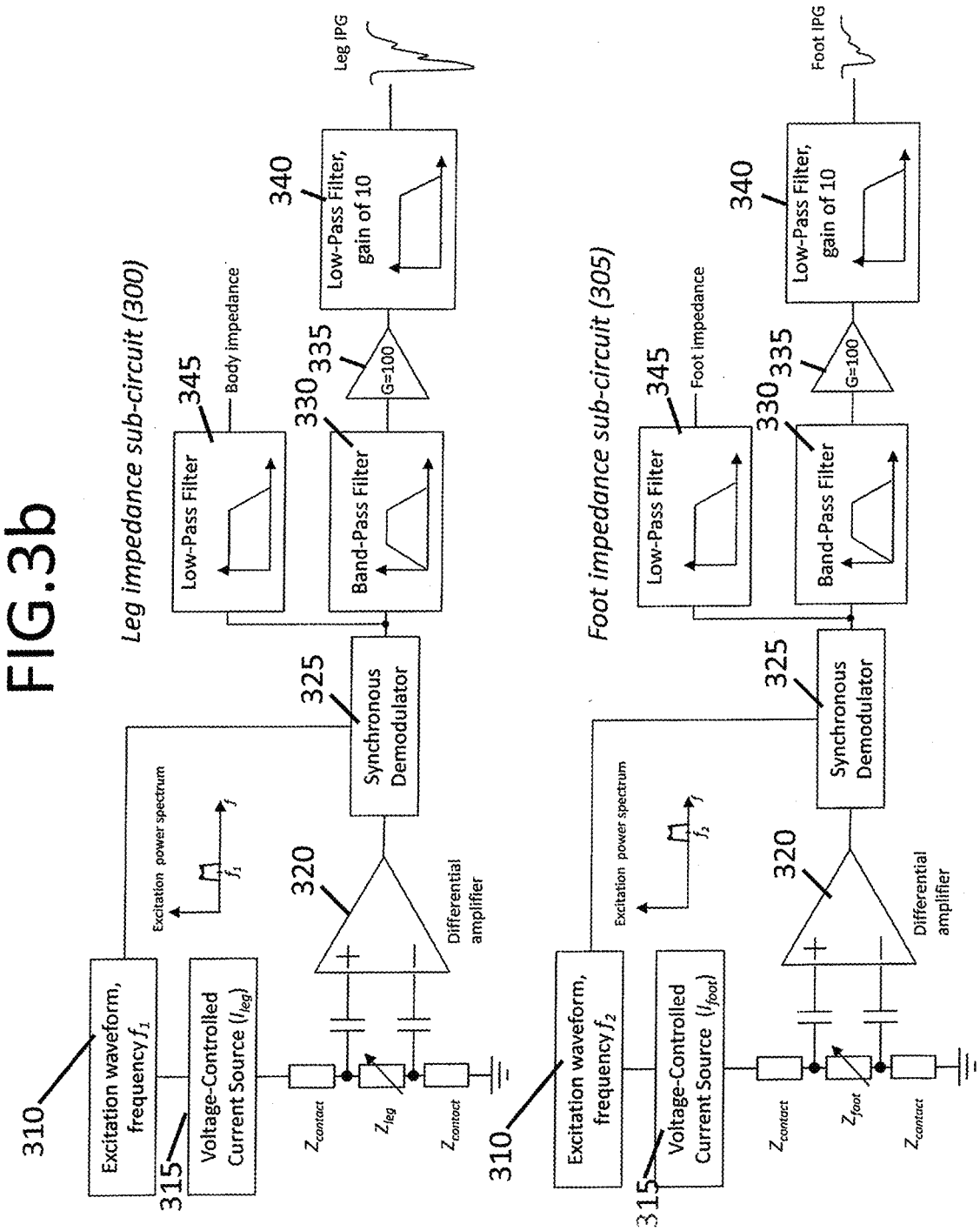

FIGS. 3a-3b show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 3a-3b are separated in to a leg impedance sub-circuit 300 and a foot impedance sub-circuit 305.

Excitation is provided by way of an excitation waveform circuit 310. The excitation waveform circuit 310 provides a stable amplitude excitation signal by way of various wave shapes of various, frequencies, such as more specifically, a sine wave signal (as is shown in FIG. 3a) or, more specifically, a square wave signal (as shown in FIG. 3b). This excitation waveform (of sine, square, or other wave shape) is fed to a voltage-controlled current source circuit 315 which scales the signal to the desired current amplitude. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 320. The sense electrodes on the scale are AC-coupled to the inputs of the differential amplifier 320 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet). Alternatively, a fully differential input amplification stage can be used which eliminates the need for DC restoration.

The signal is then demodulated with a phase-sensitive synchronous demodulator circuit 325. The demodulation is achieved in this example by multiplying the signal by 1 or −1 synchronously in-phase with the current excitation. Such alternating gain is provided by an operational amplifier (op amp) and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input of the op amp. When open, the gain of the stage is unity. When closed (positive input grounded), the stage acts as an inverting amplifier with a gain of −1. Further, fully differential demodulators can alternatively be used which employ pairs of DPST analog switches whose configuration can provide the benefits of balanced signals and cancellation of charge injection artifacts. Alternatively, other demodulators such as analog multipliers or mixers can be used. The in-phase synchronous detection allows the demodulator to be sensitive to only the real, resistive component of the leg or foot impedance, thereby rejecting any imaginary, capacitive components which may arise from parasitic elements associated with the foot to electrode contacts.

Once demodulated, the signal is band-pass filtered (0.4-80 Hz) with a band-pass filter circuit 330 before being amplified with a gain of 100 with a non-inverting amplifier circuit 335 (e.g., using an LT1058 operational amplifier from Linear Technology Inc.). The amplified signal is further amplified by 10 and low-pass filtered (cut-off at 20 Hz) using a low-pass filter circuit 340 such as 2-pole Sallen-Key filter stage with gain. The signal is then ready for digitization and further processing. In certain embodiments, the signal from the demodulator circuit 325 can be passed through an additional low-pass filter circuit 345 to determine body or foot impedance.

In certain embodiments, the generation of the excitation voltage signal, of appropriate frequency and amplitude, is carried out by a microcontroller, such as an MSP430 (Texas Instruments, Inc.) or a PIC18Fxx series (Microchip Technology, Inc.). The voltage waveform can be generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. In certain embodiments, the generation of the excitation frequency signal can be accomplished by an independent quartz crystal oscillator whose output is frequency divided down by a series of toggle flip-flops (such as an ECS-100AC from ECS International, Inc., and a CD4024 from Texas Instruments, Inc.). In certain embodiments, the generation of the wave shape and frequency can be accomplished by a direct digital synthesis (DDS) integrated circuit (such as an AD9838 from Analog Devices, Inc.). In certain embodiments, the generation of the wave shape (either sine or square) and frequency can be accomplished by a voltage-controlled oscillator (VCO) which is controlled by a digital microcontroller, or which is part of a phase-locked loop (PLL) frequency control circuit. Alternatively, the waveforms and frequencies can be directly generated by on- or off-chip digital-to-analog converters (DACs).

In certain embodiments, the shape of the excitation is not square, but sinusoidal. Such configuration can reduce the requirements on bandwidth and slew rate for the current source and instrumentation amplifier. Harmonics, potentially leading to higher electromagnetic interference (EMI), can also be reduced. Such excitation may also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation could also be more power-efficient. In certain embodiments, the shape of the excitation is not square, but trapezoidal. Alternatively, raised cosine pulses (RCPs) could be used as the excitation wave shape, providing an intermediate between sine and square waves. RCPs could provide higher excitation energy content for a given amplitude, but with greatly reduced higher harmonics.

To further reduce potential electromagnetic interference (EMI), other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). Because of the synchronous demodulation scheme, phase-to-phase variability introduced by spread-spectrum techniques will not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot can be used for standard Body Impedance Analysis (BIA), aiming at extracting the relative content of total water, free-water, fat mass and other body composition measures. Impedance measurements for BIA are typically done at frequencies ranging from kilohertz up to several megahertz. The multi-frequency synchronous detection measurement methods described above can readily be used for such BIA, provided that low-pass filtering (345, FIGS. 3a and 3b) instead of band-pass filtering (330, FIGS. 3a and 3b) is performed following the demodulation. In certain embodiments, a separate demodulator channel may be driven by the quadrature phase of the excitation signal to allow the imaginary component of the body impedance to be extracted in addition to the real component. A more accurate BIA can be achieved by measuring both the real and imaginary components of the impedance. This multi-frequency technique can be combined with traditional sequential measurements used for BIA, in which the impedance is measured at several frequencies sequentially. These measurements are repeated in several body segments for segmental BIAs, using a switch matrix to drive the current into the desired body segments.

Figure 14A:
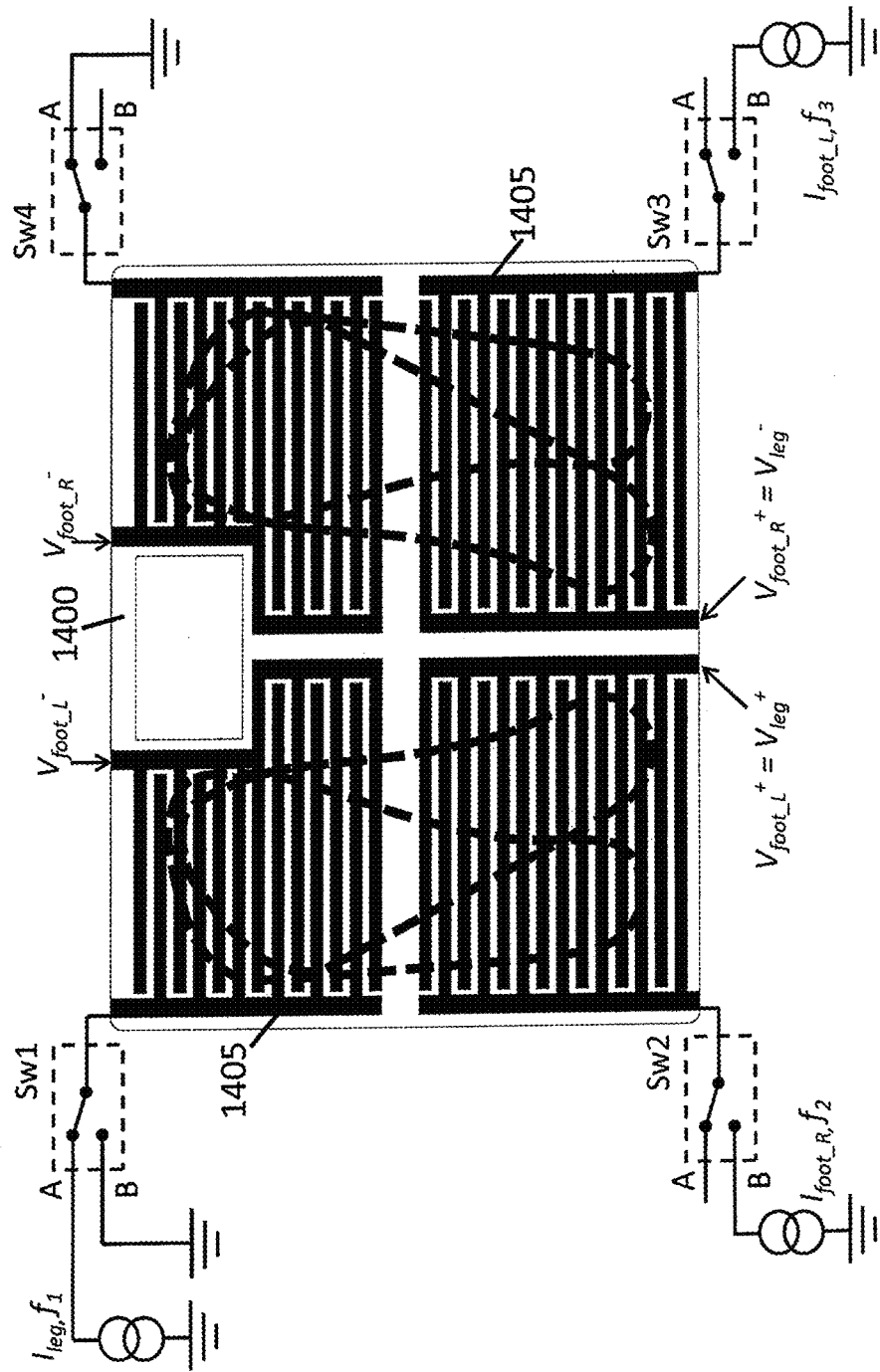
FIG. 14a shows another example of a scale with interleaved foot electrodes to inject and sense current from one foot to another foot, and measure Foot IPG signals in both feet, consistent with various aspects of the present disclosure.

While FIG. 2a shows a circuit and electrode configuration suitable to measure two different segments (legs and one foot), this approach is not readily extendable to more segments due to the shared current return electrode (ground). To overcome this limitation, and provide simultaneous measurements in both feet, the system can be augmented with analog switches to provide time-multiplexing of the impedance measurements in the different segments. This multiplexing can be a one-time sequencing (each segment is measured once), or interleaved at a high-enough frequency that the signal can be simultaneously measured on each segment. The minimum multiplexing rate for proper reconstruction is twice the bandwidth of the measured signal, based on signal processing theory (the Nyquist rate), which equals to about 100 Hz for the impedance signal considered here. The rate must also allow for the signal path to settle in between switching, which usually limits the maximum multiplexing rate. Referring to FIG. 14a, one cycle might start the measurement of the leg impedance and left foot impedances (similarly to previously described, sharing a common return electrode), but then follow with a measurement of the right foot after reconfiguring the switches. For specific information regarding typical switch configurations, reference to U.S. patent application Ser. No. 14/338,266 filed on Oct. 7, 2015, which is fully incorporated for its specific and general teaching of switch configurations.

Since right and left feet are measured sequentially, one should note that a unique current source (at the same frequency) may be used to measure both, providing that the current source is not connected to the two feet simultaneously through the switches, in which case the current would be divided between two paths. One should also note that a fully-sequential measurement, using a single current source (at a single frequency) successively connected to the three different injection electrodes, could be used as well, with the proper switch configuration sequence (no splitting of the current path).

Figure 14C:
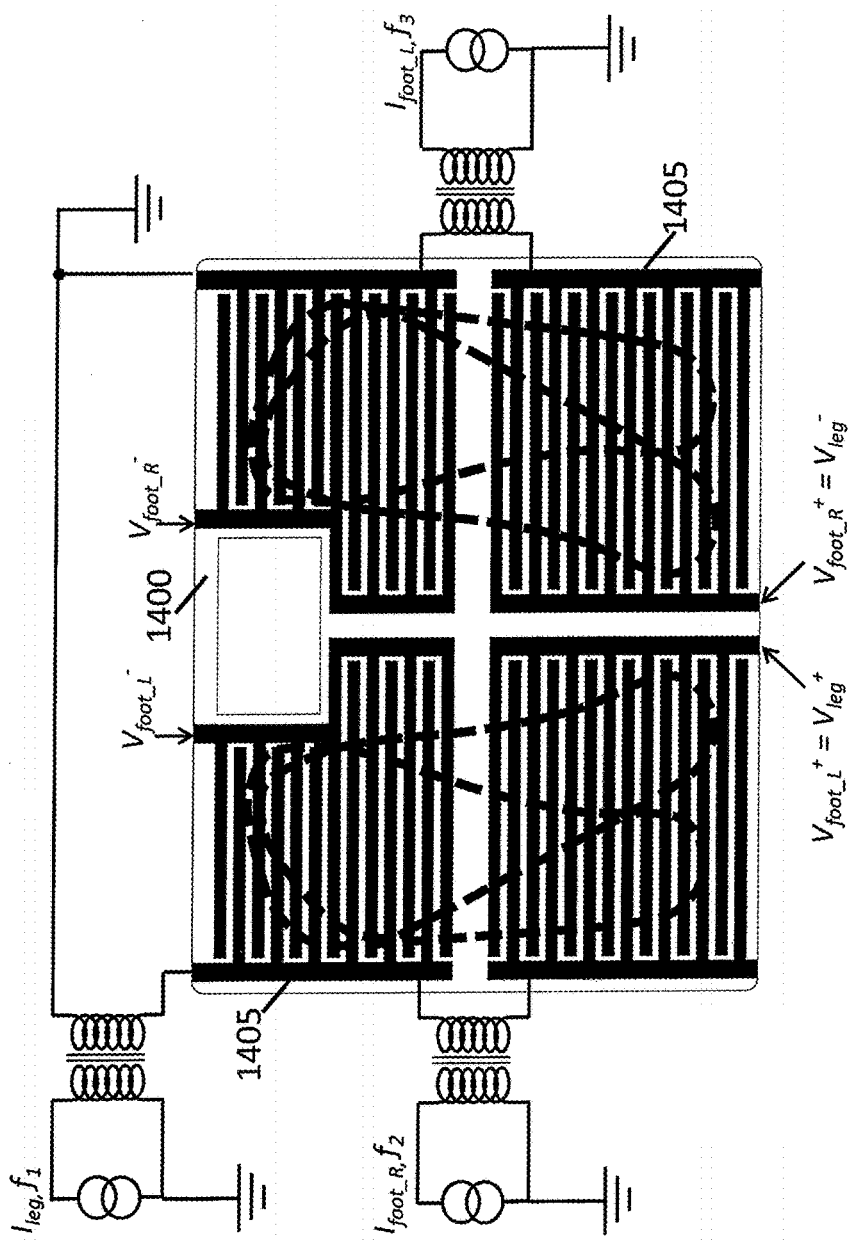
FIG. 14c shows another example approach to floating current sources is the use of transformer-coupled current sources, consistent with various aspects of the present disclosure.

In certain embodiments, the measurement of various body segments, and in particular the legs, right foot and left foot, is achieved simultaneously due to as many floating current sources as segments to be measured, running at separate frequencies so they can individually be demodulated. Such configuration is exemplified in FIG. 14b for three segments (legs, right and left feet). Such configuration has the advantage to provide true simultaneous measurements without the added complexity of time-multiplexing/demultiplexing, and associated switching circuitry. An example of such a floating current source is found in Plickett, et al., Physiological Measurement, 32 (2011). Another approach to floating current sources is the use of transformer-coupled current sources (as depicted in FIG. 14c). Using transformers to inject current into the electrodes enables the use of simpler, grounded-load current sources on the primary, while the electrodes are connected to the secondary. The transformer turns ratio can typically be 1:1, and since frequencies of interest for impedance measurement are typically in the 10-1000 kHz (occasionally 1 kHz for BIA), relatively small pulse transformers can be used. In order to limit the common mode voltage of the body, one of the electrodes in contact with the foot can be grounded.

While certain embodiments presented in the above specification have used current sources for excitation, the excitation can also be performed by a voltage source, where the resulting injection current is monitored by a current sense circuit so that impedance can still be derived by the ratio of the sensed voltage (on the sense electrodes) over the sensed current (injected in the excitation electrodes). It should be noted that broadband spectroscopy methods could also be used for measuring impedances at several frequencies. Combined with time-multiplexing and current switching described above, multi-segment broadband spectroscopy can be achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG.

Figure 3C:
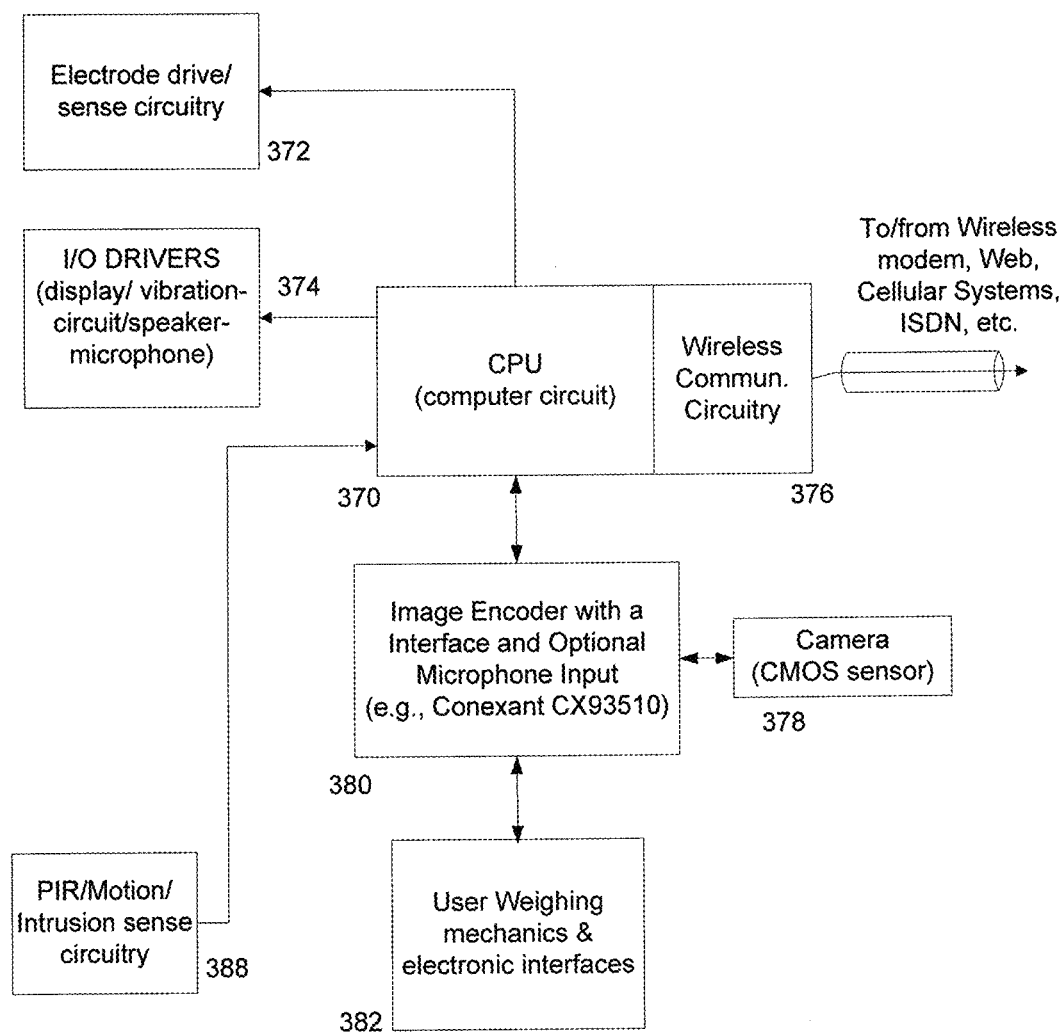
FIG. 3c depicts an example block diagram of circuitry for operating core circuits and modules, including for example those of FIGS. 3a-3b, used in various specific embodiments of the present disclosure.

Consistent with yet further embodiments of the present disclosure, FIG. 3c depicts an example block diagram of circuitry for operating core circuits and modules, including, for example, the operation of the CPU as in FIG. 1a with the related more specific circuit blocks/modules in FIGS. 3A-3B. As shown in the center of FIG. 3c, the computer circuit 370 is shown with other previously-mentioned circuitry in a generalized manner without showing some of the detailed circuitry (e.g., amplification and current injection/sensing (372)). The computer circuit 370 can be used as a control circuit with an internal memory circuit (or as integrated with the memory circuit for the user profile memory 146A of FIG. 1a) for causing, processing and/or receiving sensed input signals as at block 372. As discussed, these sensed signals can be responsive to injection current and/or these signals can be sensed by less complex grid-based sense circuitry surrounding the platform as is convention in capacitive touch-screen surfaces which, in certain embodiments, the platform includes.

As noted, the memory circuit can be used not only for the user profile memory, but also as to provide configuration and/or program code and/or other data such as user-specific data from another authorized source such as from a user monitoring his/her logged data and/or profile from a remote desk-top. The remote device or desk-top can communicate with and access such data via a wireless communication circuit 376. For example, the wireless communication circuit 376 provides an interface between an app on the user's cellular telephone/tablet and the apparatus, wherefrom the IPhone is the output/input interface for the platform (scale) apparatus including, for example, an output display, speaker and/or microphone, and vibration circuitry; each of these I/O aspects and components being discussed herein in connection with other example embodiments.

A camera 378 and image encoder circuit 380 (with compression and related features) can also be incorporated as an option. As discussed above, the weighing scale components, as in block 382, are also optionally included in the housing which encloses and/or surrounds the platform.

For long-lasting battery life in the platform apparatus (batteries not shown), at least the CPU 370, the wireless communication circuit 376, and other current draining circuits are inactive unless and until activated in response to the intrusion/sense circuitry 388. As shown, one specific implementation employs a Conexant chip (e.g., CX93510) to assist in the low-power operation. This type of circuitry is designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) to alleviate the necessity of external memory. The chip uses a simple register set via the microprocessor interface and allows for wide flexibility in terms of compatible operation with another microprocessor.

In one specific embodiment, a method of using the platform with the plurality of electrodes are concurrently contacting a limb of the user, includes operating such to automatically obtain measurement signals from the plurality of electrodes. As noted above, these measurement signals might initially be through less complex (e.g., capacitive grid-type) sense circuitry. Before or while obtaining a plurality of measurement signals by operating the circuitry, the signal-sense circuitry 388 is used to sense wireless-signals indicative of the user approaching the platform and, in response, causing the CPU circuitry 370 to transition from a reduced power-consumption mode of operation and at least one higher power-consumption mode of operation. After the circuitry is operating in the higher power-consumption mode of operation, the CPU accesses the user-corresponding data stored in the memory circuit and causes a plurality of impedance-measurement signals to be obtained by using the plurality of electrodes while they are contacting the user via the platform; therefrom, the CPU generates signals corresponding to cardiovascular timings of the user.

The signal-sense circuit can be employed as a passive infrared detector and with the CPU programmed (as a separate module) to evaluate whether radiation from the passive infrared detector is indicative of a human. For example, sensed levels of radiation that corresponds to a live being, such as a dog, that is less than a three-foot height, and/or has not moved for more than a couple seconds, can be assessed as being a non-human.

Accordingly, as the user is recognized as being human, the CPU is activated and begins to attempt the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU can also select one of a plurality of different types of user-discernible visual/audible/tactile information and for presenting the discerned user with visual/audible/tactile information that was retrieved from the memory as being specific to the user. For example, user-selected visual/audible data can be outputted for the user. Also, responsive to the motion detection indication, the camera can be activated to capture at least one image of the user while the user is approaching the platform (and/or while the user is on the platform to log confirmation of the same user with the measured impedance information). As shown in block 374 of FIG. 3c, where a speaker is also integrated with the CPU, the user can simply command the platform apparatus to start the process and activation proceeds. As previously discussed, the scale can include voice input/output circuitry to receive the user commands via voice commands.

In another method, the circuitry of FIG. 3c is used with the electrodes being interleaved and engaging the user, as a combination weighing scale (via block 382) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed in the memory circuit and identified as being specific to the user. This information can be later retrieved by the user, medical and/or security personnel, according to a data-access authorization protocol as might be established upon initial configuration for the user.

Figure 3D:
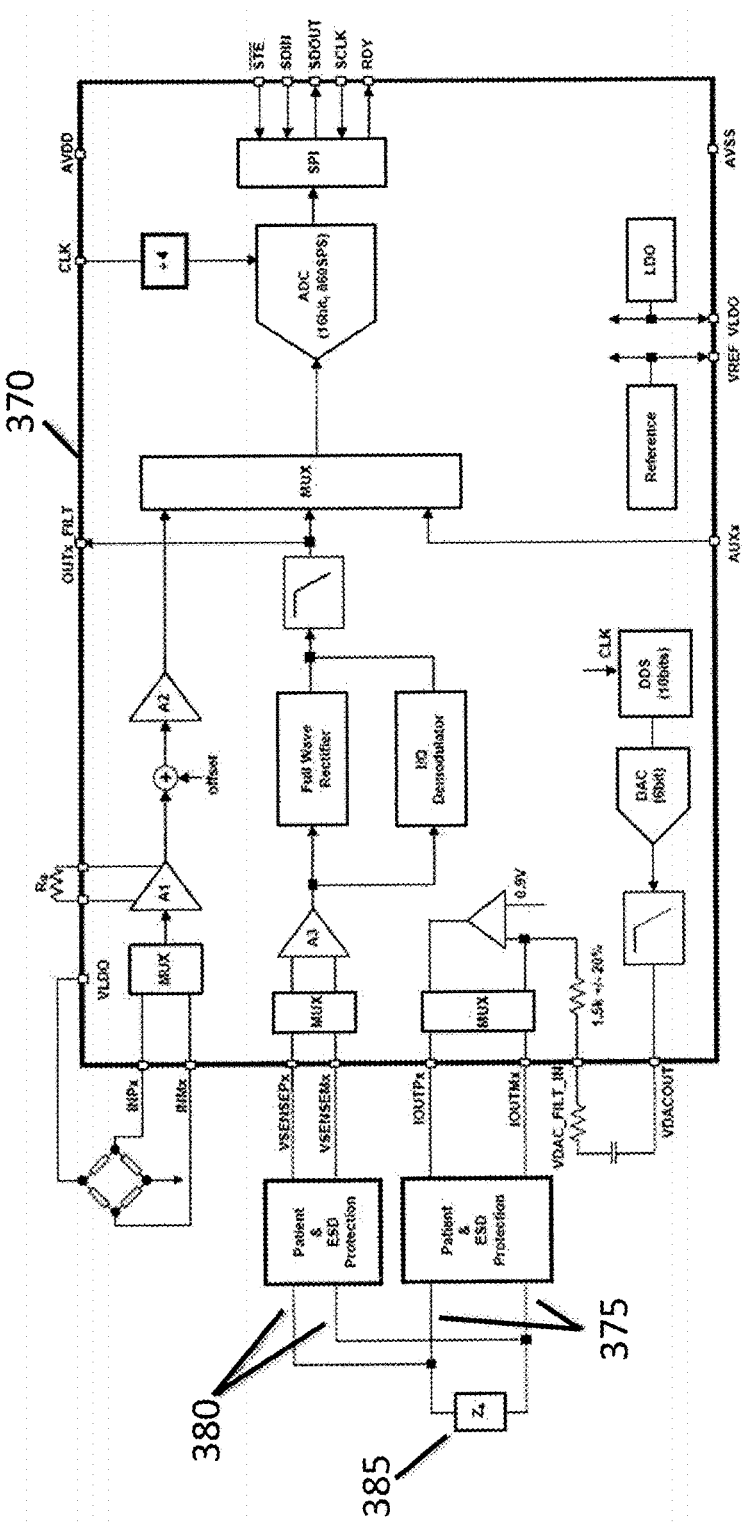
FIG. 3d shows an exemplary block diagram depicting the circuitry for interpreting signals received from electrodes.

FIG. 3d shows an exemplary block diagram depicting the circuitry for interpreting signals received from electrodes (e.g., 372 of FIG. 3c), and/or CPU 370 of FIG. 3c. The input electrodes 375 transmit electrical signals through the patient's body (depending on the desired biometric and physiological test to be conducted) and output electrodes 380 receive the modified signal as affected by a user's electrical impedance 385. Once received by the output electrodes 380, the modified signal is processed by processor circuitry 370 based on the selected test. Signal processing conducted by the processor circuitry 370 is discussed in more detail above (with regard to FIGS. 3a-b). In certain embodiments of the present disclosure, the circuitry within 370 is provided by Texas Instruments part #AFE4300.

FIG. 4 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 400, the Leg IP and the Foot IPG are simultaneously measured. As shown at 405, the Leg IPG is low-pass filtered at 20 Hz with an 8-pole Butterworth filter, and inverted so that pulses have an upward peak. The location of the pulses is then determined by taking the derivative of this signal, integrating over a 100 ms moving window, zeroing the negative values, removing the large artifacts by zeroing values beyond 15× the median of the signal, zeroing the values below a threshold defined by the mean of the signal, and then searching for local maxima. Local maxima closer than a defined refractory period of 300 ms to the preceding ones are dismissed. The result is a time series of pulse reference timings.

As is shown in 410, the foot IPG is low-pass filtered at 25 Hz with an 8-pole Butterworth filter and inverted (so that pulses have an upward peak). Segments starting from the timings extracted (415) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is then computed using an intersecting tangent method, where the fiducial (420) is defined by the intersection between a first tangent to the IPG at the point of maximum positive derivative and a second tangent to the minimum of the IPG on the left of the maximum positive derivative within the segment.

The time series resulting from this two-step extraction is used with another signal to facilitate further processing. These timings are used as reference timings to improve the SNR of BCG signals to extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings are extracted, either in Leg IPG or Foot IPG. Following the computation of the SNRs, pulses with a SNR below a threshold value are eliminated from the time series, to prevent propagating noise. The individual SNRs may be computed in a variety of methods known to one skilled in the art. For instance, an estimated pulse can be computed by ensemble averaging segments of signal around the pulse reference timing. The noise associated with each pulse is defined as the difference between the pulse and the estimated pulse. The SNR is the ratio of the root-mean-square (RMS) value of the estimated pulse over the RMS value of the noise for that pulse.

In certain embodiments, the time interval between the Leg IPG pulses, and the Foot IPG pulses, also detected by the above-mentioned methods, is extracted. The Leg IPG measuring a pulse occurring earlier in the legs compared to the pulse from the Foot IPG, the interval between these two is related to the propagation speed in the lower body, i.e., the peripheral vasculature. This provides complementary information to the interval extracted between the BCG and the Foot IPG for instance, and is used to decouple central versus peripheral vascular properties. It is also complementary to information derived from timings between the BCG and the Leg ICG.

Figure 5:
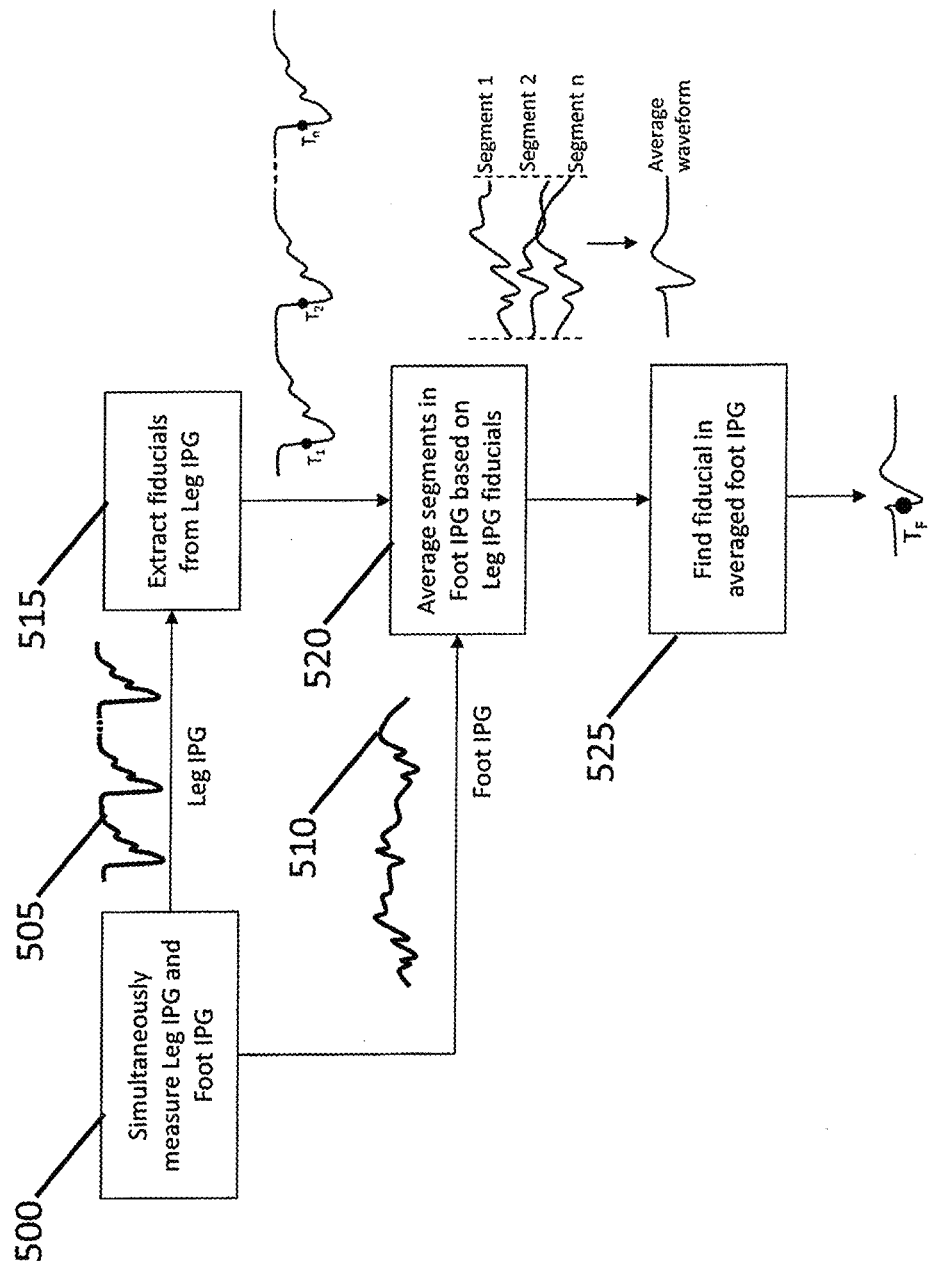
FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure.

FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure. Similar to the method shown in FIG. 4, the Leg IP and the Foot IPG are simultaneously measured (500), the Leg IPG is low-pass filtered (505), the foot IPG is low-pass filtered (510), and segments starting from the timings extracted (515) from the Leg IPG (reference timings). The segments of the Foot IPG extracted based on the Leg IPG timings are ensemble-averaged (520) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise, as shown in FIG. 7b. These timings are used together with timings extracted from the BCG for the purpose of computing the PTT and (PWV). Timings derived from ensemble-averaged waveforms and individual waveforms can also be both extracted, for the purpose of comparison, averaging and error-detection.

Specific timings extracted from the IPG pulses (from either leg or foot) are related (but not limited) to the peak of the pulse, the minimum preceding the peak, or the maximum second derivative (maximum rate of acceleration) preceding the point of maximum derivative. An IPG pulse and the extraction of a fiducial (525) in the IPG can be performed by other signal processing methods, including (but not limited to) template matching, cross-correlation, wavelet-decomposition, or short window Fourier transform.

Figure 6A:
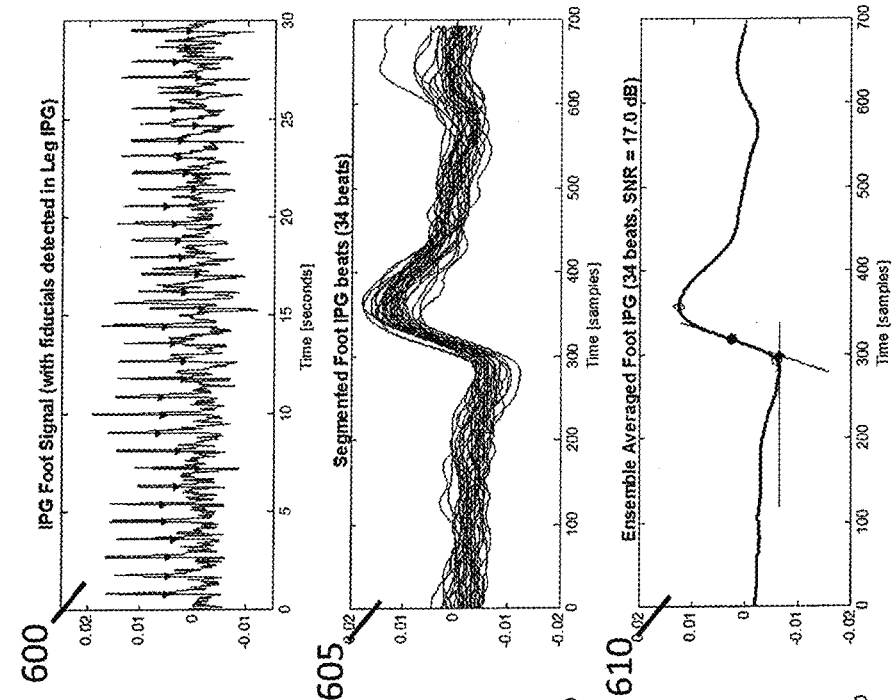
FIG. 6a shows examples of the Leg IPG signal with fiducials; the segmented Leg IPG into beats; and the ensemble-averaged Leg IPG beat with fiducials and calculated SNR, for an exemplary high-quality recording, consistent with various aspects of the present disclosure.
Figure 6B:
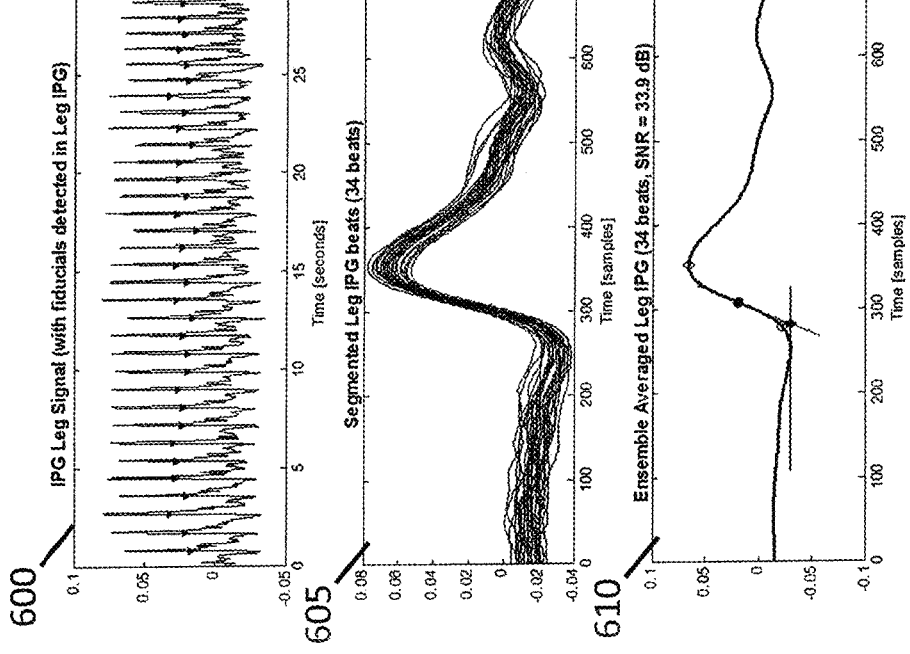
FIG. 6b shows examples of the Foot IPG signal with fiducials derived from the Leg IPG fiducials; the segmented Foot IPG into beats; and the ensemble-averaged Foot IPG beat with fiducials and calculated SNR, for an exemplary high-quality recording, consistent with various aspects of the present disclosure.

FIG. 6a shows examples of the Leg IPG signal with fiducials (plot 600); the segmented Leg IPG into beats (plot 605); and the ensemble-averaged Leg IPG beat with fiducials and calculated SNR (plot 610), for an exemplary high-quality recording, consistent with various aspects of the present disclosure. FIG. 6b shows examples of the Foot IPG signal with fiducials derived from the Leg IPG fiducials (plot 600); the segmented Foot IPG into beats (plot 605); and the ensemble-averaged Foot IPG beat with fiducials and calculated SNR (plot 610), for an exemplary high-quality recording, consistent with various aspects of the present disclosure.

FIG. 7a shows examples of the Leg IPG signal with fiducials (plot 700); the segmented Leg IPG into beats (plot 705); and the ensemble averaged Leg IPG beat with fiducials and calculated SNR (plot 710), for an exemplary low-quality recording, consistent with various aspects of the present disclosure.

FIG. 7b shows examples of the Foot IPG signal with fiducials derived from the Leg IPG fiducials (plot 700); the segmented Foot IPG into beats (plot 705); and the ensemble-averaged Foot IPG beat with fiducials and calculated SNR (plot 710), for an exemplary low-quality recording, consistent with aspects of the present disclosure.

Figure 8:
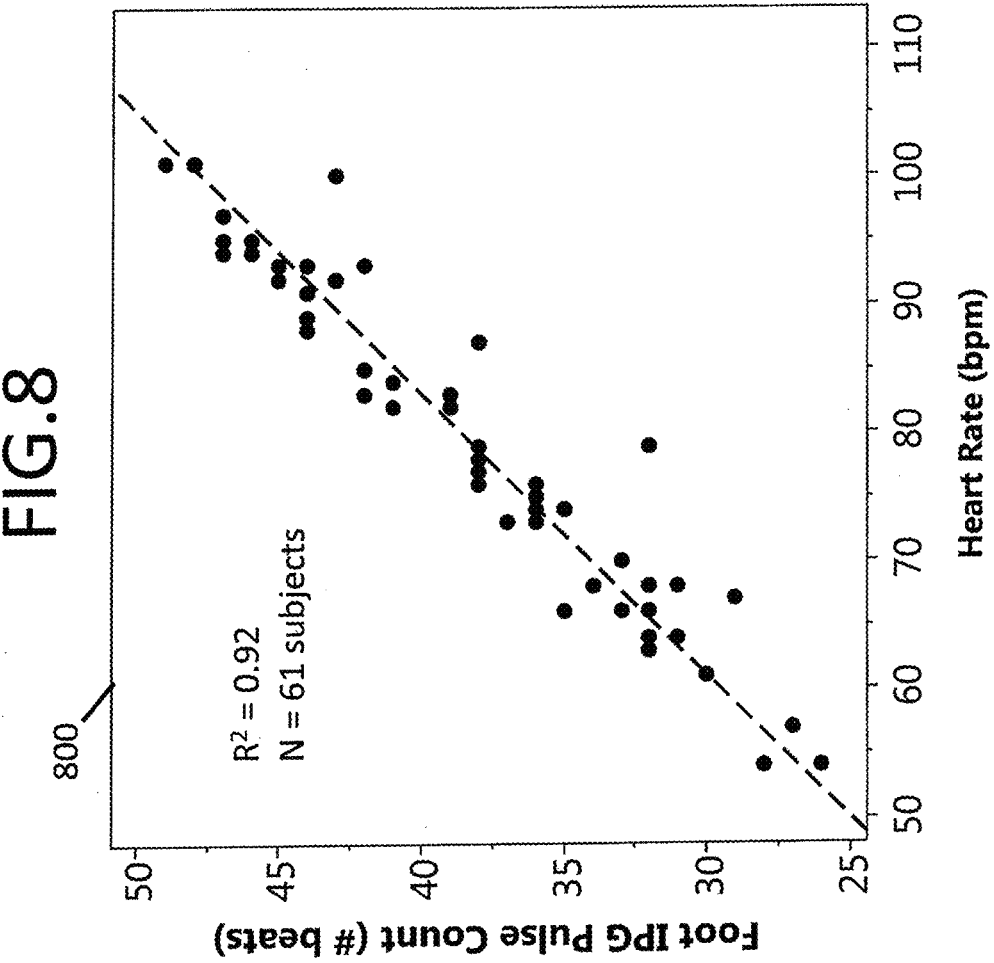
FIG. 8 shows an example correlation plot for the reliability in obtaining the low SNR Foot IPG pulse for a 30-second recording, using the first impedance signal as the trigger pulse, from a study including 61 test subjects with various heart rates, consistent with various aspects of the present disclosure.

FIG. 8 shows an example correlation plot 800 for the reliability in obtaining the low SNR Foot IPG pulse for a 30-second recording, using the first impedance signal as the trigger pulse, from a study including 61 test subjects with various heart rates, consistent with various aspects of the present disclosure.

In certain embodiments, a dual-Foot IPG is measured, allowing the detection of blood pressure pulses in both feet. Such information can be used for diagnostic of peripheral arterial diseases (PAD) by comparing the relative PATs in both feet to look for asymmetries. It can also increase the robustness of the measurement by allowing one foot to have poor contact with electrodes (or no contact at all). SNR measurements can be used to assess the quality of the signal in each foot, and to select the best one for downstream analysis. Timings extracted from each foot can be compared and set to flag potentially inaccurate PWV measurements due to arterial peripheral disease, in the event these timings are different by more than a threshold. Alternatively, timings from both feet are pooled to increase the overall SNR if their difference is below the threshold.

In certain embodiments, the disclosure is used to measure a PWV, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

Figure 9B:
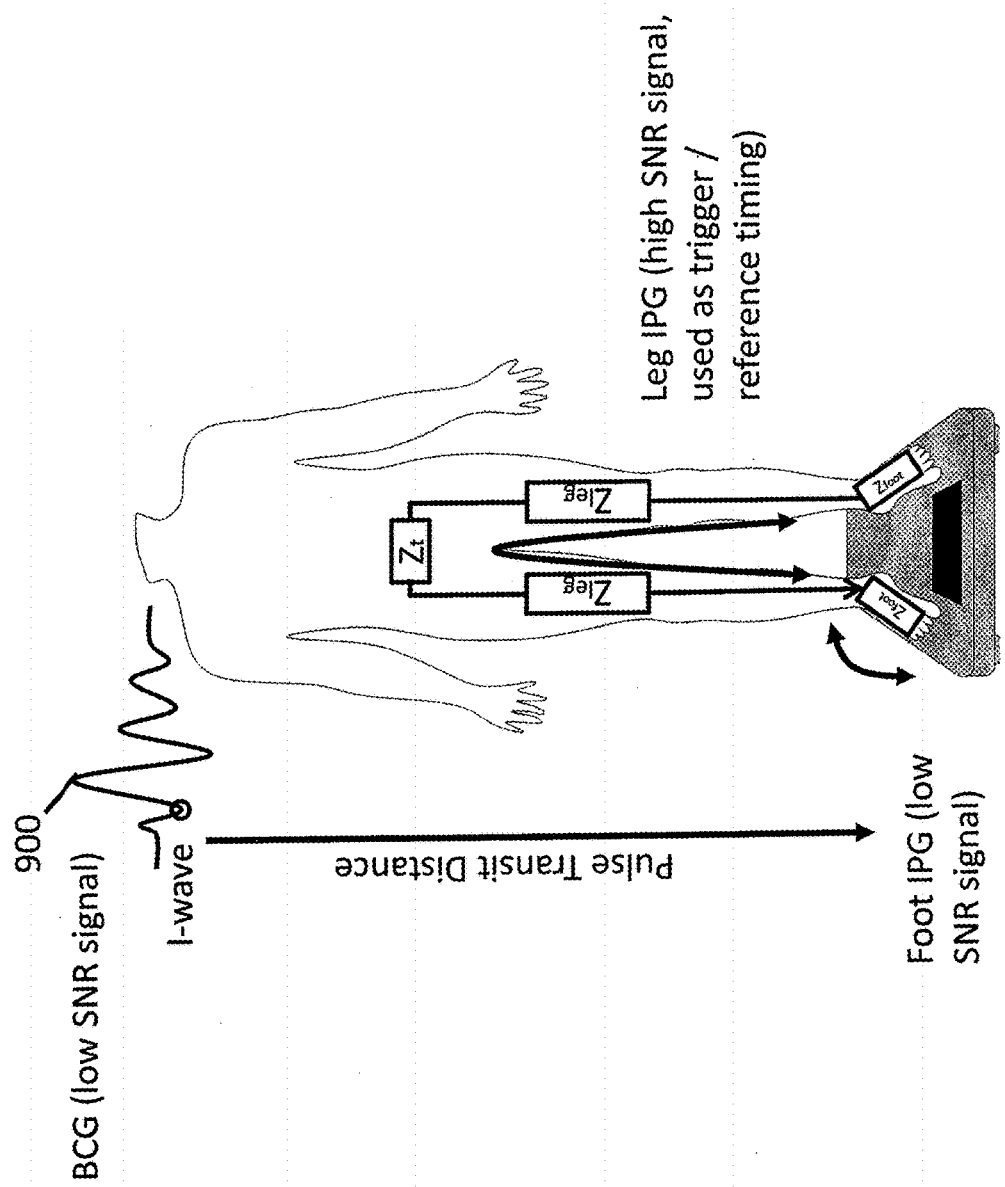

FIGS. 9a-b show example configurations to obtain the PTT, using the first IPG as the triggering pulse for the Foot IPG and BCG, consistent with various aspects of the present disclosure. The I-wave of the BCG 900 normally depicts the headward force due to cardiac ejection of blood into the ascending aorta which is used as a timing fiducial indicative of the pressure pulse initiation of the user's proximal aorta relative to the user's heart. The J-wave is indicative of timings in the systole phase and also incorporates information related to the strength of cardiac ejection and the ejection duration. The K-Wave provides systolic and vascular information of the user's aorta. The characteristic timings of these and other BCG waves are used as fiducials that can be related to fiducials of the IPG signals of the present disclosure.

Figure 10:
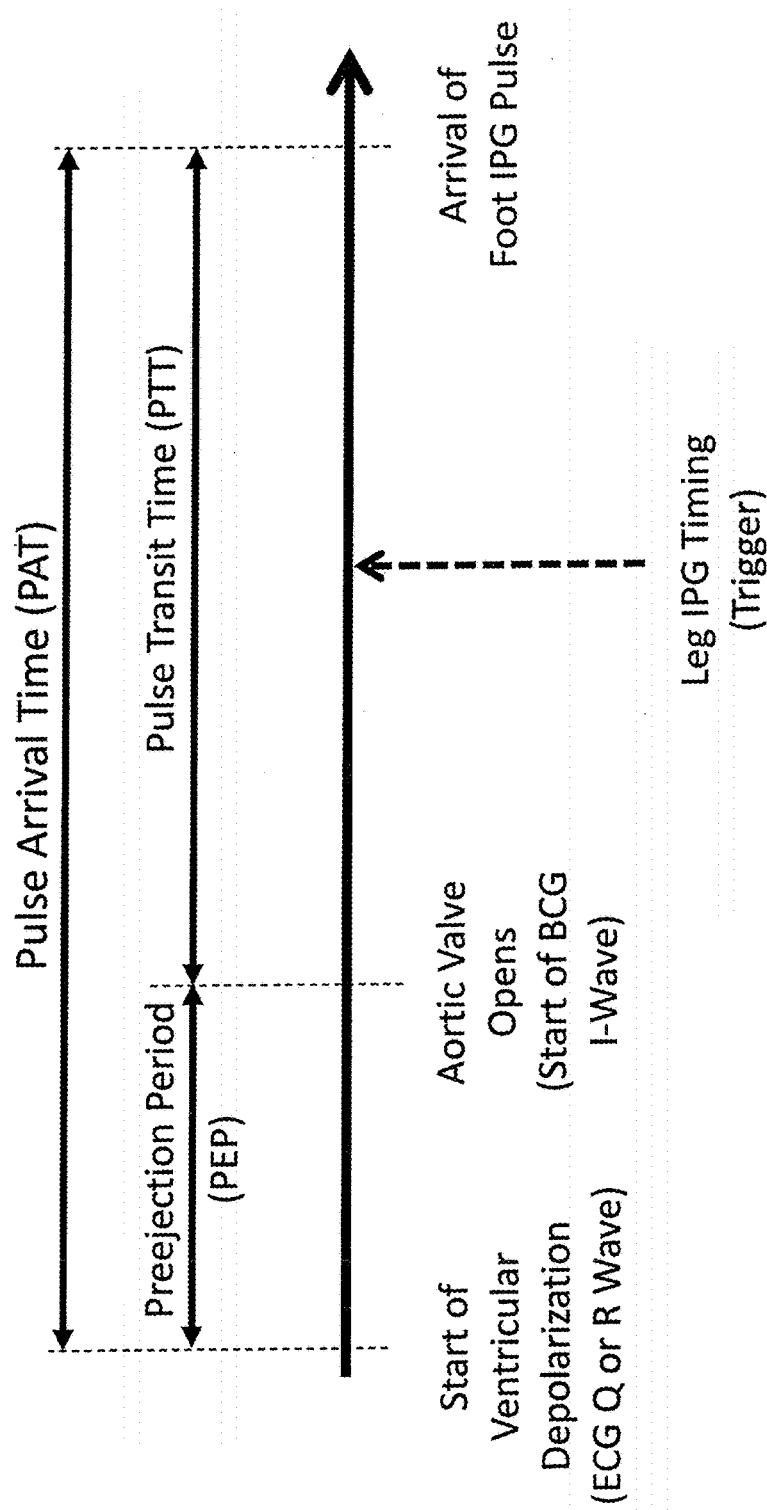
FIG. 10 shows nomenclature and relationships of various cardiovascular timings, consistent with various aspects of the present disclosure.

FIG. 10 shows nomenclature and relationships of various cardiovascular timings, consistent with various aspects of the present disclosure.

Figure 11:
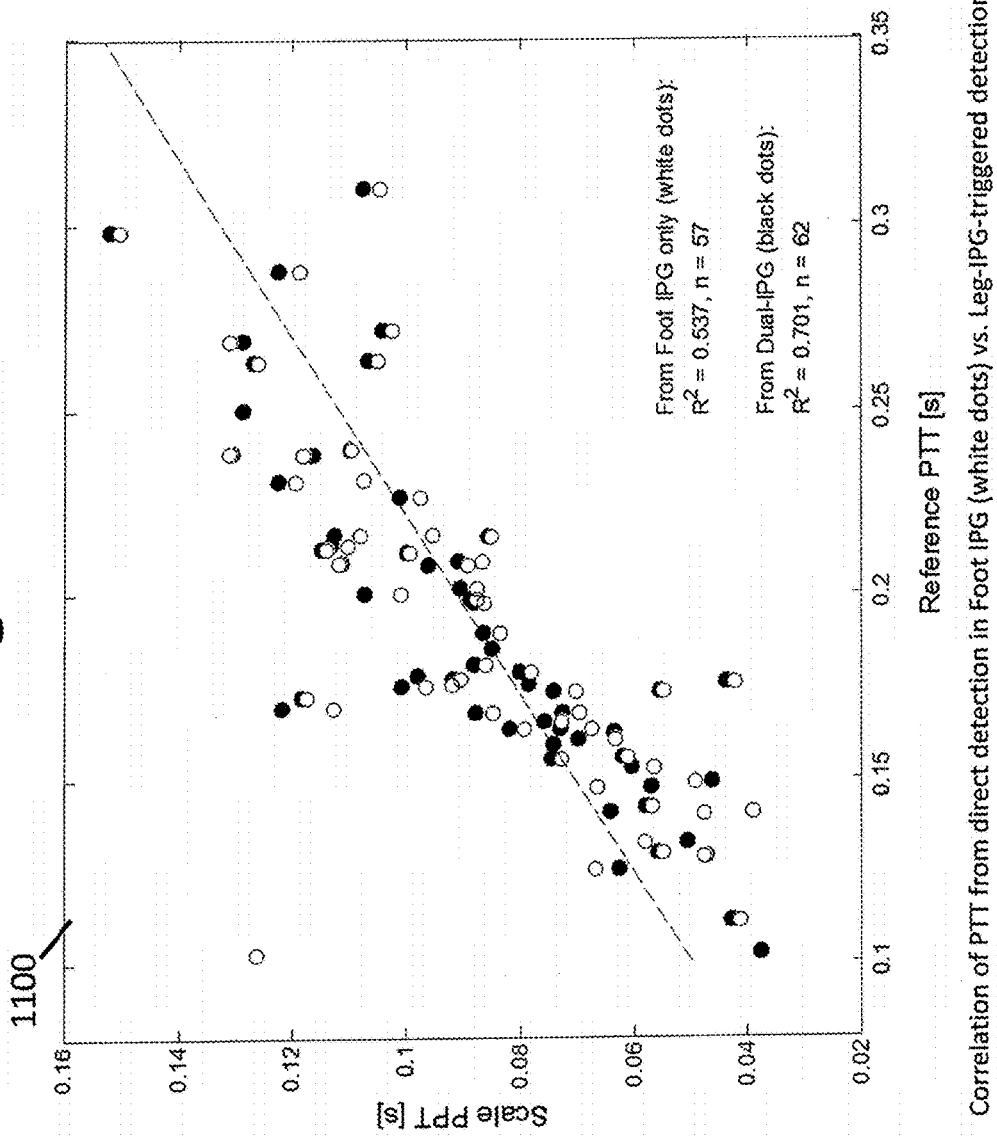
FIG. 11 shows an example graph of PTT correlations for two detection methods (white dots) Foot IPG only, and (black dots) Dual-IPG method, consistent with various aspects of the present disclosure.

FIG. 11 shows an example graph 1100 of PTT correlations for two detection methods (white dots) Foot IPG only, and (black dots) Dual-IPG method, consistent with various aspects of the present disclosure.

Figure 12:
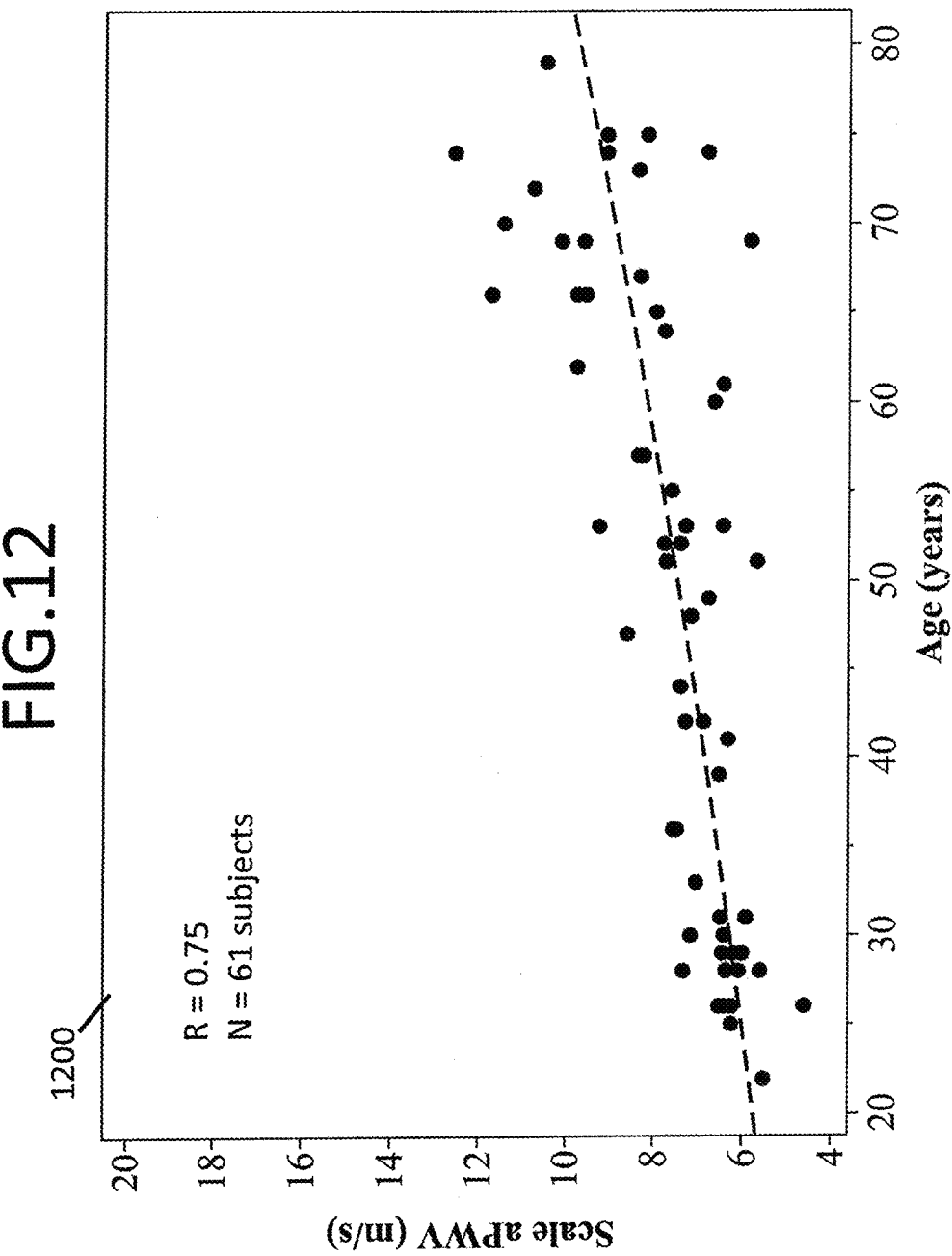
FIG. 12 shows an example graph of pulse wave velocity (PWV) obtained from the present disclosure compared to the ages of 61 human test subjects, consistent with various aspects of the present disclosure.

FIG. 12 shows an example graph 1200 of PWV obtained from the present disclosure compared to the ages of 61 human test subjects, consistent with various aspects of the present disclosure.

Figure 13:
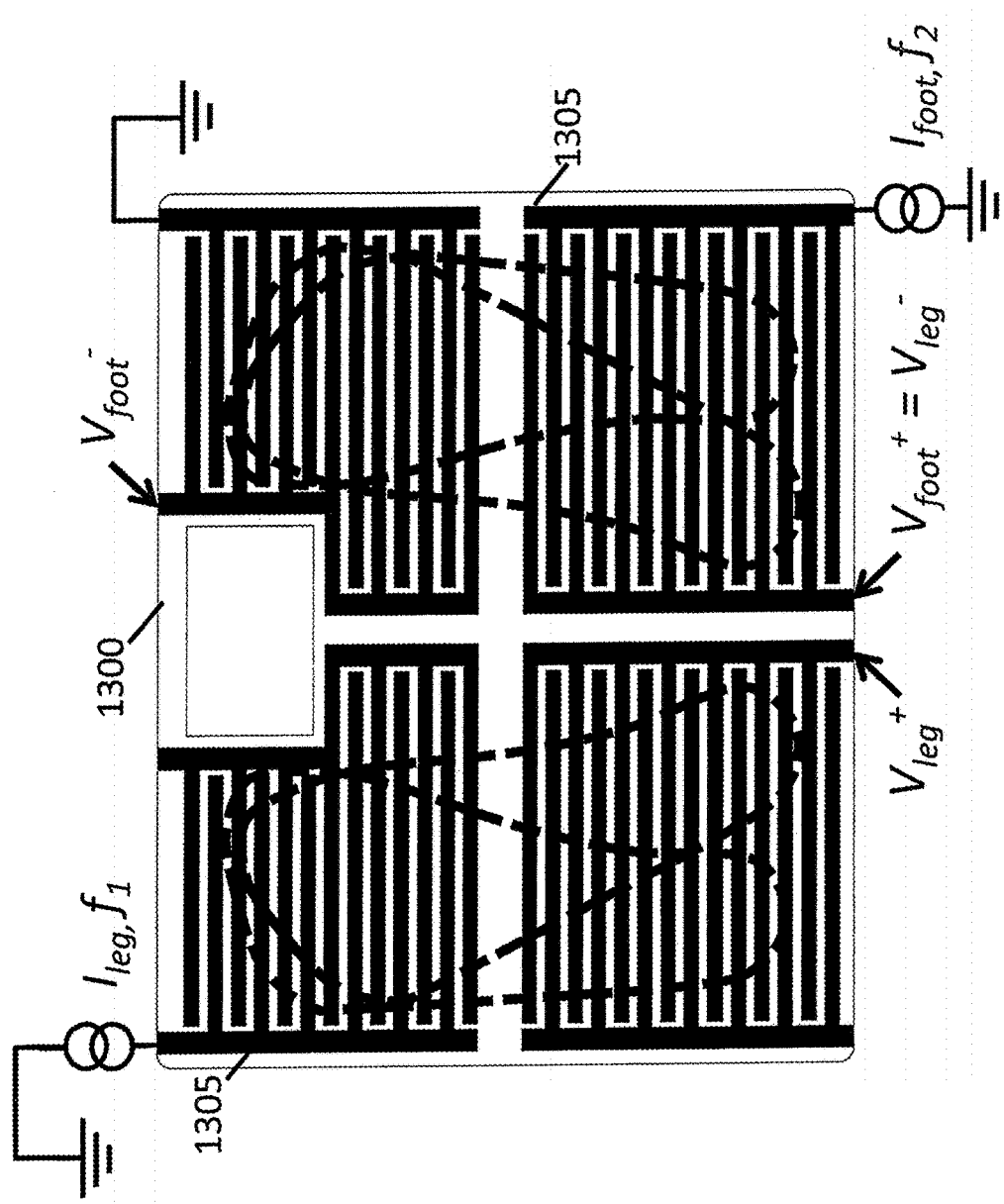
FIG. 13 shows another example of a scale with interleaved foot electrodes to inject and sense current from one foot to another foot, and within one foot, consistent with various aspects of the present disclosure.

FIG. 13 shows an example of a scale 1300 with integrated foot electrodes 1305 to inject and sense current from one foot to another foot, and within one foot.

FIG. 14a-c shows various examples of a scale 1400 with interleaved foot electrodes 1405 to inject/sense current from one foot to another foot, and measure Foot IPG signals in both feet.

FIGS. 15a-d shows an example breakdown of a scale 1500 with interleaved foot electrodes 1505 to inject and sense current from one foot to another foot, and within one foot.

Figure 16:
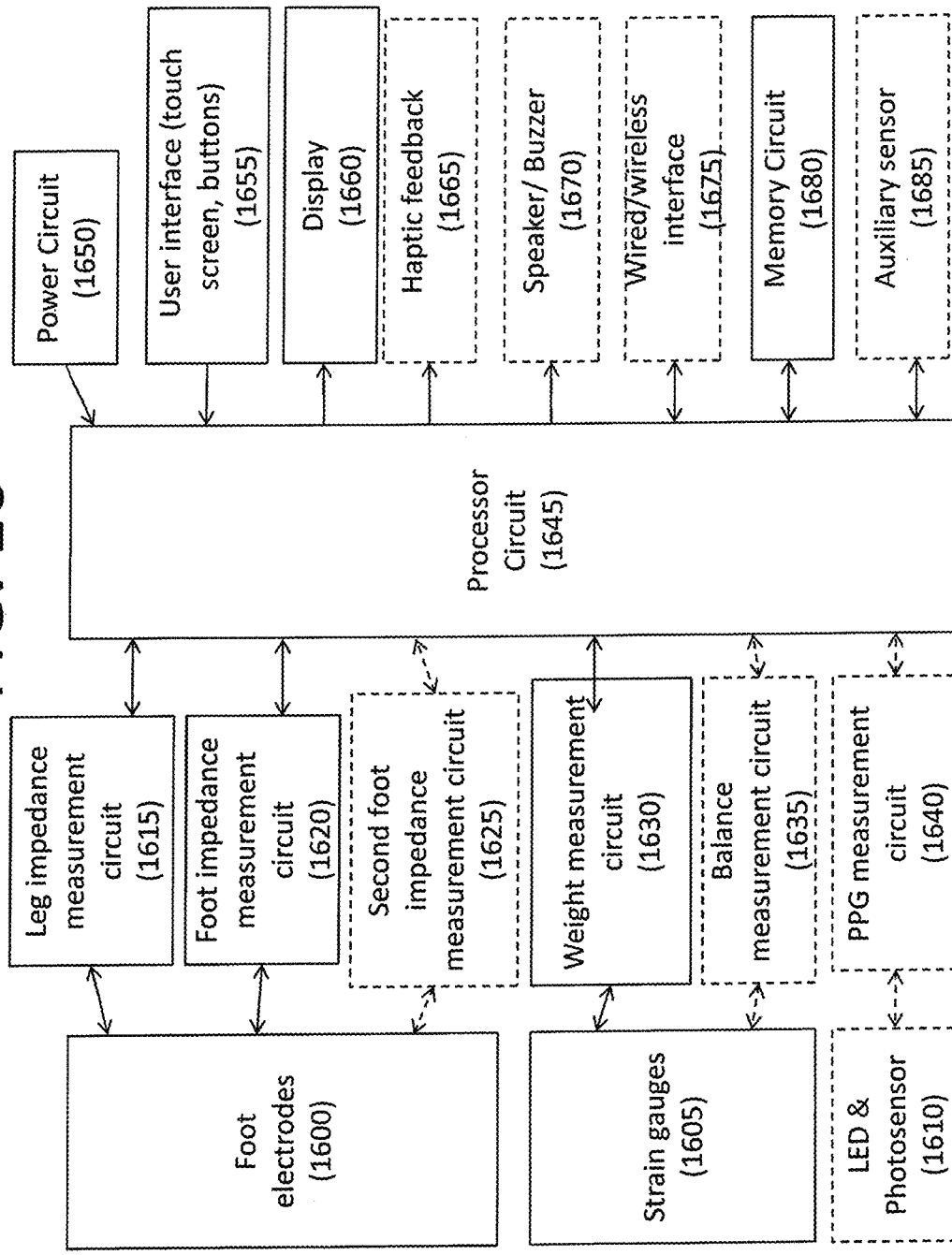
FIG. 16 shows an example block diagram of circuit-based building blocks, consistent with various aspects of the present disclosure.

FIG. 16 shows an example block diagram of circuit-based building blocks, consistent with various aspects of the present disclosure.

The various circuit-based building blocks shown in FIG. 16 can be implemented in connection with the various aspects discussed herein. In the example shown, the block diagram includes foot electrodes 1600 that can collect the IPG signals. Further, the block diagram includes strain gauges 1605, and an LED/photosensor 1610. The foot electrodes 1600 is configured with a leg impedance measurement circuit 1615, a foot impedance measurement circuit 1620, and an optional second foot impedance measurement circuit 1625. The leg impedance measurement circuit 1615, the foot impedance measurement circuit 1620, and the optional second foot impedance measurement circuit 1625 report the measurements collected to a processor circuitry 1645.

The processor circuitry 1645 collects data from a weight measurement circuit 1630 and an optional balance measurement circuit 1635 that are configured with the strain gauges 1605. Further, an optional photoplethysmogram (PPG) measurement circuit 1640, which collects data from the LED/photosensor 1610, provides data to the processor circuitry 1645.

The processor circuitry 1645 is powered via a power circuit 1650. Further, the processor circuitry 1645 collects user input data from a user interface 1655 (e.g., iPad®, smart phone and/or other remote user handy/CPU with a touch screen and/or buttons). The data collected/measured by the processor circuitry 1645 is shown to the user via a display 1660. Additionally, the data collected/measured by the processor circuitry 1645 can be stored in a memory circuit 1680. Further, the processor circuitry 1645 can optionally control a haptic feedback circuit 1665, a speaker or buzzer 1670, a wired/wireless interface 1675, and an auxiliary sensor 1685 for one-way or two-way communication between the scale and the user.

FIG. 17 shows an example flow diagram, consistent with various aspects of the present disclosure. At block 1700, a PWV length is entered. At block 1705, a user's weight, balance, leg, and foot impedance are measured. At 1710, the integrity of signals is checked (e.g., SNR). If the signal integrity check is not met, the user's weight, balance, leg, and foot impedance are measured again (block 1705), if the signals integrity check is met, the leg impedance pulse timings are extracted (as is shown at block 1715). At block 1720, foot impedance and pulse timings are extracted, and at block 1725, BCG timings are extracted. At block 1730, a timings quality check is performed. If the timings quality check is not validated, the user's weight, balance, leg and foot impedance are again measured (block 1705). If the timings quality check is validated, the PWV is calculated (as is shown at block 1735). At block 1740, the PWV is displayed to the user.

Figure 18A:
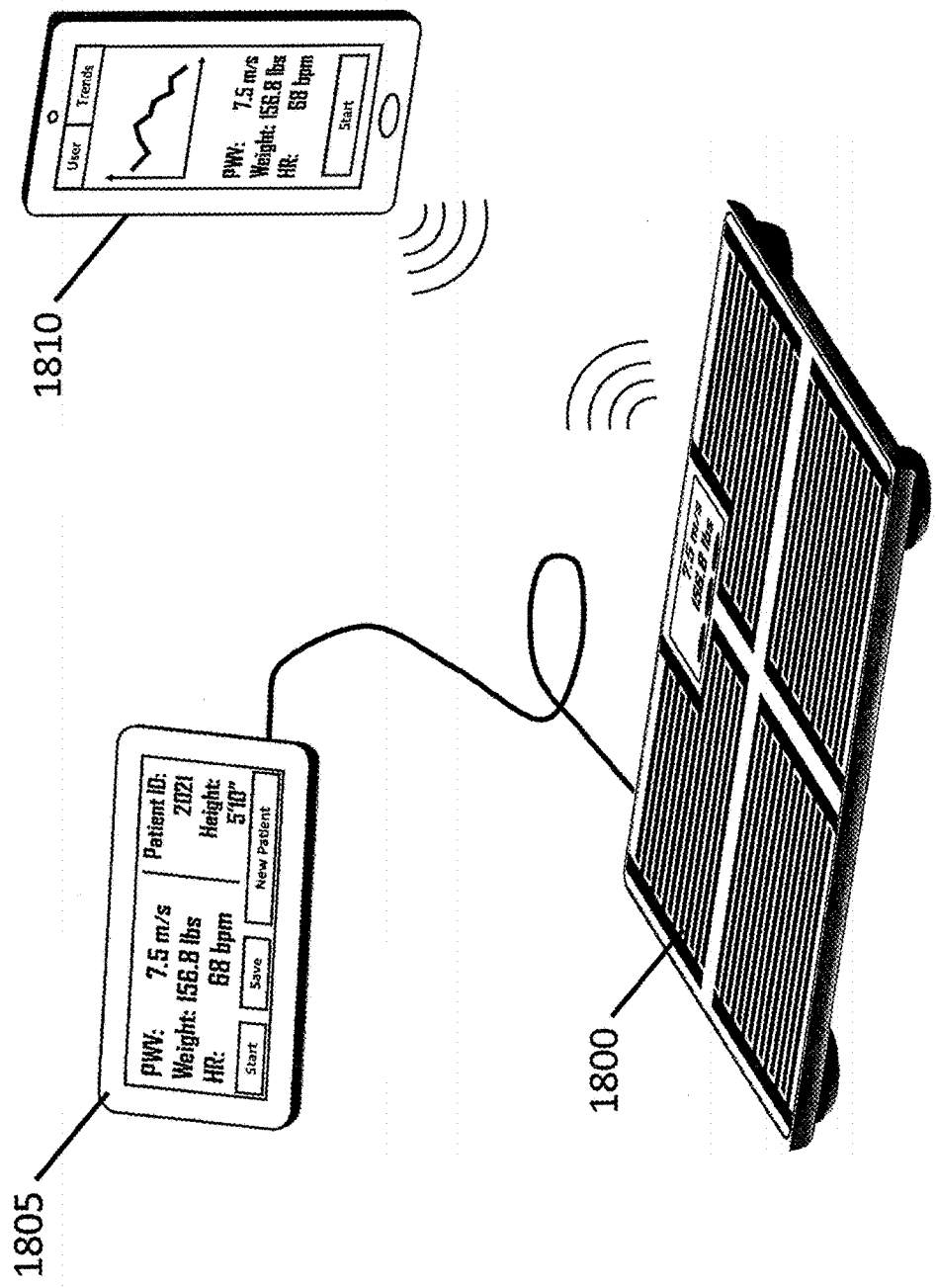
FIG. 18a shows an example scale communicatively coupled to a wireless device, consistent with various aspects of the present disclosure.

FIG. 18*a* shows an example scale 1800 communicatively coupled to a wireless device, consistent with various aspects of the present disclosure. As described herein, a display 1805 displays the various aspects measured by the scale 1800. The scale can also wirelessly broadcast the measurements to a wireless device 1810. The wireless device 1810 can also be implemented as an iPad®, smart phone or other CPU to provide input data for configuring and operating the scale.

As an alternative or complementary user interface used in other embodiments, the scale includes a foot-controlled user interface which is enabled/implementable by one or more foot-based biometrics (for example, with the user being correlated to previously-entered user weight, and/or foot size/shape). In certain embodiments, the user foot-based biometric is also implemented by the user manually entering data (e.g., a password) on the upper surface or display area of the scale. In implementations in which the scale is configured with a haptic, capacitive or flexible pressure-sensing upper surface, the (upper surface/tapping) touching from or by the user is sensed in the region of the surface and processed according to conventional X-Y grid Signal processing in the logic circuitry/CPU that is within the scale. By using one or more of the accelerometers located within the scale at its corners, such user data entry is sensed by each such accelerometer so long as the user's toe, heel or foot pressure associated with each tap provides sufficient force. Although the present discussion refers to a FUI, embodiments are not so limited. Various embodiments include internal or external GUIs that are in communication with the scale and used to obtain a biometric and that can be in place of the FUI and/or in combination with a FUI. For example, a user device having a GUI, such as tablet, is in communication with the scale via a wired or wireless connection. The user device obtains a biometric, such a finger print, and communicates the biometric to the scale.

In various embodiments, the above discussed user-interface is used with other features described herein for the purpose of controlling access to RX health information and providing additional non-RX health information such as: collecting the categories of interest input by the user, the biometric and/or passwords entered by the user, displaying the additional health information, and displaying an indication that RX health information can be accessed as a service or that additional health information is available. For example, the user enters the categories of interest to the scale using their foot and the user-interface. The user data (e.g., RX health information or other user data) might include less sensitive data (e.g., the user's weight) and more sensitive data (e.g., the user's scale obtains cardiograms and other data generated by or provided to the scale and associated with the user's symptoms and/or diagnoses). For data that may be more user-sensitive, the above described biometrics are used as directed by the user for indicating and defining protocol to permit such data to be exported from the scale to other remote devices and/or for such data to be displayed on the user-interface.

In some specific embodiments, the scale operates in different modes of data security and communication. The different modes of data security and communication are enabled in response to biometrics identified by the user and using the user-interface. In some embodiments, the scale is used by multiple users and/or the scale operates in different modes of data security and communication in response to identifying the user and based on biometrics. The different modes of data security and communication include, for example: a first mode (e.g., default mode) in which the user's body mass and/or weight is displayed regardless of any biometric which would associate with the specific user standing on the scale and no data is communicated to external circuitry; a second mode in which complicated/more-sensitive data (or data reviewed infrequently) is only exported from the scale under specific manual commands provided to the scale under specific protocols and in response to a biometric; and third mode or modes in which the user-specific data that is collected from the scale is processed and accessed based on the type of data and in response to a biometric. Such data categories include categories of different levels of importance and/or sensitivities such as the above-discussed high and low level data and other data that might be very specific to a symptom and/or degrees of likelihood for diagnoses. Optionally, the CPU in the scale is also configured to provide encryption of various levels of the user's sensitive data.

In some embodiments, the different modes of data security and communication are enabled in response to recognizing the user standing on the scale using a biometric and operating in a particular mode of data security and communication based on user preferences and/or services activated. For example, the different modes of operation include the default mode (as discussed above) in which certain data (e.g., categories of interest, categories of user data, or historical user data) is not communicated from the scale to external circuitry, a first communication mode in which data is communicated to external circuitry as identified in a user profile, a second or more communication modes in which data is communicated to a different external circuitry for further processing. The different communication modes are enabled based on biometrics identified from the user and user settings in a user profile corresponding with each user.

In a specific embodiment, a first user of the scale may not be identified and/or have a user profile set up. In response to the first user standing on the scale, the scale operates in a default mode. During the default mode, the scale displays the user's body mass and/or weight on the user display and does not output user data. A second user of the scale has a user profile set up that indicates the user would like data communicated to a computing device of the user. When the second user stands on the scale, the scale recognizes the second user based on a biometric and operates in a first communication mode. During the first communication mode, the scale outputs at least a portion of the user data to an identified external circuitry. For example, the first communication mode allows the user to upload data from the scale to a user identified external circuitry (e.g., the computing device of the user) that includes non-regulated health information. In the first communication mode, the scale performs the processing of the raw sensor data and/or the external circuitry can. For example, the scale sends the raw sensor data and/or non-regulated health information to a computing device of the user. The computing device may not provide access to the raw sensor data to the user and/or can send the raw sensor data to another external circuitry for further processing in response to a user input. For example, the computing device can ask the user if the user would like additional health information and/or regulated health information as a service. In response to receiving an indication the user would like the additional health information and/or regulated health information, the computing device outputs the raw sensor data and/or non-regulated health information to another external circuitry for processing, providing to a physician for review, and controlling access, as discussed above.

In one or more additional communication modes, the scale outputs raw sensor data to an external circuitry for further processing. For example, during a second communication mode and a third communication, the scale sends the raw sensor data and other data to external circuitry for processing. Using the above-provided example, a third user of the scale has a user profile set up that indicates the third user would like additional health information, such as non-regulated health information based on categories of interest. When the third user stands on the scale, the scale recognizes the third user based on one or more biometrics and operates in a second communication mode. During the second communication mode, the scale outputs the raw sensor data to the external circuitry. The external circuitry processes the raw sensor data, determines at least one physiologic parameter of the user, and derives the additional health information. The external circuitry allows access to the user to additional health information but does not allow the user to access regulated health information, including the physiologic parameter. For example, the regulated health information may not be accessed by the third user until the third user has paid a service fee and/or until a prescription by a physician is obtained. In some embodiments, the external circuitry outputs the additional health information and/or an indication that additional health information can be accessed to the scale to display to the third user on the user interface.

A fourth user of the scale has a user profile set up that indicates the fourth user has enabled a service to access regulated health information. When the fourth user stands on the scale, the scale recognizes the user based on one or more biometrics and operates in a fourth communication mode. In the fourth communication mode, the scale outputs raw sensor data to the external circuitry, and the external circuitry processes the raw sensor data and controls access to the data. For example, the external circuitry may not allow access to the regulated health information until a physician reviews the information. In some embodiments, the external circuitry outputs data to the scale, in response to physician review. For example, the output data can include the regulated health information and/or an indication that regulated health information is ready for review. The external circuitry may be accessed by the user, using the scale and/or another user device. In some embodiments, using the foot-controlled user-interface of the scale, the scale displays the regulated health information to the user. In various embodiments, if the scale is unable to identify a particular (high security) biometric that enables the fourth communication mode, the scale may operate in a different communication mode and may still recognize the user. For example, the scale may operate in a default communication mode in which the user data collected by the scale is stored in a user profile corresponding to the fourth user and on the scale. In some related embodiments, the user data is output to the external circuitry at a different time.

Although the present embodiments illustrates a number of security and communication modes, embodiments in accordance with the present disclosure can include additional or fewer modes. Furthermore, embodiments are not limited to different modes based on different users. For example, a single user may enable different communication modes in response to particular biometrics of the user identified and/or based on user settings in a user profile.

In various embodiments, the scale defines a user data table that defines types of user data and sensitivity values of each type of user data. In specific embodiments, the user interface (e.g., FUI) displays the user data table. In other specific embodiments a user interface of a smartphone, tablet, and/or other computing device displays the user data table. For example, a wired or wireless tablet is used, in some embodiments, to display the user data table. The sensitivity values of each type of user data, in some embodiments, define in which communication mode(s) the data type is communicated and/or which biometric is used to enable communication of the data type. In some embodiments, a default or pre-set user data table is displayed and the user revises the user data table using the FUI. The revisions are in response to user inputs using the user's foot and/or contacting or moving relative to the FUI. In a specific example, when the user stands on the platform of the scale, and the scale detects touching of the toe, the scale can reject the toe touch (or tap) as a foot signal (e.g., similar to wrist rejection for capacitive tablets with stylus). Although the embodiments are not so limited, the above (and below) described control and display is provided using a wireless or wired tablet or other computing device as a user interface. The output to the wireless or wired tablet, as well as additional external circuitry, is enabled using biometrics. For example, the user is encouraged, in particular embodiments, to configure the scale with various biometrics. The biometric include scale-based biometrics and biometrics from the tablet or other user computing device. The biometric, in some embodiments, used to enable output of data to the tablet and/or other external circuitry includes a higher integrity biometric (e.g., higher likelihood of identifying the user accurately) than a biometric used to identify the user and stored data on the scale.

Biometrics, as used herein, are metrics related to human characteristics and used as a form of identification and access control. Scale-based biometrics includes biometrics that are obtained using signals collected by the data-procurement circuitry of the scale (e.g., using electrodes and/or force sensors). Example scale-based biometrics include foot length, foot width, weight, voice recognition, facial recognition, a passcode tapped and/or picture drawn with a foot of the user on the FUI/GUI of the user display, among other biometrics. In some specific embodiments, a scale-based biometric includes a toe-print (e.g., similar to a finger print) that is recognized using a toe-print reader on the FUI/GUI of the scale. The toe print can be used as a secure identification of the user. In other embodiments, the scale-based biometric includes a finger print captured using external circuitry in communication with the scale (e.g., a cellphone or tablet having finger print recognition technology).

An example user data table is illustrated below:

| User-data Type | Weight, local weather | Body Mass Index, user specific news | User-Specific Advertisements | Physician-Provided Diagnosis/Report | Scale-stored suggestions (symptoms & diagnosis) |
|---|---|---|---|---|---|
| Sensitivity (10 = highest, 1 = lowest) | 1 | 3 | 5 | 10 | 9 |

The above-displayed table is for illustrative purposes and embodiments in accordance with the present disclosure can include additional user-data types than illustrated, such as cardiogram characteristics, clinical indications, physiologic parameters, user goals, demographic information, etc. In various embodiments, the user data table includes additional rows than illustrated. The rows, in specific embodiments, include different data input sources and/or sub-data types (as discussed below). Data input sources include source of the data, such as physician provided, input from the Internet, user provided, from the external circuitry. The different data from the data input sources, in some embodiments, is used alone or in combination.

In various embodiments, the user adjusts the table displayed above to revise the sensitivity values of each data type. Further, although the above-illustrated table includes a single sensitivity value for each data type, in various embodiments, one or more of the data types are separated into sub-data types and each sub-data type has a sensitivity value. As an example, the user-specific advertisement is separated into: prescription advertisement, external device advertisements, exercise advertisements, and diet plan advertisement. Alternatively and/or in addition, the sub-data types for user-specific advertisement include generic advertisements based on a demographic of the user and advertisements in response to scale collected data (e.g., advertisement for a device in response to physiologic parameters), as discussed further herein.

For example, weight data includes the user's weight and historical weight as collected by the scale. In some embodiments, weight data includes historical trends of the user's weight and correlates to dietary information and/or exercise information, among other user data. Body mass index data, includes the user's body mass index as determined using the user's weight collected by the scale and height. In some embodiments, similar to weight, body mass index data includes history trends of the user's body mass index and correlates to various other user data.

User-specific advertisement data includes various prescriptions, exercise plans, dietary plans, and/or other user devices and/or sensors for purchase, among other advertisements. The user-specific advertisements, in various embodiments, are correlated to input user data and/or scale-obtained data. For example, the advertisements include generic advertisements that are relevant to the user based on a demographic of the user. Further, the advertisements include advertisements that are responsive to scale collected data (e.g., physiologic parameter includes a symptom or problem and advertisement is correlated to the symptom or problem). A number of specific examples include advertisements for beta blockers to slow heart rate, advertisements for a user wearable device (e.g., Fitbit®) to monitor heart rate, and advertisements for a marathon exercise program (such as in response to an indication the user is training for a marathon), etc.

Physician provided diagnosis/report data includes data provided by a physician and, in various embodiments, is in responsive to the physician reviewing the scale-obtained data. For example, the physician provided diagnosis/report data includes diagnosis of a disorder/condition by a physician, prescription medication prescribed by a physician, and/or reports of progress by a physician, among other data. In various embodiments, the physician provided diagnosis/reports are provided to the scale from external circuitry, which includes and/or accesses a medical profile of the user.

Scaled stored suggestion data includes data that provides suggestions or advice for symptoms, diagnosis, and/or user goals. For example, the suggestions include advice for training that is user specific (e.g., exercise program based on user age, weight, and cardiogram data or exercise program for training for an event or reducing time to complete an event, such as a marathon), suggestions for reducing symptoms including dietary, exercise, and sleep advice, and/or suggestions to see a physician, among other suggestions. Further, the suggestions or advice include reminders regarding prescriptions. For example, based on physician provided diagnosis/report data and/or user inputs, the scale identifies the user is taking a prescription medication. The identification includes the amount and timing of when the user takes the medication, in some embodiments. The scale reminds the user and/or asks for verification of consumption of the prescription medication using the foot-controlled user interface.

As further specific examples, recent discoveries may align and associate different attributes of scale-based user data collected by the scale to different tools, advertisements, and physician provided diagnosis. For example, it has recently been discovered that atrial fibrillation is more directly correlated with obesity. The scale collects various user data and monitors weight and various components/symptoms of atrial fibrillation. In a specific embodiment, the scale recommends/suggests to the user to: closely monitor weight, recommends a diet, goals for losing weight, correlates weight gain and losses for movement in cardiogram data relative to arrhythmia. The movement in cardiogram data relative to arrhythmia, in specific embodiments, is related to atrial fibrillation. For example, atrial fibrillation is associated with indiscernible p-waves and beat to beat fluctuations. Thereby, the scale correlates weight gain/loss with changes in amplitude (e.g., discernibility) of a p-wave of a cardiogram (preceding a QRS complex) and changes in beat to beat fluctuations.

Figure 18B:
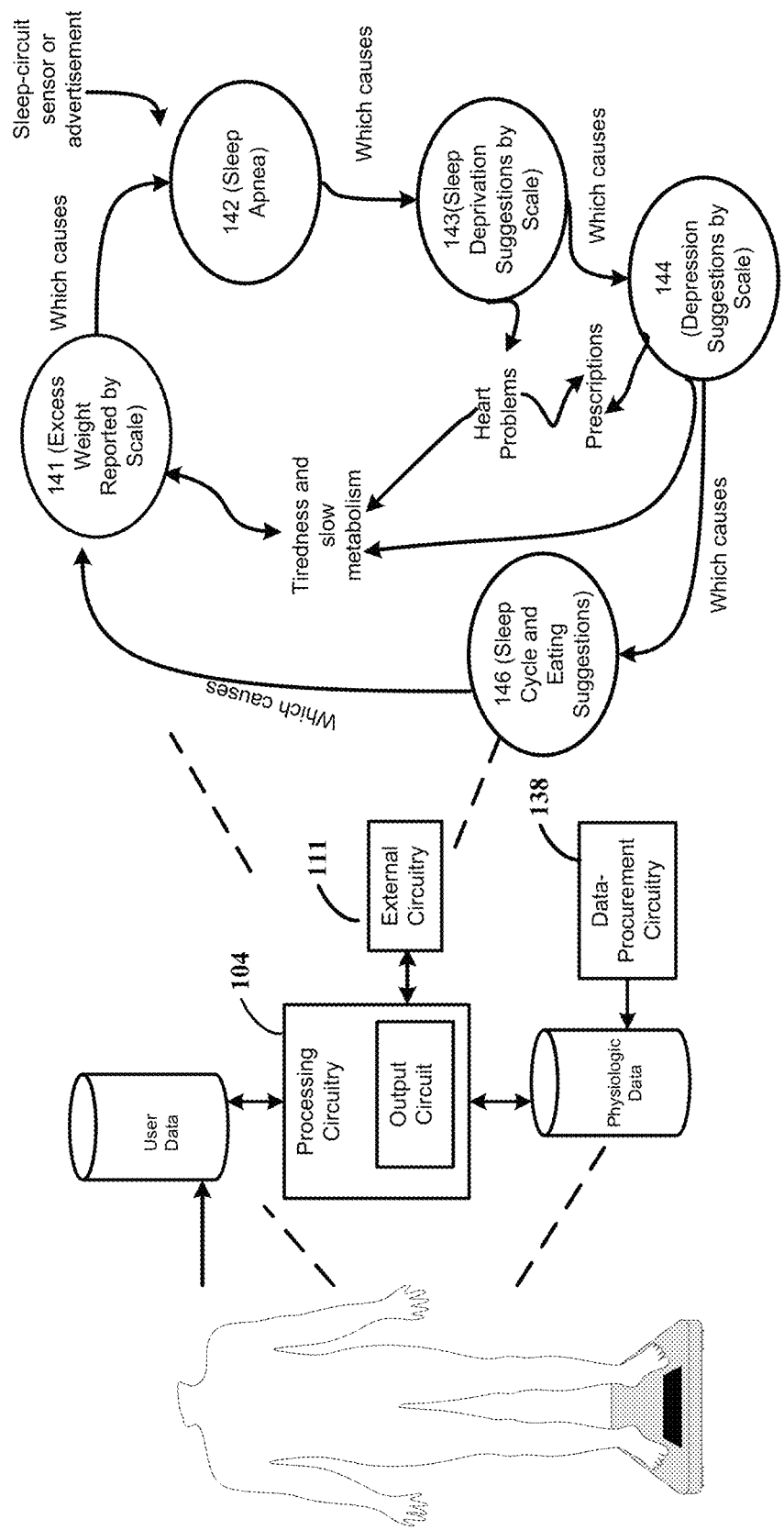
FIG. 18b shows an example scale communicatively coupled to external circuitry and various data types provided to a user, consistent with various aspects of the present disclosure.

FIG. 18b shows an example scale communicatively coupled to external circuitry and various data types provided to a user, consistent with various aspects of the present disclosure. The scale as illustrated by FIG. 18b includes the scale illustrated by FIG. 1a and/or FIG. 1b. As illustrated, the apparatus includes a platform, a user display, a platform for the user to stand on, data-procurement circuitry 138, and processing circuitry 104. The data-procurement circuitry 138 includes force-sensor circuitry and a plurality of electrodes (e.g., the physiologic sensors 108) which are integrated with the data-procurement circuitry 138. As previously discussed, the scale includes an output circuit to send the user data to external circuitry 111. The external circuitry 111, in various embodiments, receives the user-data and determines the physiologic parameters of the user using the user data.

The various data types provided to the user, in some embodiments, are used to monitor atrial fibrillation. Atrial fibrillation, for example, causes additional problems, such as sleep deprivation and depression. Further, as discussed above, it has been recently discover that atrial fibrillation is more directly correlated to obesity and, in particular, to recent weight gains. As illustrated by FIG. 18b, at block 141, excess weight is reported by the scale. The excess weight, in some embodiments, includes an indication that the user is obese based on a user weight measured using the scale, and a height and age input by the user. In various embodiments, the scale provides an indication of a recent increase of weight over a threshold value. In accordance with a number of embodiments, the scale provides suggestions to the user, such as goals for losing weight.

The excess weight causes, for some users, sleep apnea. As such, at block 142, sleep apnea is reported to the scale by a sleep-circuit sensor, by a user, and/or as part of physician provided diagnosis/reports data. The sleep-circuit sensor includes, in various embodiments, a smart bed or other user sensor circuitry (e.g., cell phone laying on the bed, Fitbit®, etc.) that measures cardiogram data and/or movement data while the user is sleeping. In various embodiments, whether or not the user has sleep apnea is unknown by the scale. In such embodiments, at block 142, the scale displays an advertisement for a sleep-circuit sensor to the user using the foot-controlled user interface. Further, the scale, in some specific embodiments and in response to reporting of sleep apnea input to the scale, displays an advertisement for prescription medicine for sleep apnea, treatments for sleep apnea, and/or a physician or study for sleep apnea, among other advertisements.

In various embodiments, sleep apnea causes sleep deprivation. At block 143, in response to reporting of sleep apnea and/or an advertisement for a sleep-circuit sensor, the scale provides sleep deprivation suggestions to the user. The sleep deprivation suggestions, in some embodiments, include suggestions to see a physician for sleep apnea, exercise advice, or dietary advice, among other suggestions. Sleep deprivation causes various other problems, such as heart problems, tiredness and slow metabolism (which correlate to the excess weight of the user), and/or leads to prescription medication. Further, sleep deprivation causes depression. At block 144, in response to the sleep deprivation suggestions, the scale provides depression suggestions to the user, such as using the FUI. The suggestions include prescription medications suggestions, exercise advice, suggestions to see a physician, among other suggestions. Further, the scale, in some embodiments, provides advertisements for specific depression prescription medication, physician specializing in depression or trials for depression, and/or exercise or dietary programs, among other advertisements. Depression, in various embodiments, causes tiredness and slow metabolism and results in prescription medication.

Further, in some embodiments, depression causes sleep cycle and eating problems. For example, a user that is depressed may stay up late and which may result in eating additional snacks. At block 146, in response to the depression suggestions and/or reports of sleep cycle or eating issues input to the scale, the scale provides sleep cycle and eating suggestions. For example, another user wearable device, in some embodiments, reports the sleep cycle or eating issue to the scale. As a specific embodiment, a user may wear a user wearable device (e.g., Fitbit®) to track various data, such as cardiogram data, exercise data, and sleep cycle data. Further, the user inputs eating habits to the user wearable device. The user wearable device, in such embodiments, communicates the sleep cycle and eating habit data to the scale. The sleep cycle and eating suggestions, in various embodiments, include suggestions to improve the user's sleep cycle (e.g., indication of hours sleeping, exercise advice, dietary advice, such as a time of the day to stop eating), dietary advice, exercise advice, among other lifestyle advice (e.g., stop watching television one hour before bed). Sleep cycle and eating issues cause, in various embodiments, the excess weight of the user. Further, excess weight is correlated to tiredness and slow metabolism.

In various embodiments, the scale and various user data is used to monitor atrial fibrillation (AFIB) of the user and various related problems of AFIB. Various scale-based suggestions and advertisements are provided to the user, such as using the foot-controlled user interface, to assist in monitoring the user's condition, monitoring symptoms or related problems, and educating the user on symptoms, related problems, and the correlation thereof. Further, physician provided diagnosis/reports data is used to refine the monitoring of the condition and provide feedback to the user. The excess weight causes and/or increases the risk, for some users, AFIB. Further, a recent increase in weight that is over a threshold amount can also include an increased risk for AFIB. The scale is used to monitor BCG, IPG, PWV, and other cardio-indicators of AFIB (e.g., rhythm disturbance, amplitude variations in BCG and/or IPG).

FIGS. 19a-c show example impedance as measured through different parts of the foot based on the foot position, consistent with various aspects of the present disclosure. For instance, example impedance measurement configurations may be implemented using a dynamic electrode configuration for measurement of foot impedance and related timings. Dynamic electrode configuration may be implemented using independently-configurable electrodes to optimize the impedance measurement. As shown in FIG. 19a, interleaved electrodes 1900 are connected to an impedance processor circuit 1905 to determine foot length, foot position, and/or foot impedance. As is shown in FIG. 19b, an impedance measurement is determined regardless of foot position 1910 based on measurement of the placement of the foot across the electrodes 1900. This is based in part in the electrodes 1900 that are engaged (blackened) and in contact with the foot (based on the foot position 1910), which is shown in FIG. 19c.

More specifically regarding FIG. 19a, configuration includes connection/de-connection of the individual electrodes 1900 to the impedance processor circuit 1905, their configuration as current-carrying electrodes (injection or return), sense electrodes (positive or negative), or both. The configuration is preset based on user information, or updated at each measurement (dynamic reconfiguration) to optimize a given parameter (impedance SNR, measurement location). The system algorithmically determines which electrodes under the foot to use in order to obtain the highest SNR in the pulse impedance signal. Such optimization algorithm may include iteratively switching configurations and measuring the impedance, and selecting the best suited configuration. Alternatively, the system first, through a sequential impedance measurement between each individual electrode 1900 and another electrode in contact with the body (such as an electrode in electrode pair 205 on the other foot), determine which electrodes are in contact with the foot. By determining the two most apart electrodes, the foot size is determined. Heel location can be determined in this manner, as can other characteristics such as foot arch type. These parameters are used to determine programmatically (in an automated manner by CPU/logic circuitry) which electrodes are selected for current injection and return (and sensing if a Kelvin connection issued) to obtain the best foot IPG.

In various embodiments involving the dynamically reconfigurable electrode array 1900/1905, an electrode array set is selected to measure the same portion/segment of the foot, irrespective of the foot location on the array. FIG. 19b illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume/segment of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. With respect to FIG. 19b, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 19c shows an example embodiment involving dynamic reconfiguration of the electrodes to reduce such foot placement-induced variations. As an example, by sensing the location of the heel first (as described above), it is possible to activate a subset of electrodes under the heel, and another subset of electrodes separated by a fixed distance (1900). The other electrodes (e.g., unused electrodes) are left disconnected. The sensed volume will therefore be the same, producing consistent timings. The electrode configuration leading to the most consistent results may be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale).

In certain embodiments, the apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary because the user placed the one foot at a slightly different position on the platform or scale. In FIG. 19a, the foot-to-electrode locations for the heel are different locations than that shown in FIGS. 19b and 19c. As this different foot placement can occur from day to day for the user, the timing and related impedance measurements are for the same (internal) segment of the foot. By having the processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporated the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to a peripheral device such as a computer, smart phone, tablet computing device. The communication occurs to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contacts feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Various embodiments are implemented in accordance with, and fully incorporating by reference for their general teachings, the above-identified PCT Applications and U.S. Provisional Applications (including PCT Ser. No. PCT/US2016/062484 and PCT Ser. No. PCT/US2016/062505), which teachings are also incorporated by reference specifically concerning physiological scales and related measurements and communications such as exemplified by disclosure in connection with FIGS. 1a, 1b, 1e-1f, and 2b-e PCT Ser. No. PCT/US2016/062484 and FIGS. 1a, 1c, 1k, 1m, 1n, 1o, in PCT Ser. No. PCT/US2016/062505, and related disclosure in the above-identified U.S. Provisional Applications. For example, U.S. Provisional Application (Ser. No. 62/258,253), which teachings are also incorporated by reference specifically concerning using a scale to instruct a user to have a particular posture while obtaining scale-data features and aspects as exemplified by disclosure in connection with FIGS. 1a-1b of the underlying provisional; U.S. Provisional Application (Ser. No. 62/260,174), which teachings are also incorporated by reference specifically concerning remotely processing physiological data and providing generic health information based on categories of interest features and aspects as described in connection with FIGS. 1a-1e in the underlying provisional; and U.S. Provisional Application (Ser. No. 62/266,523), which teachings are also incorporated by reference specifically concerning grouping users into inter and intra scale social groups based on aggregated user data sets, and providing normalized user data to other users in the social group aspects as exemplified by disclosure in connection with FIGS. 1a-1c of the underlying provisional.

For instance, embodiments herein and/or in the PCT and provisional applications may be combined in varying degrees (including wholly). Reference may also be made to the experimental teachings and underlying references provided in the PCT and provisional applications. Embodiments discussed in the provisional applicants are not intended, in any way, to be limiting to the overall technical disclosure, or to any part of the claimed invention unless specifically noted.

Reference may also be made to published patent documents U.S. Patent Publication 2010/0094147 and U.S. Patent Publication 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based building blocks and/or modules may be implemented to carry out one or more of the operations/activities described herein shown in the block-diagram-type figures. In such contexts, these building blocks and/or modules represent circuits that carry out these or related operations/activities. For example, in certain embodiments discussed above (such as the pulse circuitry modularized as shown in FIGS. 3a-b), one or more blocks/modules are discrete logic circuits or programmable logic circuits for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory circuit. As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that the above described aspects and features, and without limitation to the number thereof, can be combined in specific designs so that the scale is configured and arranged to perform these aspects and features in combination in a manner consistent with the description thereof. Further, based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. An apparatus including:
a scale comprising:
  a user display configured to display data to a user,
  a platform configured for the user to stand on,
  data-procurement circuitry, including force sensor circuitry and a plurality of electrodes integrated with the platform, and configured to engage the user with electrical signals and collect signals indicative of an identity of the user and cardio-physiological measurements while the user is standing on the platform, and
  processing circuitry, including a central processing unit (CPU) and a memory circuit with user-corresponding data, configured with the data-procurement circuitry to process data obtained by the data-procurement circuitry while the user is standing on the platform and therefrom generate cardio-related physiologic data and determine the identity of the user, the processing circuitry further configured to determine activation of a scale-data based service for the user based on the determined identity of the user, the scale-data based service related to providing additional health information correlated to the user and categories of interest associated with the user including user demographic data and including disorder or symptom data of the user, wherein the disorder or symptom data is derived from the generated cardio-related physiologic data; and
  an output circuit configured to receive user data and, in response to the determined activation of the scale-data based service for the user, send the user data, including data indicative of the user's identity and the generated cardio-related physiologic data, from the scale for reception at a remote location, and further configured to display, on the user display, a weight of the user and at least a portion of the generated cardio-related physiologic data; and external circuitry configured to:
receive and validate the user data as concerning the user associated with a user identifier (ID) and determine at least one physiologic parameter of the user using the user data; and derive the additional health information corresponding to the user data based on the categories of interest and output the additional health information to the scale for display on the user display or for communication by the scale for display on a user device in communication with the scale, wherein the external circuitry is to communicate with the processing circuitry and is to receive the user data, and instruct the scale to ask for the categories of interest, and then correlate the user data with the categories of interest.

2. The apparatus of claim 1, wherein the processing circuitry determines identification of the user and a corresponding user ID based on biometric data obtained from the user while the user is standing on the platform.

3. The apparatus of claim 2, wherein the scale further includes a speaker component configured and arranged to capture voice sounds from the user and the data indicative of the identity of the user includes voice sounds captured by the speaker component.

4. The apparatus of claim 1, wherein the data-procurement circuitry and the processing circuitry are further configured and arranged to activate the scale-data based service by providing a number of questions to the user including:
asking if the user is interested in the additional health information; and
asking the user for the categories of interest.

5. The apparatus of claim 1, wherein the data-procurement circuitry and the processing circuitry are further configured and arranged to provide a number of questions to the user including asking the user if the user has a symptom occurring and to activate the scale-data based service in response to answers to the questions.

6. An apparatus including:
a scale comprising:
a user display configured and arranged to display data to a user,
a platform configured and arranged for the user to stand on,
data-procurement circuitry, including force sensor circuitry and a plurality of electrodes integrated with the platform, and configured and arranged to engage the user with electrical signals and collect signals indicative of an identity of the user and cardio-physiological measurements while the user is standing on the platform, and
processing circuitry, including a central processing unit (CPU) and a memory circuit with user-corresponding data, configured and arranged with the data-procurement circuitry to process data obtained by the data-procurement circuitry while the user is standing on the platform and therefrom generate cardio-related physiologic data and determine the identity of the user, the processing circuitry further configured and arranged to determine activation of a scale-data based service for the user based on the determined identity of the user, the scale-data based service related to providing additional health information correlated to the user and categories of interest associated with the user including user demographic data and including disorder or symptom data of the user, wherein the disorder or symptom data is derived from the generated cardio-related physiologic data; and an output circuit configured and arranged to receive user data and, in response to the determined activation of the scale-data based service for the user, send the user data, including data indicative of the user's identity and the generated cardio-related physiologic data, from the scale for reception at a remote location, and further configured and arranged to display, on the user display, a weight of the user and at least a portion of the generated cardio-related physiologic data; and external circuitry configured to:
receive and validate the user data as concerning the user associated with a user identifier (ID) and determine at least one physiologic parameter of the user using the user data; and derive the additional health information corresponding to the user data based on the categories of interest and output the additional health information to the scale for display on the user display or for communication by the scale for display on a user device in communication with the scale, wherein the external circuitry is configured and arranged to:
receive the user data;
instruct the scale to ask for the categories of interest; and
in response to receiving the categories of interest from the scale, correlate the user data with the categories of interest and, therefrom, derive the additional health information.

7. The apparatus of claim 1, wherein the external circuitry includes an output circuit configured and arranged to receive the at least one physiologic parameter and, in response, send the at least one physiologic parameter to the scale, wherein the processing circuitry and the user display are configured and arranged to, responsive to receiving the at least one physiologic parameter from the external circuitry, display the at least one physiologic parameter to the user.

8. The apparatus of claim 1, wherein the external circuitry is configured and arranged to allow access to the at least one physiologic parameter to a physician corresponding with the user and not allow access to the at least one physiologic parameter to the user.

9. A method comprising:
engaging a user, via a scale, with electrical signals and, therefrom, collecting signals indicative of the user's identity while the user is standing on a platform of the scale, wherein the scale includes:
a user display,
the platform configured and arranged for the user to stand on,
data-procurement circuitry, including force sensor circuitry and a plurality of electrodes integrated with the platform,
processing circuitry being electrically integrated with the force sensor circuitry and the plurality of electrodes, and
an output circuit;
processing, using the processing circuitry, data obtained by the data-procurement circuitry while the user is standing on the platform and therefrom generating cardio-related physiologic data corresponding to the collected signals;

displaying a weight of the user on the user display;
determining an identity of the user from the data obtained by the data-procurement circuitry and, based on the identity of the user, determining activation of a scale-data based service for the user, the scale-data based service related to providing additional health information correlated to the user and categories of interest associated with the user including user demographic data and including disorder or symptom data of the user, wherein the disorder or symptom data is derived from the generated cardio-related physiologic data;
outputting, using the output circuit, user data including data indicative of the identity of the user and the generated cardio-related physiologic data in response to the determined activation of the scale-data based service for the user, from the scale for reception by external circuitry at a remote location;
validating the user data as concerning the user associated with a user identifier (ID);
determining, using the external circuitry, at least one physiologic parameter of the user using the user data;
deriving the additional health information for the user by correlating the categories of interest to the at least one physiologic parameter; and
outputting the additional health information to the scale or a user device associated with the user and in communication with the scale for display,
wherein the external circuitry is to:
receive the user data;
instruct the scale to ask for the categories of interest; and
in response to receiving the categories of interest from the scale, correlate the user data with the categories of interest and, therefrom, derive the additional health information.

10. The method of claim 9, wherein correlating the categories of interest to the at least one physiologic parameter includes comparing statistical data of a sample census pertinent to the categories of interest and the at least one physiologic parameter.

11. The method of claim 9, wherein correlating the categories of interest to the at least one physiologic parameter includes comparing statistical data of a sample census pertinent to the categories of interest and values of the at least one physiologic parameter of the sample census.

12. The method of claim 9, further including:
outputting the at least one of the physiologic parameter and the additional health information to the scale; and
responsive to receiving the at least one of the physiologic parameter and the additional health information from the external circuitry, displaying the at least one of the physiologic parameter and the additional health information to the user via a user display of the scale.

13. The method of claim 9, further including querying the user, using the scale, for the categories of interest and outputting the categories of interest to the external circuitry.

14. The method of claim 9, further include providing the additional health information to the user, via the scale, wherein the additional health information includes average physiologic parameter values of a sample census that is set by the user via the categories of interest.

15. The apparatus of claim 1, wherein the scale is updated with the additional health information communicated from the external circuitry.

16. The apparatus of claim 1, wherein the external circuitry is further configured and arranged to determine the at least one physiologic parameter using the physiologic parameter, the at least one physiologic parameter being included in the additional health information, and the scale is updated with the additional health information communicated from the external circuitry.

17. The apparatus of claim 1, wherein the scale is used by a plurality of users including at least the user and one other user, the processing circuitry is further configured and arranged to identify the user from the other of the plurality of users, and in response, determine the activation of the scale-data based service for at least the user of the plurality of users based on the identity of the user.

18. The apparatus of claim 17, wherein the processing circuitry is configured and arranged to identify each of the plurality of users from one another, and in response, to determine which of the plurality of users has activated the scale-data based service associated with additional health information, and the output circuit is configured and arranged with the processing circuitry to selectively output subsets of the respective user data in response to determining the activation of the scale-data based service for selective ones of the plurality of users, the selective ones including at least the user of the plurality of users.

19. The apparatus of claim 1, wherein the scale is used by a plurality of users including at least the user and one other user, the scale being configured and arranged to operate in different modes of data communication for the plurality of users including a medical professional mode and a scale-user mode, and depending on activation of the scale-data based service and which of the different modes is being operated, the scale is to send the user data to the external circuitry for generating the additional health information.

20. The apparatus of claim 19, wherein the scale is updated with the additional health information communicated from the external circuitry to revise the scale for the user.

* * * * *